A2

United States Patent
Taniguchi et al.

(10) Patent No.: US 6,495,546 B1
(45) Date of Patent: Dec. 17, 2002

(54) PROPANOLAMINE DERIVATIVES

(75) Inventors: Kiyoshi Taniguchi, Kobe; Minoru Sakurai, Toyonaka; Naoaki Fujii, Takatsuki; Kumi Hosoi, Susono; Yasuyo Tomishima, Osaka; Hisashi Takasugi, Sakai; Hajime Sogabe, Tokyo; Hirofumi Ishikawa, Suita; Naomi Hanioka, Minoo, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/646,878

(22) PCT Filed: Mar. 25, 1999

(86) PCT No.: PCT/JP99/01500

§ 371 (c)(1),
(2), (4) Date: Nov. 22, 2000

(87) PCT Pub. No.: WO99/51564

PCT Pub. Date: Oct. 14, 1999

(30) Foreign Application Priority Data

Apr. 6, 1998 (AU) .............................................. PP2826
Aug. 4, 1998 (AU) .............................................. PP5058

(51) Int. Cl.[7] ....................... A61K 31/54; A61K 31/535;
A61K 31/34; A61K 31/24; C07D 211/06;
C07D 211/70; C07C 211/00; C07C 233/00;
C07C 235/00; C07C 229/00

(52) U.S. Cl. ................................ 514/222.5; 514/222.5;
514/223.8; 514/231.2; 514/237.8; 514/255;
514/259; 514/307; 514/311; 514/319; 514/357;
514/382; 514/383; 514/385; 514/403; 514/415;
514/428; 514/443; 514/459; 514/468; 514/471;
514/475; 514/534; 514/539; 514/541; 514/561;
514/562; 514/563; 514/577; 514/617; 544/8;
544/67; 544/159; 544/162; 544/283; 544/358;
544/386; 544/398; 544/402; 546/139; 546/146;
546/149; 546/152; 546/168; 546/176; 546/205;
546/206; 546/207; 546/314; 546/329; 546/334;
548/128; 548/131; 548/160; 548/252; 548/254;
548/262.4; 548/267.2; 548/356.1; 548/492;
548/493; 548/503; 548/509; 548/510; 548/511;
548/530; 548/556; 548/566; 549/58; 549/405;
549/407; 549/425; 549/426; 549/467; 549/469;
549/491; 549/551; 560/10; 560/21; 560/22;
562/427; 562/429; 562/430; 562/433; 562/435;
562/462; 562/466; 564/306; 564/307; 564/308;
564/162; 564/163; 564/164; 564/165; 564/167;
564/170; 564/171; 564/173

(58) Field of Search ................................ 546/329, 149,
546/205, 314, 334, 139, 146, 152, 168,
176, 206, 207; 544/402, 7, 8, 67, 159, 162,
283, 358, 386, 398; 548/254, 128, 131,
160, 252, 262.4, 267.2, 356.1, 492, 493,
503, 509, 510, 511, 530, 556, 566; 549/407,
425, 467, 491, 551, 58, 405, 426, 469;
564/307, 308, 172, 306, 162, 163, 164,
165, 167, 170, 171; 560/10, 21, 22; 562/427,
429, 430, 433, 434, 435, 462, 466; 514/222.5,
223.8, 231.2, 237.8, 255, 259, 307, 311,
319, 357, 382, 383, 385, 403, 415, 428,
443, 459, 468, 471, 475, 534, 539, 541,
561, 562

(56) References Cited

FOREIGN PATENT DOCUMENTS

| EP | 0 608 568 A | 8/1994 | |
|---|---|---|---|
| EP | 608568 * | 8/1994 | .................. 546/229 |
| EP | 0 611 003 A | 8/1994 | |
| EP | 0 714 883 A | 6/1996 | |
| FR | 2746395 * | 9/1997 | .................. 546/729 |
| FR | 2 746 395 A | 9/1997 | |
| WO | 96 04233 A | 2/1996 | |
| WO | 96 04234 A | 2/1996 | |
| WO | 98 41497 A | 9/1998 | |

OTHER PUBLICATIONS

Vejdelek et al, Chemical Abstract vol. 80 No. 36919X, 1973.*

Z. Vejdelek, et al., "Hypotensive derivative of 5–amino–6, 7,8,9–tetrahydro–5H–benzocycloheptene", CHEMICAL ABSTRACTS, vol. 80, No. 7, Feb. 18, 1974, Columbus Ohio, U.S., abstract No. 36919x, p. 279, column 2. (XP002108403 see abstract & CS 149 330 B(..) 15 Jun. 1973.

* cited by examiner

Primary Examiner—Alan L. Rotman
Assistant Examiner—Raymond Covington
(74) Attorney, Agent, or Firm—Oblon, Spivak, McClelland, Maier & Neustadt, P.C.

(57) ABSTRACT

Propanolamine derivatives represented by the following formula (I):

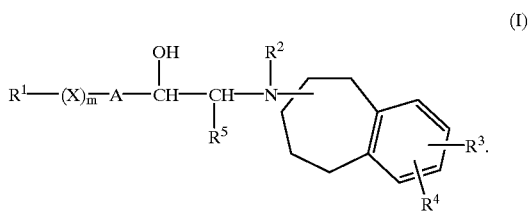

These derivatives may be $\beta_3$ agonists and exert sympathomimetic, anti-ulcerous, anti-pancreatitis, lipolytic and anti-urinary incontinence and anti-pollakiuria activities. Pharmaceutical compositions containing such propanolamine derivatives, methods for the prevention and/or treatment diseases using these propanolamine derivatives, and processes for their preparation are also described.

14 Claims, No Drawings

PROPANOLAMINE DERIVATIVES

TECHNICAL FIELD

This invention relates to new propanolamine derivatives which is the $\beta_3$ adrenergic receptor agonist and salts thereof which are useful as a medicament.

DISCLOSURE OF INVENTION

This invention relates to new propanolamine derivatives which is the $\beta_3$ adrenergic receptor agonist and salts thereof.

More particularly, it relates to new propanolamine derivatives and salts thereof which have gut selective sympathomimetic, anti-ulcerous, anti-pancreatitis, lipolytic, anti-urinary incontinence and anti-pollakiuria activities, to processes for the preparation thereof, to a pharmaceutical composition comprising the same and to a method of using the same therapeutically in the treatment and/or prevention of gastro-intestinal disorders caused by smooth muscle contractions in human beings or animals, and more particularly to a method for the treatment and/or prevention of spasm or hyperanakinesia in case of irritable bowel syndrome, gastritis, gastric ulcer, duodenal ulcer, enteritis, cholecystopathy, cholangitis, urinary calculus and the like; for the treatment and/or prevention of ulcer such as gastric ulcer, duodenal ulcer, peptic ulcer, ulcer caused by non steroidal anti-inflammatory drugs, or the like; for the treatment and/or prevention of dysuria such as pollakiuria, urinary incontinence or the like in case of nervous pollakiuria, neurogenic bladder dysfunction, nocturia, unstable bladder, cystospasm, chronic cystitis, chronic prostatitis, overflow incontinence, passive incontinence, reflux incontinence, urge incontinence, urinary stress incontinence or the like; and for the treatment and/or prevention of pancreatitis, obesity, diabetes, glycosuria, hyperlipidemia, hypertension, atherosclerosis, glaucoma, melancholia, depression and the like.

One object of this invention is to provide new and useful propanolamine derivatives and salts thereof which have gut selective sympathomimetic, anti-ulcerous, lipolytic, anti-urinary incontinence and anti-pollakiuria activities.

Another object of this invention is to provide processes for the preparation of said propanolamine derivatives and salts thereof.

A further object of this invention is to provide a pharmaceutical composition comprising, as an active ingredient, said propanolamine derivatives and salts thereof.

Still further object of this invention is to provide a therapeutical method for the treatment and/or prevention of aforesaid diseases in human beings or animals, using said propanolamine derivatives and salts thereof.

The object propanolamine derivatives of this invention are new and can be represented by the following general formula [I]:

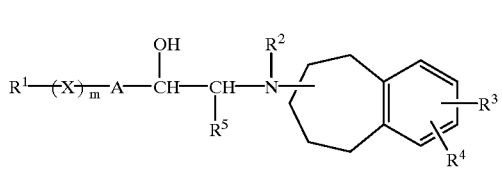

[I]

wherein
  $R^1$ is aryl which may have one or more suitable substituent(s), heterocyclic group or cyclo(lower)alkyl,
  $R^2$ is hydrogen or amino protective group,
  $R^3$ and $R^4$ are independently hydrogen, halogen, hydroxy, amino, nitro, carboxy, protected carboxy, aryl, lower alkyl, hydroxy(lower)alkyl, amino(lower)alkyl, acyloxy(lower)alkyl, acylamino(lower)alkyl, lower alkylamino(lower)alkyl which may have one or more suitable substituent(s), mono or di-(lower)alkylamino, acylamino, acyl group, lower alkoxy, halo(lower)alkoxy, lower alkenyloxy, lower alkoxy(lower)alkoxy, aryloxy, cyclo(lower)alkyloxy, heterocyclicoxy, ar(lower)alkyloxy, acyloxy or acyl(lower)alkoxy,
  $R^5$ is hydrogen, lower alkyl, or aryl,
  A is lower alkylene which may have one or more suitable substituent(s) or lower alkenylene,
  X is O, S, SO, $SO_2$ or NH, and
  m is an integer of 0 or 1.

The object compound [I] or a salt thereof can be prepared by the following processes.

Process 1

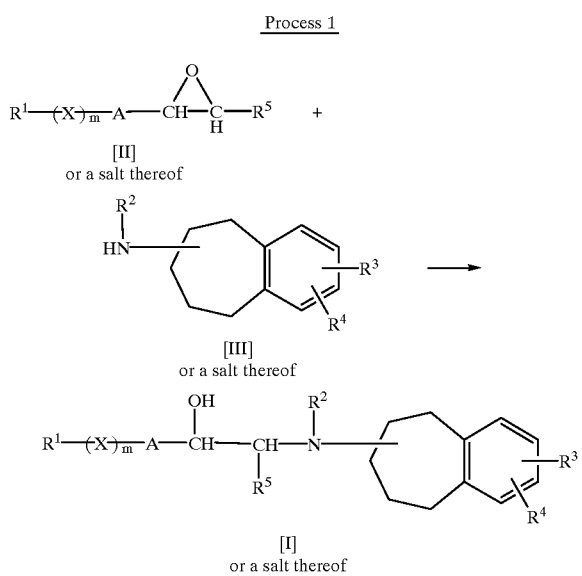

Process 2

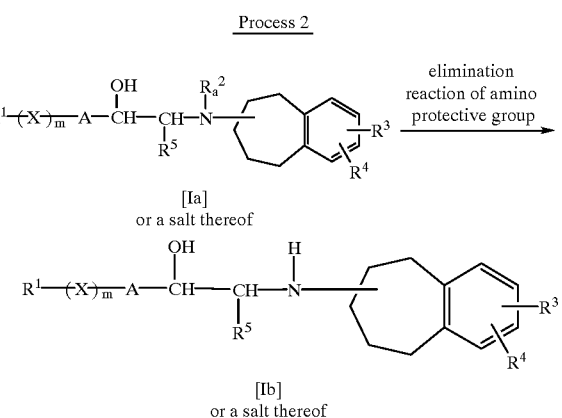

wherein
  $R^1$, $R^2$, $R^3$, $R^4$, $R^5$, A, X and m are each as defined above, and
  $R_a^2$ is amino protective group.

In the above and subsequent description of the present specification, suitable examples of the various definition to be included within the scope of the invention are explained in detail in the following.

The term "lower" is intended to mean a group having 1 to 6 carbon atom(s), unless otherwise provided.

The preferable number of the "one or more" in the term of "one or more suitable substituent(s)" may be 1 to 4.

Suitable example of "halogen" may be fluoro, chloro, bromo, iodo, and the like.

Suitable example of "lower alkyl" may include straight or branched one having 1 to 6 carbon atom(s), such as methyl, ethyl, propyl, isopropyl, butyl, isobutyl, sec-butyl, tert-butyl, pentyl, 1-methylpentyl, tert-pentyl, neo-pentyl, hexyl, isohexyl and the like.

Suitable example of "higher alkyl" may include straight or branched one having 7 to 20 carbon atoms, such as heptyl, octyl, 3,5-dimethyloctyl, 3,7-dimethyloctyl, nonyl, decyl, undecyl, dodecyl, tridecyl, tetradecyl, pentadecyl, hexadecyl, heptadecyl, octadecyl, nonadecyl, icosyl, and the like.

Suitable "lower alkoxy" and "lower alkoxy" moiety may be a straight or branched one such as methoxy, ethoxy, propoxy, isopropoxy, 1-ethylpropoxy, butoxy, sec-butoxy, tert-butoxy, pentyloxy, neopentyloxy, tert-pentyloxy, hexyloxy, and the like.

Suitable example of "aryl" and "ar" moiety may include phenyl which may have lower alkyl (e.g., phenyl, mesityl, tolyl, etc.), naphthyl, anthryl, and the like, in which the preferred one may be phenyl and naphthyl.

Suitable example of "aroyl" moiety may include benzoyl, toluoyl, naphthoyl, anthrylcarbonyl, and the like, in which the preferred one may be benzoyl and naphthoyl.

Suitable example of "protected carboxy" may be a conventional protecting group such as an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxyethyl ester, 2-propionyloxyethyl ester, hexanoyloxymethyl ester, etc.], lower alkanesulfonyl(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.];

higher alkyl ester [e.g. heptyl ester, octyl ester, 3,5-dimethyloctyl ester, 3,7-dimethyloctyl ester, nonyl ester, decyl ester, undecyl ester, dodecyl ester, tridecyl ester, tetradecyl ester, pentadecyl ester, hexadecyl ester, heptadecyl ester, octadecyl ester, nonadecyl ester, adamantyl ester, etc.];

lower alkenyl ester [e.g. ($C_2$–$C_6$)alkenyl ester (e.g. vinyl ester, allyl ester, etc.)];

lower alkynyl ester [e.g. ($C_2$–$C_6$)alkynyl ester (e.g. ethynyl ester, propynyl ester, etc.)];

ar(lower)alkyl ester which may have one or more suitable substituent(s) [e.g. phenyl(lower)alkyl ester which may have 1 to 4 lower alkoxy, halogen, nitro, hydroxy, lower alkyl, phenyl, or halo(lower)alkyl (e.g. benzyl ester, 4-methoxybenzyl ester, 4-chlorobenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, 4-trifluoromethylbenzyl ester, etc.)];

aryl ester which may have one or more suitable substituent (s) [e.g. phenyl ester which may have 1 to 4 lower alkyl, or halogen (e.g. phenyl ester, 4-chlorophenyl ester, tolyl ester, 4-tert-butylphenyl ester, xylyl ester, mesityl ester, cumenyl ester, etc.)];

cycloalkyloxycarbonyloxy(lower)alkyl ester which may have lower alkyl (e.g., cyclopentyloxycarbonyloxymethyl ester, cyclohexyloxycarbonyloxymethyl ester, cycloheptyloxycarbonyloxymethyl ester, 1-methylcyclohexyloxycarbonyloxymethyl ester, 1-(or 2-)[cyclopentyloxycarbonyloxy]ethyl ester, 1-(or 2-)[cyclohexyloxycarbonyloxy]ethyl ester, 1-(or 2-)-[cycloheptyloxycarbonyloxy]ethyl ester, etc.), etc.];

(5-(lower)alkyl-2-oxo-1,3-dioxol-4-yl)(lower)alkyl ester [e.g., (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)methyl ester, 1-(or 2-)(5-methyl-2-oxo-1,3-dioxol-4-yl)ethyl ester, 1-(or 2-)(5-ethyl-2-oxo-1,3-dioxol-4-yl)ethyl ester, 1-(or 2-)(5-propyl-2-oxo-1,3-dioxol-4-yl)ethyl ester, etc.]; or the like, in which the preferred one may be lower alkyl ester, lower alkanoyloxy(lower)alkyl ester, ar(lower)alkyl ester which may have one or more suitable substituent(s), cycloalkyloxycarbonyloxy(lower)alkyl ester which may have lower alkyl, higher alkyl ester, and [5-(lower)alkyl-2-oxo-1,3-dioxol-4-yl](lower)alkyl ester;

and the more preferred one may be methyl ester, ethyl ester, isobutyl ester, butyl ester, pentyl ester, hexyl ester, benzyl ester, 4-trifluoromethylbenzyl ester, 4-chlorobenzyl ester, adamantyl ester, (5-methyl-2-oxo-1,3-dioxol-4-yl)methyl ester, (1-cyclohexyloxycarbonyloxy)ethyl ester and pivaloyloxymethyl ester, and the like, in which the preferred one may be ($C_1$–$C_4$)alkyl ester, and the most preferred one may be ethyl ester.

Suitable "acyl group" and "acyl" moiety may include carbamoyl, sulfamoyl, sulfinamoyl, sulfenamoyl, aliphatic acyl group and acyl group containing an aromatic ring, which is referred to as aromatic acyl, or heterocyclic ring, which is referred to as heterocyclic acyl.

Suitable example of said acyl may be illustrated as follows :

carbamoyl; sulfamoyl; sulfinamoyl; sulfenamoyl; aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

cyclo(lower)alkylcarbonyl (e.g., cyclopropylcarbonyl, cyclobutylcarbonyl, cyclopentylcarbonyl, cyclohexylcarbonyl, etc.); protected carboxy such as commonly protected carboxy [e.g., esterified carboxy such as lower or higher alkoxycarbonyl (e.g., methoxycarbonyl, ethoxycarbonyl, propyloxycarbonyl, isopropyloxycarbonyl, t-butoxycarbonyl, t-pentyloxycarbonyl, heptyloxycarbonyl, etc.), etc.], or the like; lower alkylcarbamoyl (e.g., methylcarbamoyl, dimethylcarbamoyl, ethylcarbamoyl, propylcarbamoyl, butylcarbamoyl, pentylcarbamoyl, hexylcarbamoyl, etc.);

lower or higher alkylsulfonyl (e.g., methylsulfonyl, dimethylsulfonyl, ethylsulfonyl, etc.); lower or higher alkoxysulfonyl (e.g., methoxysulfonyl, ethoxysulfonyl, etc.);

di-(lower)alkoxyphosphoryl (e.g, dimethoxyphosphoryl, diethoxyphosphoryl, dipropoxyphosphoryl, dibutoxyphosphoryl, dipentyloxyphosphoryl, dihexyloxyphosphoryl, etc.), lower alkylsulfamoyl (e.g., methylsulfamoyl, dimethylsulfamoyl, ethylsulfamoyl, propylsulfamoyl, butylsulfamoyl, pentylsulfamoyl hexylsulfamoyl, etc.), aromatic acyl such as aroyl (e.g., benzoyl, toluoyl, naphthoyl, etc.);

ar(lower)alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl(lower)alkanoyl (e.g., naphthylacetyl, naphthylpropanoyl, naphthylbutanoyl, etc.), etc.];

ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower) alkenoyl (e.g., naphthylpropenoyl, naphthylbutenoyl, etc.), etc.];

ar(lower)alkoxycarbonyl [e.g., phenyl(lower) alkoxycarbonyl (e.g., benzyloxycarbonyl, etc.), etc.);

aryloxycarbonyl (e.g., phenoxycarbonyl, naphthyloxcarbonyl, etc.);

aryloxy(lower)alkanoyl (e.g., phenoxyacetyl, phenoxypropionyl, etc.);

arylcarbamoyl (e.g., phenylcarbamoyl, etc.);

arylthiocarbamoyl (e.g., phenylthiocarbamoyl, etc.); arylglyoxyloyl (e.g., phenylglyoxyloyl, naphthylglyoxyloyl, etc.); arylsulfonyl (e.g., phenylsulfonyl, p-tolylsulfonyl, etc.); or the like.

heterocyclic acyl such as heterocycliccarbonyl;

heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexanoyl, etc.); heterocyclicglyoxyloyl;

or the like; and the like.

Suitable example of "heterocyclic group" and "heterocyclic" moiety may include unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1, 2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, dihydroindolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s) for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholino, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2, 3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, imidazothiadiazolyl, etc.;

unsaturated 3 to 8-membered (more preferably 5 or 6-membered) heteromonocyclic group containing an oxygen atom, for example, furyl, etc.;

saturated 3 to 8-membered (more preferably 5 or 6-membered) heteromonocyclic group containing an oxygen atom, for example, tetrahydrofuran, tetrahydropyran, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like, and the abovementioned "heterocyclic group" and "heterocyclic" moiety may have one or more suitable substituent(s) such as amino, oxo, cyano, aryl, ar(lower)alkyl, heterocyclc group.

Suitable example of "cyclo(lower)alkyl" may include cyclopropyl, cyclobutyl, cyclopentyl, cyclohexyl, and the like, in which the preferred one may be cyclo($C_4$–$C_6$)alkyl, and the most preferred one may be cyclopentyl and cyclohexyl.

Suitable example of "amino protective group" moiety may be common amino protective group such as acyl, for example, substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.], substituted or unsubstituted aralkyloxycarbonyl [e.g. benzyloxycarbonyl, p-nitrobenzyloxycarbonyl, etc.], substituted or unsubstituted arenesulfonyl [e.g. benzenesulfonyl, tosyl, etc.], nitrophenylsulfenyl, ar(lower)alkyl [e.g. trityl, benzyl, etc.], and the like, in which preferable one may be lower alkoxycarbonyl and phenyl(lower)alkyl, and the most preferred one may be tert-butoxycarbonyl and benzyl.

Suitable example of "aryl" moiety in the term of "aryl which may have one or more suitable substituent(s)" in $R^1$ can be referred to aforementioned "aryl", in which the preferred one may be phenyl.

Suitable example of "suitable substituent(s)" moiety in the term of "aryl which may have one or more suitable substituent(s)" may include hydroxy, halogen, lower alkylsulfonylamino, lower alkanoylamino, and the like.

Suitable example of "lower alkylsulfonylamino" may include methylsulfonylamino, ethylsulfonylamino, propylsulfonylamino, butylsulfonylamino, pentylsulfonylamino, hexylsulfonylamino, and the like, in which the preferred one may be ($C_1$–$C_4$)alkylsulfonylamino, and the most preferred one may be methylsulfonylamino.

Suitable example of "lower alkanoylamino" may include formylamino, acetylamino, propanoylamino, butanoylamino, 2-methylpropanoylamino, pentanoylamino, hexanoylamino, and the like, in which the preferred one may be ($C_1$–$C_4$)-alkanoylamino, and the most preferred one may be acetylamino.

Suitable example of "heterocyclic group" in $R^1$ can be referred to aforementioned "heterocyclic group", in which the preferred one may be unsaturated 3 to 8-membered heteromonocyclic group containing 1 to 4 nitrogen atom(s) which may have one or more suitable substituent(s), and unsaturated condensed heterocyclic group containing 1 to 4 nitrogen atom(s) which may have one or more suitable substituent(s), and the most preferred one may be pyridyl, aminopyridyl, indolyl and benzimidazolone.

Suitable example of "cyclo(lower)alkyl" in $R^1$ can be referred to aforementioned "cyclo(lower)alkyl", in which the preferred one may be cyclo($C_4$–$C_6$)alkyl, and the most preferred one may be cyclopentyl.

Suitable example of "mono or di lower alkylamino" may include methylamino, dimethylamino, ethylamino, diethylamino, propylamino, isopropylamino, butylamino, methylbutylamino, sec-butylamino, 1-methylpentylamino, ethylpentylamino, hexylamino, and the like, in which the preferred one may be mono or di($C_{1-4}$)alkylamino, and the most preferred one may be dimethylamino.

Suitable example of "hydroxy(lower)alkyl" may include hydroxymethyl, hydroxyethyl, hydroxypropyl, hydroxybutyl, hydroxypentyl, hydroxyhexyl, and the like, in which the preferred one may be hydroxy($C_1$–$C_4$)alkyl, and the most preferred one may be hydroxymethyl.

Suitable example of "amino(lower)alkyl" may include aminomethyl, aminoethyl, aminopropyl, aminobutyl, aminopentyl, aminohexyl, and the like, in which the preferred one may be amino($C_1$–$C_4$)alkyl, and the most preferred one may be aminomethyl.

Suitable example of "acyl" moiety in the term of "acyloxy (lower)alkyl" can be referred to aforementioned "acyl", in which the preferred one may be lower alkanoyl, and the most preferred one may be acetyl.

Suitable example of "acyloxy(lower)alkyl" may include lower alkanoyloxy(lower)alkyl, in which the preferred one may be ($C_1$–$C_4$)alkanoyloxy($C_1$–$C_4$)alkyl, and the most preferred one may be acetyloxymethyl.

Suitable example of "acyl" moiety in the term of "acylamino(lower)alkyl" can be referred to aforementioned "acyl", in which the preferred one may be lower alkanoyl, aroyl, carbamoyl, lower alkylcarbamoyl, lower alkylsulfonyl, and arylsulfonyl.

Suitable example of "acylamino(lower)alkyl" may include lower alkanoylamino(lower)alkyl, aroylamino (lower)alkyl, carbamoylamino(lower)alkyl, lower alkylcarbamoylamino(lower)alkyl, lower alkylsulfonylamino(lower)alkyl, arylsulfonylamino(lower) alkyl and the like, in which the preferred one may be ($C_1$–$C_4$)alkanoylamino($C_1$–$C_4$)alkyl, benzoylamino($C_1$–$C_4$) alkyl, carbamoylamino($C_1$–$C_4$)alkyl, ($C_1$–$C_4$) alkylsulfonylamino($C_1$–$C_4$)alkyl and phenylsulfonylamino ($C_1$–$C_4$)alkyl, and the most referred one may be acetylaminomethyl, benzoylaminomethyl, carbamoylaminomethyl, butylcarbamoylaminomethyl, methylsulfonylaminomethyl and phenylsulfonylaminomethyl.

Suitable example of "suitable substituent" moiety in the term of "lower alkylamino(lower)alkyl which may have one or more suitable substituent(s)" may include lower alkyl and carboxy, in which the preferred one may be methyl and carboxy.

Suitable example of "lower alkylamino(lower)alkyl which may have one or more suitable substituent(s)" may include di(lower)alkylamino(lower)alkyl, carboxy(lower) alkylamino(lower)alkyl, and the like, in which the preferred one may be di($C_1$–$C_4$)alkylamino($C_1$–$C_4$)alkyl and carboxy ($C_1$–$C_4$)-alkylamino($C_1$–$C_4$)alkyl, and the most preferred one may be dimethylaminomethyl and carboxyethylaminomethyl.

Suitable example of "acyl" moiety in the term of "acylamino" can be referred to aforementioned "acyl" moiety, in which the preferred one may be lower alkanoyl, aroyl, lower alkoxycarbonyl, aryloxycarbonyl, lower alkylsulfonyl, phenylsulfonyl, sulfamoyl, lower alkylsulfamoyl, and the most preferred one may be acetyl, benzoyl, methoxycarbonyl, phenoxycarbonyl, methylsulfonyl, phenylsulfonyl, sulfamoyl and dimethylsulfamoyl.

Suitable example of "acylamino" may be acetylamino, benzoylamino, methoxycarbonylamino, phenoxycarbonylamino, methylsulfonylamino, phenylsulfonylamino, sulfamoylamino and dimethylsulfamoylamino.

Suitable example of "acyl group" can be referred to aforementioned "acyl group", in which the preferred one may be carbamoyl, lower alkylcarbamoyl, arylcarbamoyl, and the most preferred one may be carbamoy, methylcarbamoyl, dimethylcarbamoyl and phenylcarbamoyl.

Suitable example of "lower. alkoxy" can be referred to aforementioned "lower alkoxy", in which the preferred one may be methoxy, ethoxy, propoxy, isopropoxy and benzyloxy.

Suitable example of "halo(lower)alkoxy" may be fluoro (lower)alkoxy, chloro(lower)alkoxy, bromo(lower)alkoxy, iodo(lower)alkoxy, and the like, in which the preferred one may be fluoro($C_1$–$C_4$)alkoxy, chloro($C_1$–$C_4$)alkoxy, bromo ($C_1$–$C_4$)alkoxy, iodo($C_1$–$C_4$)alkoxy, and the most preferred one may be fluoromethoxy.

Suitable example of "lower alkenyloxy" may include vinyloxy, 1-(or 2-)propenyloxy, 1-(or 2- or 3-)butenyloxy, 1-(or 2- or 3- or 4-)pentenyloxy, 1-(or 2- or 3- or 4- or 5-)hexenyloxy, and the like, in which the preferred one may be ($C_2$–$C_4$)alkenyloxy, and the most preferred one may be 2-propenyloxy.

Suitable example of "lower alkoxy(lower)alkoxy" may include methoxymethoxy, methoxyethoxy, methoxypropoxy, ethoxypropoxy, ethoxyethoxy, propoxymethoxy, butoxymethoxy, pentyloxymethoxy, hexyloxymethoxy, hexyloxyethoxy, and the like, in which the preferred one may be ($C_1$–$C_4$)alkoxy-($C_1$–$C_4$)alkoxy, and the most preferred one may be methoxyethoxy.

Suitable example of "aryloxy" may include phenoxy, mesityloxy, tolyloxy, naphthyloxy, anthryloxy, and the like, in which the preferred one may be phenoxy.

Suitable example of "cyclo(lower)alkyloxy" may include cyclopropyloxy, cyclobutyloxy, cyclopentyloxy, cyclohexyloxy, and the like, in which the preferred one may be cyclopentyloxy.

Suitable example of "heterocyclic" moiety in the term of "heterocyclicoxy" can be referred to aforementioned "heterocyclic" moiety, in which the preferred one may be unsaturated 3 to 8-membered heteromonocyclic group containing 1 to 4 nitrogen atoms(s) which may have a suitable substituent, and the most preferred one may be pyridyl having cyano.

Suitable example of "heterocyclicoxy" may be pyridyloxy having cyano.

Suitable example of "ar(lower)alkyloxy" may include phenyl(lower)alkyloxy, mesityl(lower)alkyloxy, tolyl(lower)alkyloxy, naphthyl(lower)alkyloxy, anthryl(lower)alkyloxy, and the like, in which the preferred one may be phenyl($C_1$–$C_4$)alkyloxy, and the most preferred one may be benzyloxy and phenetyloxy.

Suitable example of "acyl" moiety in the term of "acyloxy" can be referred to aforementioned "acyl" moiety, in which the preferred one may be carbamoyl and mono or di-lower alkylsulfamoyl, and the most preferred one may be carbamoyl and dimethylsulfamoyl.

Suitable example of "acyloxy" may be carbamoyloxy and mono or di lower alkylsulfamoyloxy and the most preferred one may be carbamoyloxy and dimethylsulfamoyloxy.

Suitable example of "lower alkoxy" moiety in the term of "acyl(lower)alkoxy" can be referred to aforementioned "lower alkoxy", in which the preferred one may be ($C_1$–$C_4$) alkoxy, and the most preferred one may be methoxy.

Suitable example of "acyl" moiety in the term of "acyl (lower)alkoxy" may include the aforementioned "acyl" moiety; lower alkylcarbamoyl which may have one or more suitable substituent(s) selected from the group consisting of hydroxy, lower alkoxy, lower alkyl, ar(lower)alkyl, protected carboxy, carboxy, mono or di lower alkylamino, lower alkylthio, halo(lower)alkyl, aryl which may have one or more suitable substituent(s), and heterocyclic group; arylcarbamoyl which may have one or more suitable substituent(s) selected from the group consisting of lower alkyl, higher alkyl, halogen, halo(lower)alkyl, mono or di-lower alkylamino, lower alkoxy, halo(lower)alkoxy and nitro; heterocycliccarbamoyl which may have one or more suitable substituent(s) selected from the group consisting of ar(lower)alkyl, aryl and heterocyclic(lower)alkyl which may be substituted with heterocyclic group; heterocycliccarbonyl which may have one or more suitable substituent(s) selected from the group consisting of ar(lower)alkyl and heterocyclic group which may be substituted with one or more suitable substituent(s); cyclo(lower)alkylcarbamoyl;guanidinocarbonyl; and the like.

Suitable example of "lower alkylcarbamoyl" may include methylcarbamoyl, ethylcarbamoyl, propylcarbamoyl, isopropylcarbamoyl, butylcarbamoyl, 1-methylbutylcarbamoyl, isobutylcarbamoyl, sec-butylcarbamoyl, tert-butylcarbamoyl, pentylcarbamoyl, isopentylcarbamoyl, tert-pentylcarbamoyl, 1-methylpentylcarbamoyl, neopentylcarbamoyl, hexylcarbamoyl, isohexylcarbamoyl, and the like, in which the preferred one may be methylcarbamoyl, ethylcarbamoyl, propylcarbamoyl, butylcarbamoyl, sec-butylcarbamoyl, isobutylcarbamoyl, 1-methylbutylcarbamoyl, and hexylcarbamoyl.

Suitable example of "lower alkoxy" in the suitable substituent(s) of the term "lower alkylcarbamoyl which may have one or more suitable substituent(s)" can be referred to aforementioned "lower alkoxy", in which the preferred one may be ($C_1$–$C_4$)alkoxy, and the most preferred one may be methoxy, ethoxy and propoxy.

Suitable example of "lower alkyl" in the suitable substituent(s) of the term "lower alkylcarbamoyl which may nave one or more suitable substituent(s)" can be referred to aforementioned "lower alkyl", in which the preferred one may be ($C_1$–$C_4$)alkyl, and the most preferred one may be methyl and ethyl.

Suitable example of "ar(lower)alkyl" in the suitable substituent(s) of the term "lower alkylcarbamoyl which may have one or more suitable substituent(s)" may include "mono- or di- or tri-phenyl(lower)alkyl" such as benzyl, phenethyl, phenylpropyl, phenylbutyl, phenylpentyl, phenylhexyl, benzhydryl, trityl, and the like, in which the preferred one may be benzyl.

Suitable example of "protected carboxy" in the suitable substituent(s) of the term "lower alkylcarbamoyl which may have one or more suitable substituent(s)" can be referred to aforementioned "protected carboxy", in which the preferred one may be ($C_1$–$C_4$)alkyl ester, and the most preferred one may be ethyl ester.

Suitable example of "mono or di-lower alkylamino" in the suitable substituent(s) of the term "lower alkylcarbamoyl which may have one or more suitable substituent(s)" may include methylamino, dimethylamino, ethylamino, diethylamino, propylamino, isopropylamino, butylamino, isobutylamino, sec-butylamino, tert-butylamino, pentylamino, isopentylamino, tert-pentylamino, 1-methylpentylamino, neopentylamino, hexylamino, isohexylamino, and the like, in which the preferred one may be di($C_1$–$C_4$)alkylamino, and the most preferred one may be dimethylamino and diethylamino.

Suitable example of "lower alkylthio" in the suitable substituent(s) of the term "lower alkylcarbamoyl which may have one or more suitable substituent(s)" may include methylthio, ethylthio, propylthio, butylthio, pentylthio, and the like, in which the preferred one may be ($C_1$–$C_4$) alkylthio, and the most preferred one may be methylthio.

Suitable example of "halo(lower)alkyl" in the suitable substituent(s) of the term "lower alkylcarbamoyl which may have one or more suitable substituent(s)" may include tri-halo(lower)alkyl such as trichloromethyl, trichloroethyl, trichloropropyl, trifluoromethyl, trifluoroethyl, trifluoropropyl, tribromomethyl, tribromoethyl, and the like, in which the preferred one may be tri-halo($C_1$–$C_4$)alkyl, and the most preferred one may be trifluoromethyl and trifluoroethyl.

Suitable example of "aryl" in the term of "aryl which may have one or more suitable substituent(s)" can be referred to aforementioned "aryl", in which the preferred one may be phenyl.

Suitable example of "suitable substituent(s)" in the term of "aryl which may have one or more suitable substituent(s)" may include mono or di(lower)alkylamino(lower)alkyl (e.g., methylaminomethyl, dimethylaminomethyl, dimethylaminoethyl, diethylaminoethyl, dimethylaminopropyl, propylaminopropyl, butylaminoethyl, diethylaminopentyl, etc.), in which the preferred one may be mono or di($C_1$–$C_4$)alkylamino($C_1$–$C_4$) alkyl, and the most preferred one may be dimethylaminomethyl.

Suitable example of "heterocyclic group" can be referred to aforementioned "heterocyclic group", in which the preferred one may be saturated or unsaturated 3 to 8-membered heteromonocyclic group containing 1 to 4 nitrogen atom(s) and saturated 3 to 8-membered heteromonocyclic group containing 1 to 2 oxygen atom(s) and 1 to 3 nitrogen atom(s), and the most preferred one may be pyridyl, imidazolyl and morpholino.

Suitable example of "aryl" moiety in the term of "arylcarbamoyl which may have one or more suitable substituent(s)" can be referred to aforementioned "aryl", in which the preferred one may be phenyl.

Suitable example of "lower alkyl" in the suitable substituent(s) of the term "arylcarbamoyl which may have one or more suitable substituent(s)" can be referred to aforementioned "lower alkyl", in which the preferred one may be (C₁–C₄)alkyl, and the most preferred one may be methyl and butyl.

Suitable example of "higher alkyl" in the suitable substituent(s) of the term "arylcarbamoyl which may have one or more suitable substituent(s)" can be referred to aforementioned "higher alkyl", in which the preferred one may be (C₇–C₁₀)alkyl, and the most preferred one may be octyl.

Suitable example of "halo(lower)alkyl" in the suitable substituent(s) of the term "arylcarbamoyl which may have one or more suitable substituent(s)" may include tri-halo (lower)alkyl such as trichloromethyl, trichloroethyl, trichloropropyl, trifluoromethyl, trifluoroethyl, trifluoropropyl, tribromomethyl, tribromoethyl, and the like, in which the preferred one may be tri-halo(C₁–C₄)alkyl, and the most preferred one may be trifluoromethyl.

Suitable example of "mono or di-lower alkylamino" in the suitable substituent(s) of the term "arylcarbamoyl which may have one or more suitable substituent(s)" may include methylamino, dimethylamino, ethylamino, diethylamino, propylamino, isopropylamino, butylamino, isobutylamino, sec-butylamino, tert-butylamino, pentylamino, isopentylamino, tert-pentylamino, 1-methylpentylamino, neopentylamino, hexylamino, isohexylamino, and the like, in which the preferred one may be di(C₁–C₄)alkylamino, and the most preferred one may be dimethylamino.

Suitable example of "lower alkoxy" in the suitable substituent(s) of the term "arylcarbamoyl which may have one or more suitable substituent(s)" can be referred to aforementioned "lower alkoxy", in which the preferred one may be (C₁–C₄)alkoxy, and the most preferred one may be methoxy.

Suitable example of "halo(lower)alkoxy" in the suitable substituent(s) of the term "arylcarbamoyl which may have one or more suitable substituent(s)" may include fluoromethoxy, fluoroethoxy, trifluoromethoxy, chloromethoxy, chloroethoxy, trichloroethoxy, bromomethoxy, iodoethoxy, and the like, in which the preferred one may be halo(C₁–C₄)alkoxy, and the most preferred one may be fluoromethoxy.

Suitable example of "heterocyclic" moiety in the term of "heterocyclicarbamoyl which may have one or more suitable substituent(s)" can be referred to aforementioned "heterocyclic" moiety, in which the preferred one may be saturated or unsaturated 3 to 8-membered heteromonocyclic group containing 1 to 4 nitrogen atom(s), unsaturated condensed heterocyclic group containing 1 to 4 nitrogen atom(s) and unsaturated 3 to 8-membered heteromonocyclic group containing 1 to 2 sulfur atom(s) and 1 to 3 nitrogen atom(s), and the most preferred one may be piperidyl, tetrazolyl, indolyl and thiazolyl.

Suitable example of "ar(lower)alkyl" in the suitable substituent(s) of the term "heterocycliccarbamoyl which may have one or more suitable substituent(s)" may include "mono- or di- or tri-phenyl(lower)alkyl" such as benzyl, phenethyl, phenylpropyl, phenylbutyl, phenylpentyl, phenylhexyl, benzhydryl, trityl, and the like, in which the preferred one may be benzyl.

Suitable example of "lower alkyl" moiety in the term of "heterocyclic(lower)alkyl" in the suitable substituent(s) of the term "heterocycliccarbamoyl which may have one or more suitable substituent(s)" can be referred to aforementioned "lower alkyl", in which the preferred one may be (C₁–C₄)alkyl, and the most preferred one may be methyl.

Suitable example of "heterocyclic" moiety in the term of "heterocyclic(lower)alkyl" in the suitable substituent(s) of the term "heterocycliccarbamoyl which may have one or more suitable substituent(s)" can be referred to aforementioned "heterocyclic", in which the preferred one may be saturated 3 to 8-membered heteromonocyclic group containing 1 to 4 nitrogen atom(s), and the most preferred one may be piperidyl.

Suitable example of "heterocyclic group" in the term of "heterocyclic(lower)alkyl which may be substituted with heterocyclic group" in the suitable substituent(s) of the term "heterocycliccarbamoyl which may have one or more suitable substituent(s)" can be referred to aforementioned "heterocyclic group", in which the preferred one may be unsaturated condensed heterocyclic group containing 1 to 4 nitrogen atom(s), and the most preferred one may be indolyl.

Suitable example of "heterocyclic" moiety in the term of "heterocycliccarbonyl which may have one or more suitable substituent(s)" can be referred to aforementioned "heterocyclic" moiety, in which the preferred one may be saturated 3 to 8-membered heteromonocyclic group containing to 4 nitrogen atom(s) and unsaturated condensed heterocyclic group containing 1 to 4 nitrogen atom(s), and the most preferred one may be piperidyl, piperazinyl and dihydroindolyl.

Suitable example of "ar(lower)alkyl" in the suitable substituent(s) of the term "heterocycliccarbonyl which may have one or more suitable substituent(s)" may include "mono- or di- or tri-phenyl(lower)alkyl" such as benzyl, phenethyl, phenylpropyl, phenylbutyl, phenylpentyl, phenylhexyl, benzhydryl, trityl, and the like, in which the preferred one may be benzhydryl.

Suitable example of "heterocyclic group" moiety in the term "heterocyclic group which may have one or more suitable substituent(s)" in the suitable substituent(s) of the term "heterocycliccarbonyl which may have one or more suitable substituent(s)" can be referred to aforementioned "heterocyclic group", in which the preferred one may be unsaturated 3 to 8-membered heteromonocyclic group containing 1 to 4 nitrogen atom(s), and the most preferred one may be pyridazinyl.

Suitable example of "suitable substituent(s)" in the term of "heterocyclic group which may be substituted with one or more suitable substituent(s)" may include oxo and aryl, in which the preferred one may be oxo and phenyl.

Suitable example of "cyclo(lower)alkylcarbamoyl" may include cyclopropylcarbamoyl, cyclobutylcarbamoyl, cyclopentylcarbamoyl, cyclohexylcarbamoyl, and the like, in which the preferred one may be cyclo(C₄–C₆) alkylcarbamoyl, and the most preferred one may be cyclohexylcarbamoyl.

Suitable example of "lower alkyl" in R⁵ can be referred to aforementioned "lower alkyl", in which the preferred one may be (C₁–C₄)alkyl, and the most preferred one may be methyl.

Suitable example of "acyl(lower)alkoxy" may include carbamoyl(lower)alkoxy, lower alkylcarbamoyl(lower) alkoxy, cyclo(lower)alkylcarbamoyl(lower)alkoxy, arylcarbamoyl(lower)alkoxy, heterocycliccarbamoyl (lower)alkoxy, N-lower alkyl-lower alkylcarbamoyl(lower) alkoxy, ar(lower)alkylcarbamoyl(lower)alkoxy, lower alkoxy(lower)alkylcarbamoyl(lower)alkoxy, lower alkylthio (lower)alkylcarbamoyl(lower)alkoxy, di(lower)alkylamino (lower)alkylcarbamoyl(lower)alkoxy, heterocycliccarbonyl (lower)alkoxy, guanidinocarbonyl(lower)alkoxy, hydroxy (lower)alkylcarbamoyl(lower)alkoxy, halo(lower) alkylcarbamoyl(lower)alkoxy, protected carboxy(lower) alkylcarbamoyl(lower)alkoxy having protected carboxy, heterocyclic(lower)alkylcarbamoyl(lower)alkoxy, heterocycliccarbamoyl(lower)alkoxy having aryl(lower)

alkyl, arylcarbamoyl(lower)alkoxy having higher alkyl, arylcarbamoyl(lower)alkoxy having lower alkyl, arylcarbamoyl(lower)alkoxy having halo(lower)alkyl, arylcarbamoyl(lower)alkoxy having nitro, arylcarbamoyl (lower)alkoxy having halogen, arylcarbamoyl(lower)alkoxy having di(lower)alkylamino(lower)alkyl, heterocycliccarbonyl(lower)alkoxy having benzhydryl, lower alkylcarbamoyl(lower)alkoxy having benzhydryl, heterocycliccarbamoyl(lower)alkoxy having heterocyclic (lower)alkyl substituted with heterocyclic group, heterocycliccarbonyl(lower)alkoxy having heterocyclic group substituted with oxo and aryl, N-lower alkyl-ar(lower) alkylcarbamoyl(lower)alkoxy, N-ar(lower)alkyl-ar(lower) alkylcarbamoyl(lower)alkoxy, N-lower alkyl-heterocyclic (lower)alkylcarbamoyl(lower)alkoxy, arylcarbamoly(lower) alkoxy having lower alkyl, arylcarbamoyl(lower)alkoxy having lower alkoxy, arylcarbamoyl(lower)alkoxy having halogen, arylcarbamoyl(lower)alkoxy having halo(lower) alkoxy, arylcarbamoyl(lower)alkoxy having di(lower) alkylamino, N-aryl-aryl(lower)alkylcarbamoyl(lower) alkoxy, N-lower alkyl-cyclo(lower)alkylcarbamoyl(lower) alkoxy, in which the preferred one may be carbamoyl($C_1$–$C_4$)- alkoxy, ($C_1$–$C_6$)alkylcarbamoyl($C_1$–$C_4$)alkoxy, cyclo ($C_4$–$C_6$)-alkylcarbamoyl($C_1$–$C_4$)alkoxy, phenylcarbamoyl($C_1$–$C_4$)alkoxy, carbamoyl($C_1$–$C_4$) alkoxy substituted with unsaturated 3 to 8-membered heteromonocyclic group containing 1 to 4 nitrogen atom(s), carbamoyl($C_1$–$C_4$)alkoxy substituted with unsaturated condensed heterocyclic group containing 1 to 4 nitrogen atom(s), N-($C_1$–$C_4$)alkyl-($C_1$–$C_6$) alkylcarbamoyl($C_1$–$C_4$)alkoxy, phenyl($C_1$–$C_4$) alkylcarbamoyl ($C_1$–$C_4$)alkoxy, ($C_1$–$C_4$)alkoxy ($C_1$–$C_4$)alkylcarbamoyl($C_1$–$C_4$)alkoxy, ($C_1$–$C_4$) alkylthio($C_1$–$C_4$)alkylcarbamoyl($C_1$–$C_4$)alkoxy, di($C_1$–$C_4$)alkylamino($C_1$–$C_4$)alkylcarbamoyl($C_1$–$C_4$) alkoxy, carbonyl(lower)alkoxy substituted with saturated 3 to 8-membered heteromonocyclic group containing 1 to 4 nitrogen atom(s), guanidinocarbamoyl ($C_1$–$C_4$)alkoxy, hydroxy($C_1$–$C_4$)alkylcarbamoyl ($C_1$–$C_4$)alkoxy, tri-halo($C_1$–$C_4$)alkylcarbamoyl ($C_1$–$C_4$)alkoxy, esterified carboxy($C_1$–$C_4$) alkylcarbamoyl($C_1$–$C_4$)alkoxy having esterified carboxy, ($C_1$–$C_4$)alkylcarbamoyl($C_1$–$C_4$)alkoxy substituted with saturated 3 to 8-membered heteromonocyclic group containing 1 to 2 oxygen atom(s) and 1 to 3 nitrogen atom(s), ($C_1$–$C_4$)alkylcarbamoyl($C_1$–$C_4$) alkoxy substituted with unsaturated 3 to 8-membered heteromonocyclic group containing 1 to 4 nitrogen atom(s), carbamoyl($C_1$–$C_4$)alkoxy substituted with saturated 3 to 8-membered heteromonocyclic group containing 1 to 4 nitrogen atom(s) having aryl(lower) alkyl, phenylcarbamoyl($C_1$–$C_4$)alkoxy having ($C_7$–$C_{14}$)alkyl, phenylcarbamoyl($C_1$–$C_4$)alkoxy having ($C_1$–$C_4$)alkyl, phenylcarbamoyl($C_1$–$C_4$)alkoxy having tri-halo($C_1$–$C_4$)alkyl, phenylcarbamoyl($C_1$–$C_4$)alkoxy having nitro, phenylcarbamoyl($C_1$–$C_4$)alkoxy having halogen, phenylcarbamoyl($C_1$–$C_4$)alkoxy having di($C_1$–$C_4$)alkylamino-($C_1$–$C_4$)alkyl, carbonyl($C_1$–$C_4$) alkoxy substituted with saturated 3 to 8-membered heteromonocyclic group containing 1 to 4 nitrogen atom(s) having benzhydryl, ($C_1$–$C_4$)alkyl-carbamoyl ($C_1$–$C_4$)alkoxy having benzhydryl, carbamoyl($C_1$–$C_4$)- alkoxy substituted with unsaturated 3 to 8-membered heteromonocyclic group containing 1 to 2 sulfur atom (s) and 1 to 3 nitrogen atom(s) having ($C_1$–$C_4$)alkyl substituted with saturated 3 to 8-membered hetero- monocyclic group containing 1 to 4 nitrogen atom(s) substituted with unsaturated condensed heterocyclic group containing 1 to 4 nitrogen atom(s), carbonyl ($C_1$–$C_4$)alkoxy having unsaturated 3 to 8-membered heteromonocyclic group containing 1 to 4 nitrogen atom(s) substituted with oxo and phenyl, N-($C_1$–$C_4$) alkyl-phenyl-($C_1$–$C_4$)alkylcarbamoyl($C_1$–$C_4$)alkoxy, N-phenyl($C_1$–$C_4$)alkyl-phenyl($C_1$–$C_4$)alkylcarbamoyl ($C_1$–$C_4$)alkoxy, N-($C_1$–$C_4$)alkyl-($C_1$–$C_4$) alkylcarbamoyl($C_1$–$C_4$)alkoxy having unsaturated 3 to 8-membered heteromonocyclic group containing 1 to 4 nitrogen atom(s), N-($C_1$–$C_4$)alkyl-($C_1$–$C_4$) alkylcarbamoyl($C_1$–$C_4$)alkoxy having unsaturated condensed heterocyclic group containing 1 to 4 nitrogen atom(s), phenylcarbamoyl($C_1$–$C_4$)alkoxy having ($C_1$–$C_4$)alkyl, phenylcarbamoyl($C_1$–$C_4$)alkoxy having ($C_1$–$C_4$)alkoxy, phenylcarbamoyl($C_1$–$C_4$)alkoxy having halogen, carbamoyl($C_1$–$C_4$)alkoxy having unsaturated 3 to 8-membered heteromonocyclic group containing 1 to 2 sulfur atom(s) and 1 to 3 nitrogen atom(s), carbonyl($C_1$–$C_4$)alkoxy substituted with unsaturated condensed heterocyclic group containing 1 to 4 nitrogen atom(s), phenylcarbamoyl ($C_1$–$C_4$)alkoxy having di-halo($C_1$–$C_4$)alkoxy, phenylcarbamoyl($C_1$–$C_4$) alkoxy having di($C_1$–$C_4$)alkylamino, N-phenyl-phenyl ($C_1$–$C_4$)alkylcarbamoyl($C_1$–$C_4$)alkoxy, N-($C_1$–$C_4$) alkyl-cyclo($C_4$–$C_6$)alkylcarbamoyl($C_1$–$C_4$)alkoxy, and the most preferred one may be carbamoylmethoxy, ethylcarbamoylmethoxy, sec-butylcarbamoylmethoxy, n-butylcarbamoylmethoxy, hexylcarbamoylmethoxy, cyclohexylcarbamoylmethoxy, phenylcarbamoylmethoxy, tetrazolylcarbamoylmethoxy, indolylcarbamoylmethoxy, N-methyl-methylcarbamoylmethoxy, N-methyl-butylcarbamoylmethoxy, benzylcarbamoylmethoxy, methoxyethylcarbamoylmethoxy, methylthioethylcarbamoylmethoxy, dimethylaminoethylcarbamoylmethoxy, piperidinocarbonylmethoxy, guanidinocarbonylmethoxy, hydroxybutylcarbamoylmethoxy, 1-methylbutylcarbamoylmethoxy, 2-hydroxypropylcarbamoylmethoxy, ethoxypropylcarbamoylmethoxy, hydroxypropylcarbamoylmethoxy, diethylaminopropylcarbamoylmethoxy, tri-fluoroethylcarbamoylmethoxy, 1-ethoxycarbonyl-ethoxycarbonylmethylcarbamoylmethoxy, morpholinoethylcarbamoylmethoxy, pyridylethylcarbamoylmethoxy, pyridylmethylcarbamoylmethoxy, imidazolylpropylcarbamoylmethoxy, phenylbutylcarbamoylmethoxy, carbamoylmethoxy having piperidyl substituted with benzyl, octylphenylcarbamoylmethoxy, butylphenylcarbamoylmethoxy, tri-fluoromethylphenylcarbamoylmethoxy, nitrophenylcarbamoylmethoxy, fluorophenylcarbamoylmethoxy, dimethylaminomethylbenzylcarbamoylmethoxy, piperadinocarbonylmethoxy substituted with benzhydryl, benzhydrylmethylcarbamoylmethoxy, carbamoyl-methoxy having thiazolyl having piperidinomethyl substituted with indolyl, piperidinocarbonylmethoxy having piridazinyl substituted with phenyl and oxo, N-methyl-benzylcarbamoylmethoxy, N-benzylbenzylcarbamoylmethoxy, N-methoxyindolylethylcarbamoylmethoxy, N-methylpyridylethylcarbamoylmethoxy, tolylcarbamoylmethoxy, methoxyphenylcarbamoylmethoxy, chlorophenylcarbamoylmethoxy, thiazolylcarbamoylmethoxy, dihydroindolylcarbonylmethoxy, di-fluoromethoxyphenylcarbamoylmethoxy, N-ethylpropylcarbamoylmethoxy, N-methylmethylpropylcarbamoylmethoxy, N-ethylbutylcarbamoylmethoxy, N-methylhexylcarbamoylmethoxy, fluorophenylcarbamoylmethoxy, dimethylaminophenylcarbamoylmethoxy, N-phenylbenzylcarbamoylmethoxy, N-methylphenethylcarbamoylmethoxy and N-methylcyclohexylcarbamoylmethoxy.

Suitable example of "lower alkyl" in $R^5$ can be referred to aformentioned "lower alkyl", in which the preferred one may be $(C_1-C_4)$alkyl, and the most preferred one may be methyl.

Suitable example of "aryl" in $R^5$ can be referred to aforementioned "aryl", in which the preferred one may be phenyl.

Suitable example of "lower alkylene" moiety in the term of "lower alkylene which may have one or more suitable substituent(s)" may include straight or branched one such as methylene, ethylene, trimethylene, 1-methylethylene, tetramethylene, pentamethylene, hexamethylene, methylmethylene, 1-ethylethylene, 2-ethylpropylene, and the like, in which the preferred one may be $(C_1-C_4)$alkylene, and the most preferred one may be methylene, ethylene and 1-methylethylene.

Suitable example of "suitable substituent(s)" moiety in the term of "lower alkylene which may have one or more suitable substituent(s)" may include aryl, in which the preferred one may be phenyl.

Suitable example of "lower alkenylene" may include straight or branched one having 2 to 6 carbon atom(s) such as vinylene, propenylene, butenylene, 1 or 2 or 3-pentenylene, 1 or 2 or 3-hexenylene, methylvinylene, ethylvinylene, 1 or 2 or 3-methylpropenylene, 1 or 2 or 3-ethylpropenylene, 1 or 2 or 3 or 4-methyl-1 or 2-butenylene, and the like, in which the preferred one may be $(C_2-C_4)$alkenylene, and the most preferred one may be vinylene.

The processes for preparing the object compound [I] are explained in detail in the following.

Process 1

The object compound [I] or a salt thereof can be prepared by reacting a compound [II] with a compound [III] or a salt thereof.

Suitable salt of the compound [III] may be the same as those exemplified for the compound [I].

The reaction is preferably carried out in the presence of a base such as an alkali metal carbonate [e.g. sodium carbonate, potassium carbonate, etc.], an alkaline earth metal carbonate [e.g. magnesium carbonate, calcium carbonate, etc.], an alkali metal bicarbonate [e.g. sodium bicarbonate, potassium bicarbonate, etc.], tri(lower) alkylamine [e.g. trimethylamine, triethylamine, etc.], picoline or the like.

The reaction is usually carried out in a conventional solvent, such as an alcohol [e.g. methanol, ethanol, propanol, isopropanol, etc.], diethyl ether, tetrahydrofuran, dioxane, or any other organic solvent which does not adversely influence the reaction.

The reaction temperature is not critical, and the reaction can be carried out under cooling to heating.

Process 2

The object compound [Ib] or a salt thereof can be prepared by subjecting a compound [Ia] or a salt thereof to elimination reaction of the amino protective group.

Suitable salts of the compounds [Ia] may be the same as those exemplified for the compound [I].

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

In case that the amino protective group is benzyl, the reduction is preferably carried out in the presence of a combination of palladium catalysts [e.g. palladium black, palladium on carbon, etc.] and formic acid or its salt [e.g. ammonium formate, etc.].

The reduction is usually carried out in a conventional solvent which does not adversely influence the reaction such as water, an alcohol [e.g. methanol, ethanol, propanol, etc.], chlorobenzene, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc. or a mixture thereof.

The reaction temperature of this reduction is not critical and the reaction is usually carried out under cooling to heating.

The object compound [I] or a salt thereof possesses gut selective sympathomimetic, anti-ulcerous, anti-pancreatitis, lipolytic and anti-pollakiuria activities, and are useful for the treatment and/or prevention of gastrointestinal disorders caused by smooth muscle contractions in human beings or animals, and more particularly to methods for the treatment and/or prevention of spasm or hyperanakinesia in case of irritable bowel syndrome, gastritis, gastric ulcer, duodenal ulcer, enteritis, cholecystapathy, cholangitis, urinary calculus and the like; for the treatment and/or prevention of ulcer such as gastric ulcer, duodenal ulcer, peptic ulcer, ulcer causes by non steroidal anti-inflammatory drugs, or the like; for the treatment and/or prevention of dysuria such as pollakiuria, urinary incontinence or the like in case of nervous pollakiuria, neurogenic bladder dysfunction, nocturia, unstable bladder, cystospasm, chronic cystitis, chronic prostatitis, overflow incontinence, passive incontinence, reflux incontinence, urge incontinence, urinary incontinence, or the like; and for the treatment and/or prevention of pancreatitis, obesity, diabetes, glycosuria, hyperlipidemia, hypertension, atherosclerosis, glaucoma, melancholia, depression, and the like.

The following compound to be used as the $\beta_3$ adrenergic receptor agonist which is shown by formulas (IV), (V), (VI), (VII) and (VII) are also useful for the therapeutic treatment of dysuria, and the like.

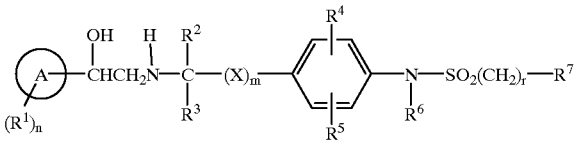

(IV)

or a salt thereof, wherein

A is a bond, —$(CH_2)_n$— or CH(B)—, where n is an integer of 1 to 3 and

B is —CN, —$CON(R^9)R^{9'}$or —$CO_2R^7$;

$R^1$ is lower alkyl, aryl or arylalkyl;

$R^2$ is hydrogen, hydroxy, alkoxy, —$CH_2OH$, cyano, —$C(O)OR^7$, —$CO_2H$, —$CONH_2$, tetrazole, —$CH_2NH_2$ or halogen;

$R^3$ is hydrogen, alkyl, heterocycle or

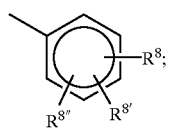

$R^4$ is hydrogen, alkyl or B;

$R^5$, $R^{5'}$, $R^8$, $R^{8'}$ and $R^{8''}$ are independently hydrogen, alkoxy, lower alkyl, halogen, —OH, —CN, —$(CH_2)_n$ $NR^6COR^7$, $CON(R^6)R^{6'}$, —$CON(R^6)OR^{6''}$, —$CO_2R^6$, —$SR^7$, —$SOR^7$, —$SO_2R^7$, —$N(R^6)SO_2R^1$, —$N(R^6)R^{6'}$, —$NR^6COR^7$, —$OCH_2CON(R^6)R^{6'}$, —$OCH_2CO_2R^7$ or aryl; or $R^5$ and $R^{5'}$ or $R^8$ and $R^{8'}$ may together with the carbon atoms to which they are attached form an aryl or heterocycle;

$R^6$ and $R^{6'}$ are independently hydrogen or lower alkyl; and $R^7$ is lower alkyl;

$R^9$ and $R^{9'}$ are independently hydrogen, lower alkyl, alkyl, cycloalkyl, arylalkyl, aryl, heteroaryl; or $R^9$ and $R^{9'}$ may together with the nitrogen atom to which they are attached form a heterocycle;

with the proviso that when
A is a bond or —$(CH_2)_n$ and
$R^3$ is hydrogen or unsubstituted alkyl,
then
$R^4$ is B or substituted alkyl:

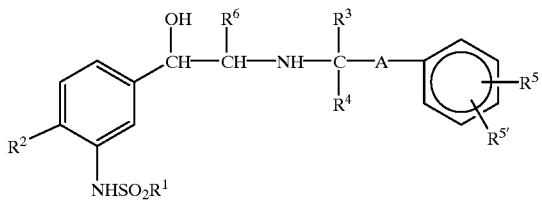

(V)

or a salt thereof, wherein n is 0 to 5;

m is 0 or 1;

r is 0 to 3;

A is pyridinyl;

$R^1$ is (1) hydroxy, (2) oxo, (3) halogen, (4) cyano, (5) $NR^8R^8$, (6) $SR^8$, (7) trifluoromethyl, (8) $C_1$–$C_{10}$ alkyl, (9) $OR^8$, (10) $SO_2R^9$, (11) $OCOR^9$, (12) $NR^8COR^9$, (13) $COR^9$, (14) $NR^8SO_2R^9$, (15) $NR^8CO_2R^8$, or (16) $C_1$–$C_{10}$ alkyl substituted by hydroxy, halogen, cyano, $NR^8R^8$, $SR^8$, trifluoromethyl, $OR^8$, $C_3$–$C_8$ cycloalkyl, phenyl, $NR^8COR^9$, $COR^9$, $SO_2R^9$, $OCOR^9$, $NR^8SO_2R^9$ or $NR^8CO_2R^8$;

$R^2$ and $R^3$ are independently (1) hydrogen, (2) $C_1$–$C_{10}$ alkyl or (3) $C_1$–$C_{10}$ alkyl with 1 to 4 substituents selected from hydroxy, $C_1$–$C_{10}$ alkoxy, and halogen;

X is (1)—$CH_2$—, (2) —$CH_2$—$CH_2$—, (3) —CH═CH— or (4) —$CH_2O$—;

$R^4$ and $R^5$ are independently (1) hydrogen, (2) $C_1$–$C_{10}$ alkyl, (3) halogen, (4) $NHR^8$, (5) $OR^8$, (6) $SO_2R^9$ or (7) $NHSO_2R^9$;

$R^6$ is (1) hydrogen or (2) $C_1$–$C_{10}$ alkyl;

$R^7$ is Z—$(R^{1a})_n$;

$R^{1a}$ is (1) $R^1$, (2) $C_3$–$C_8$ cycloalkyl, (3) phenyl optionally substituted with up to 4 groups independently selected from $R^8$, $NR^8R^8$, $OR^8$, $SR^8$ and halogen, or (4) 5 or 6-membered heterocycle with from 1 to 4 heteroatoms selected from oxygen, sulfur and nitrogen, optionally substituted with up to four groups independently selected from oxo, $R^8$, $NR^8R^8$, $OR^8$, $SR^8$, and halogen;

Z is (1) phenyl, (2) naphthyl, (3) a 5 or 6-membered heterocyclic ring with from 1 to 4 heteroatoms selected from oxygen, sulfur and nitrogen, (4) a benzene ring fused to a $C_3$–$C_8$ cycloalkyl ring, (5) a benzene ring fused to a 5 or 6-membered heterocyclic ring with from 1 to 4 heteroatoms selected from oxygen, sulfur and nitrogen, (6) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or (7) a 5 or 6-membered heterocyclic ring with from 1 to 4 heteroatoms selected from oxygen, sulfur and nitrogen fused to a $C_3$–$C_8$ cycloalkyl ring;

$R^8$ is (1) hydrogen, (2) $C_1$–$C_{10}$ alkyl, (3) $C_3$–$C_8$ cycloalkyl, (4) Z optionally having 1 to 4 substituents selected from halogen, nitro, oxo, $NR^{10}R^{10}$, $C_1$–$C_{10}$ alkyl, $C_1$–$C_{10}$ alkoxy, $C_1$–$C_{10}$ alkylthio, and $C_1$–$C_{10}$ alkyl having 1 to 4 substituents selected from hydroxy, halogen, $CO_2H$, $CO_2$-$C_1$–$C_{10}$ alkyl, $SO_2$—$C_1$–$C_{10}$ alkyl, $C_3$–$C_8$ cycloalkyl, $C_1$–$C_{10}$ alkoxy, and Z optionally substituted by from 1 to 3 of halogen, $C_1$–$C_{10}$ alkyl or $C_1$–$C_{10}$ alkoxy, or (5) $C_1$–$C_{10}$ alkyl having 1 to 4 substituents selected from hydroxy, halogen, $CO_2H$, $CO_2$—$C_1$–$C_{10}$ alkyl, $SO_2$—$C_1$–$C_{10}$ alkyl, $C_3$–$C_8$ cycloalkyl, $C_1$–$C_{10}$ alkoxy, $C_1$–$C_{10}$ alkyl, and Z optionally substituted by from 1 to 4 of halogen, $C_1$–$C_{10}$ alkyl or $C_1$–$C_{10}$ alkoxy;

$R^9$ is (1) $R^8$ or (2) $NR^8R^8$; and $R^{10}$ is (1) $C_1$–$C_{10}$ alkyl, or (2) two $R^{10}$ groups together with the N to which they are attached formed a 5 or 6-membered ring optionally substituted with $C_1$–$C_{10}$ alkyl:

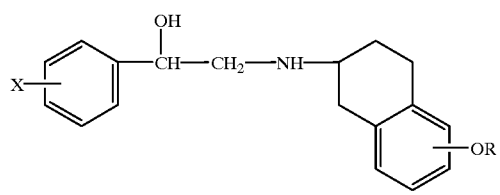

(VI)

or a salt thereof, wherein

X is hydrogen, halogen, trifluoromethyl or lower alkyl, and

R is hydrogen; lower alkyl which may have a suitable substituent selected from the group consisting of cyclo ($C_3$–$C_7$)alkyl, hydroxy, lower alkoxy, carboxy and lower alkoxycarbonyl; cyclo($c_3$–$C_7$) alkyl or lower alkanoyl:

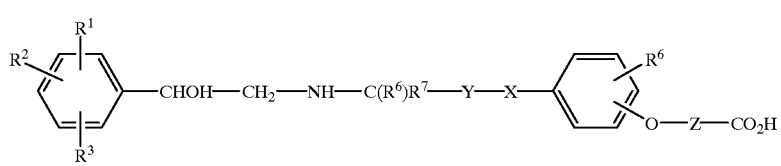

(VII)

or a salt, ester or amide thereof, wherein $R^1$ is a hydrogen, fluorine, chlorine or bromine atom or a hydroxyl, hydroxymethyl, methyl, methoxyl, amino, formamido, acetamido, methylsulphonylamino, nitro, benzyloxy, methylsulphonylmethyl, ureido, trifluoromethyl or p-methoxybenzylamino group;

$R^2$ is a hydrogen, fluorine, chlorine or bromine atom or a hydroxyl group;

$R^3$ is a hydrogen, chlorine or bromine atom or a hydroxyl group, $R^4$ is a hydrogen atom or a methyl group;

$R^5$ is a hydrogen atom or a methyl group;

$R^6$ is a hydrogen, fluorine or chlorine atom or a methyl, methoxyl or hydroxy group;

X is an oxygen atom or a bond;

Y is an alkylene group of up to 6 carbon atoms or a bond; and

Z is an alkylene, alkenylene or alkynylene group of up to 10 carbon atoms: or

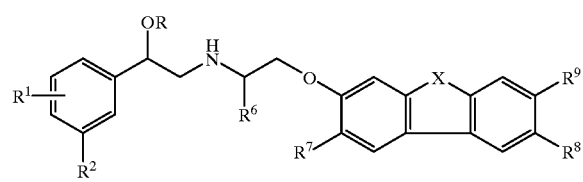

(VIII)

or a salt thereof, wherein

R is hydrogen or methyl,

R is hydrogen, halogen, hydroxy, benzyloxy, amino or hydroxymethyl, $R^2$ is hydrogen, hydroxymethyl, —$NHR^3$, —$SO_2NR^4R^{4'}$ or nitro, $R^3$ is hydrogen, methyl, —$SO_2R^5$, formyl or —$CONHR^{6'}$, $R^4$ and $R^{4'}$ are independently hydrogen, lower alkyl or benzyl, $R^5$ is lower alkyl, benzyl or —$NR^4R^{4'}$, $R^6$ is hydrogen or lower alkyl, $R^{6'}$ is hydrogen or lower alkyl, and, X is N, O, S or methylene;

when X is N, O or S, then $R^9$ is hydrogen, either $R^7$ or $R^8$ is hydrogen, and the other is hydrogen, amino, acetylamino or hydroxy;

when X is methylene, then both $R^7$ and $R^8$ is hydrogen, and $R^9$ is hydrogen, amino, acetylamino or hydroxy.

The compounds (IV), (V), (VI), (VII) and (VIII) identified above or a salt thereof to be used in the present invention are the known ones and disclosed in EP-A2-659737, U.S. Pat. No. 5,561,142, EP-A1-211721, EP-A1-023385, and WO97/25311, respectively.

In the formula (IV), the terms "alk" or "alkyl" refers to both straight and branched chain groups having 1 to 12 carbon atoms, preferably 1 to 8 carbons. It is understood, therefore, that the terms "alk" and "alkyl" denote both unsubstituted groups such as methyl, ethyl, n-propyl, iso-propyl, n-butyl, iso-butyl, sec-butyl, tert-butyl, n-pentyl, 1-methylbutyl, 2,2-dimethylbutyl, 2-methylpentyl, n-hexyl and the like as well as substituted groups. The term "substituted alkyl" specifically denotes an alkyl group as defined above having one or more of the following substituents: halo (especially to form trihaloalkyl, particularly trichloromethyl or trifluoromethyl); aryl; cycloalkyl; hydroxy; amino; thiol; or Y, where Y is —CN, alkoxy, —CON($R^6$)$R^{6'}$, —CO$_2$$R^6$ or —N($R^6$)SO$_2$$R^1$.

The term "lower alkyl" as employed herein includes such alkyl groups as described above containing 1 to 6 carbon atoms.

The term "alkoxy" refers to any of the above alkyl groups linked to an oxygen atom.

The term "lower alkoxy" refers to any of the above lower alkyl groups linked to an oxygen atom.

The term "aryl" refers to monocyclic or bicyclic aromatic groups containing from 6 to 10 carbons in the ring portion, such as phenyl, naphthyl, or such groups optionally substituted with one or more substituents selected from hydrogen, alkoxy, lower alkyl, halogen, —OH, —CN, —(CH$_2$)$_n$NR$^6$COR$^7$, —CON($R^6$)$R^{6'}$, —CON($R^6$)OR$^{6'}$, —CO$_2$R$^6$, —SOR$^7$, —SO$_2$R$^7$, —N($R^6$)SO$_2$R$^1$, —N($R^6$)R$^{6'}$, —NR$^6$COR$^7$, —OCH$_2$CON($R^6$)R$^{6'}$, —OCH$_2$CO$_2$R$^7$ or aryl. Phenyl and substituted phenyl are preferred.

The term "halogen" or "halo" refers to chlorine, bromine, fluorine or iodine.

The term "heterocycle" refers to fully saturated or unsaturated rings of 5 or 6 atoms containing one or two oxygen and/or sulfur atoms and/or one to four nitrogen atoms provided that the total number of heteroatoms in the ring is four or less. Preferred monocyclic heterocycle groups include 2- and 3-thienyl, 2- and 3-furyl, 2-, 3- and 4-pyridyl and imidazolyl. The term heterocycle also includes bicyclic rings wherein the five- or six-membered ring containing oxygen and/or sulfur and/or nitrogen atoms as defined above is fused to a benzene ring and the bicyclic ring is attached by way of an available carbon atom. Preferred bicyclic heterocycle groups include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl, 4-, 5-, 6- or 7-benzofuranzanyl, 4-, 5-, 6- or 7-benzodioxolyl and 4-, 5-, 6- or 7-benzofuran. The term "heterocycle" also includes such monocyclic and bicyclic rings wherein an available carbon atom is substituted with one or more substituents selected from nitro, keto, azo, thiazo, hydrogen, alkoxy, lower alkyl, halogen, —OH, —CN, —(CH$_2$)$_n$NR$^6$COR$^7$, —CON($R^6$) R$^{6'}$, —CON($R^6$)OR$^{6'}$, —CO$_2$R$^6$, —SR$^7$, —SOR$^7$, —SO$_2$R$^7$, —N($R^6$)SO$_2$R$^1$, —N($R^6$)R$^{6'}$, —NR$^6$COR$^7$, —OCH$_2$CON($R^6$)R$^{6'}$, —OCH$_2$CO$_2$R$^7$ or aryl.

In the formula (V), the alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

Examples of 5 and 6-membered heterocycles and fused heterocycles of A, Z and $R^{1a}$ include pyridyl, quinolinyl, pyrimidinyl, pyrrolyl, thienyl, imidazolyl, thiazolyl, benzimidazolyl, thiadiazolyl, benzothiadiazolyl, indolyl, indolinyl, benzodioxolyl, benzodioxanyl, benzothiophenyl, benzofuranyl, benzoxazinyl, benzisoxazolyl, benzothiazolyl, tetrahydronaphthyl, dihydrobenzofuranyl, tetrahydroquinolinyl, furopyridine and thienopyridine.

The preferred values of A and Z are phenyl, naphthyl, benzene ring fused to a 5 or 6-membered heterocyclic ring with from 1 to 4 heteroatoms selected from oxygen, sulfur and nitrogen, or heterocycles with from 1 to 4 heteroatoms independently selected from one of oxygen or sulfur, and/or 1 to 4 nitrogen atoms.

The more preferred values of A are phenyl, pyridyl, quinolinyl, pyrimidinyl, pyrrolyl, thienyl, imidazolyl, and thiazolyl.

The more preferred values of Z are phenyl, naphthyl, quinolinyl, thienyl, benzimidazolyl, thiadiazolyl, benzothiadiazolyl, indolyl, indolinyl, benzodioxolyl, benzodioxanyl, benzothiophenyl, benzofuranyl, benzoxazinyl, benzisoxazolyl, benzothiazolyl, tetrahydronaphthyl, dihydrobenzofuranyl, triazolyl, tetrazolyl, oxadiazolyl, imidazolyl, oxazolyl, thiazolyl, imidazolidinyl, pyrazolyl, isoxazolyl, pyridyl, pyrimidyl, pyrazolyl, tetrahydrobenzothiazolyl and tetrahydroquinolinyl. When Z is attached to —NSO$_2$(CH$_2$)$_r$—, it is preferably phenyl, naphthyl or a benzene ring fused to a 5 or 6-membered heterocyclic ring with from 1 to 4 heteroatoms selected from oxygen, sulfur and nitrogen. When Z is part of the definition of $R^8$, it is preferably phenyl, a 5 or 6-membered heterocyclic ring with from 1 to 4 heteroatoms selected from oxygen, sulfur and nitrogen, a benzene ring fused to a 5 or 6-membered heterocyclic ring with from 1 to 4 heteroatoms selected from oxygen, sulfur and nitrogen, or a 5 or 6-membered heterocyclic ring with from 1 to 4 heteroatoms selected from oxygen, sulfur and nitrogen fused to a $C_3$–$C_8$ cycloalkyl ring.

The preferred heterocycles of $R^{1a}$ are thienyl, thiadiazolyl, thiazolyl, tetrazolyl, oxadiazolyl, imidazolyl, oxazolyl, thiazolyl, imidazolidinyl, isoxazolyl, pyridyl, pyrimidyl, and pyrazolyl.

Certain of the above defined terms may occur more than once in the above formula and upon such occurrence each term shall be defined independently of the other; thus for example. NR$^8$R$^8$ may represent NH$_2$, NHCH$_3$, N(CH$_3$)CH$_2$CH$_3$, and the like.

In the formula (VI), the term "lower alkyl" may include straight or branched one having 1 to 6 carbon atom(s), such as methyl, ethyl, propyl, isopropyl, butyl, isobutyl, sec-butyl, tert-butyl, pentyl, 3-pentyl, isopentyl, tert-pentyl, neopentyl, hexyl, isohexyl, and the like.

The term "halogen" may include fluorine, chlorine, bromine, iodine, and the like.

The term "lower alkoxy" may include methoxy, ethoxy, propoxy, isopropoxy, butoxy, isobutoxy, t-butoxy, pentyloxy, t-pentyloxy, hexyloxy, and the like.

The term "lower alkoxycarbonyl" may include methoxycarbonyl, ethoxycarbonyl, propoxycarbonyl, isopropoxycarbonyl, t-butoxycarbonyl, t-pentyloxycarbonyl, heptyloxycarbonyl, and the like.

The term "lower alkanoyl" may include acetyl, propanoyl, butanoyl, 2-methylpropanoyl, pentanoyl, 2,2-dimethylpropanoyl, hexanoyl, and the like.

The term "cyclo($C_3$–$C_7$)alkyl" may include cyclopropyl, cyclobutyl, cyclopentyl, cyclohexyl, cycloheptyl, and the like.

In the formula (VII), the term "alkylene" may include methylene, ethylene, propylene, isopropylene, butylene, isobutylene, sec-butylene, tert-butylene, pentylene, tert-pentylene, neo-pentylene, hexylene, iso-hexylene, heptylene, octylene, nonylene, decylene, and the like.

The term "alkenylene" may include vinylene, propenylene, butenylene, 1 or 2 or 3-pentenylene, 1 or 2 or 3-hexenylene, methylvinylene, ethylvinylene, heptenylene, octenylene, nonenylene, decenylene, and the like.

The term "alkynylene" may include ethynylene, propynylene, butynylene, 1 or 2 or 3-pentynylene, 1 or 2 or 3-hexynylene, heptynylene, octynylene, nonynylene, decynylene, and the like.

In the formula (VIII), the term "lower alkyl" may include straight or branched one having 1 to 6 carbon atom(s), such as methyl, ethyl, propyl, isopropyl, butyl, isobutyl, sec-butyl, tert-butyl, pentyl, 3-pentyl, isopentyl, tert-pentyl, neopentyl, hexyl, isohexyl, and the like.

In order to show the usefulness of the compounds (IV) to (VIII) for the prophylactic and therapeutic treatment of above-mentioned diseases in a human being or an animal, the pharmacological test data of the representative compounds thereof are shown in the following.

Test 1

Effect on the increase in intravesical pressure induced by carbachol in anesthetized dog Test Compound (1) N-[5-[2-[1-(3,4-Dimethoxyphenyl)-2-phenylethylamino]-1(R)-hydroxyethyl]-2-hydroxyphenyl]methanesulfonamide (This compound was obtained according to a similar manner to that of Example 1 in EP-A2-659737.)

(2) N-[4-[2-[2(R)-Hydroxy-2-(pyridin-3-yl)ethylamino]ethyl]-phenyl]-4-[4-(3-cyclopentylpropyl)-5-tetrazolon-1-yl]-benzenesulfonamide (This compound was obtained according to a similar manner to that of Example 70 in U.S. Pat. No. 5,561,142.)

(3) N-[5-[2-[2-(9H-Carbazol-2-yloxy)ethylamino]-1-hydroxyethyl]-2-hydroxyphenyl]methanesulfonamide hydrochloride (This compound was obtained according to a similar manner to that of Example 2 in WO97/25311.)

Test Method

Female Beagle dogs weighing 8.0–15.0 kg were fasted for 24 hours and maintained under halothane anesthesia. A 12F Foley catheter was lubricated with water soluble jelly, inserted into the urethral orifice and advanced approximately 10 cm until the balloon tip was placed well inside the bladder. The balloon was then inflated with 5 ml of room air and catheter slowly withdrawn just part the first resistance that is felt at the bladder neck. Urine was completely drained out throught the catheter, and 30 ml of biological saline was infused. The catheter was connected to pressure transducer, and intravesical pressure was continuously recorded. The test compound was injected intravenously at 5 minutes before the administration of carbachol (1.8 $\mu$g/kg)

| Test Results | |
|---|---|
| Treatment | Increase in intravesical pressure (mmHg) |
| Control | 5.0 ± 0.9 |
| Test Compound (1) (0.01 mg/kg) | 1.8 ± 0.3** |
| Control | 5.0 ± 1.2 |
| Test Compound (2) (0.01 mg/kg) | 2.3 ± 1.5* |

-continued

| Test Results | |
|---|---|
| Treatment | Increase in intravesical pressure (mmHg) |
| Control | 5.0 ± 0.5 |
| Test Compound (3) (0.01 mg/kg) | 1.7 ± 0.6** |

*$P < 0.05$ vs Control (ANOVA) (N = 4)
**$P < 0.01$ vs Control (ANOVA) (N = 3)

The test compounds (1), (2) and (3) inhibited the increase in intravesical pressure induced by carbachol.

Test 2

Effect on cystometrogram in anesthetized rat

Test Compound (4-1-2(S)-[(7-Ethoxycarbonylmethoxy-1,2,3,4-tetrahydronaphthalen-2-yl)amino]-1(R)-(3-chlorophenyl)ethanol hydrochloride (This compound was obtained according to a similar manner to that of Example 11 in EP-A1-211721.)

Test Method

Male S.D. rats, aged 7–9 weeks, were anesthetized with urethane (1.2 g/kg, sc) and supine on a board. After a midline incision in the abdomen, the bladder was exposed. Polyethylene catheters, which were used to measure the intravesical pressure and to infuse saline, were inserted into the bladder through a small incision at the apex of the bladder dome. The bladder catheters were connected to an infusion pump and pressure transducer respectively. Saline was infused a rate of 5.0 ml/hr for 1 hour. Cystometrography was performed at 15 minutes intervals for 1 hour. The bladder capacity (volume) was calculated from the time required to fill the bladder. The test compound was administered intravenously via femoral vein.

| Test Result | | |
|---|---|---|
| | Vehicle | compound (4) (0.01 mg/kg) |
| Time (minutes) | (relative % of before value) | (N = 5) |
| Before (Control) | 100 | 100 |
| 0–15 | 128 | 152 |
| 15–30 | 111 | 146 |
| 30–45 | 114 | 143 |
| 45–60 | 104 | 151 |

The test compound (4) increased in bladder capacity at a dose of 0.01 mg/kg.

Test 3

Effect on rhythmic contraction of bladder in anesthetized rat

Test Compound (5) Methyl 4-[2(R)-[2-(3-chlorophenyl)-2(R)-hydroxyethylamino]propyl]phenoxyacetate (This compound was obtained according to a similar manner to that of Example 6 in EP-Al-023385.)

Test Method

Male S.D. rats, aged 7–8 weeks, were anesthetized with urethane (1.2 g/kg, ip) and supine on a board. After a midline incision in the abdomen, the bladder was exposed. Balloon catheter, which was used to measure the intravesical pressure, was inserted into the bladder through a small incision at the apex of the bladder dome. The balloon was then inflated with distilled water and the balloon port of the catheter was connected to pressure transducer. Rhythmic contraction of bladder induced by increase intravesical pressure to 10 mmHg. The test compound was administered intravenously via femoral vein.

| | Test Result | |
|---|---|---|
| | compound (5) (0.1 mg/kg) | |
| Time (minutes) | (relative % of before value) | (N = 3) |
| Before (Control) | 100 | |
| 30 | 66.3** | |

**P < 0.01 vs Before value (paired t-test)

The test compound (5) decreased in contractile force of bladder at a dose of 0.1 mg/kg.

Suitable salt of the compounds in the present invention is a pharmaceutically acceptable and conventional non-toxic salt, and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic sulfonic acid addition salt (e.g., formate, acetate, trifluoroacetate, maleate, tartrate, fumarate, methanesulfonate, benzenesulfonate, toluenesulfonate, etc.); a salt with a basic or acidic amino acid (e.g., arginine, aspartic acid, glutamic acid, etc.).

The compounds in the present invention can be isolated and purified by a conventional method such as pulverization, recrystallization, column-chromatography, high-performance liquid chromatography (HPLC), reprecipitation, desalting resin column chromatography, or the like.

The compound in the present invention may be obtained as its hydrate, and its hydrate is included within the scope of present invention.

It is to be noted that each of the compounds in the present invention may include one or more stereoisomer such as optical isomer(s) and geometrical isomer(s) due to asymmetric carbon atom(s) and double bond(s) and all such isomers and the mixture thereof are included within the scope of the present invention.

The compounds in the present invention or a salt thereof include solvated compound [e.g., enclosure compound (e.g., hydrate, etc.)].

The compounds in the present invention or a salt thereof include both its crystal form and non-crystal form.

It should be understood that the compounds in the present invention may include the prodrug form.

This application is based on applications No. PP2826/98 and PP5058/98 filed in Australia, the content of which is incorporated hereinto by reference.

The compounds in the present invention may be obtained by methods exemplified by EP-A2-659737, U.S. Pat. No. 5,561,142, EP-A1-211721, EP-A1-023385, or WO97/25311.

The patent, patent applications and publications cited herein are incorporated by reference.

The pharmaceutical composition of the present invention can be used in the form of a pharmaceutical preparation, for example, in solid, semisolid or liquid form, which contains a compound in the present application or a pharmaceutically acceptable salt thereof, as an active ingredient in admixture with an organic or inorganic carrier or excipient suitable for rectal, pulmonary (nasal or buccal inhalation), nasal, ocular, external (copical), oral or parenteral (including subcutaneous, intravenous and intramuscular) administrations or insufflation.

The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used.

The compound or a salt thereof in the present invention is included in the pharmaceutical composition in an amount sufficient to produce the desired effect upon the process or condition of the diseases.

The pharmaceutical composition of the present invention can be manufactured by the conventional method in this field of the art. If necessary, the technique generally used in this field of the art for improving the bioavailability of a drug can be applied to the pharmaceutical composition of the present invention.

For applying the composition to a human being or an animal, it is preferable to apply it by intravenous (including i.v. infusion), intramuscular, pulmonary, or oral administration, or insufflation.

While the dosage of therapeutically effective amount of the compound in the present invention varies from and also depends upon the age and condition of each individual patient to be treated, in the case of intravenous administration, a daily dose of 0.01–100 mg of the compound in the present invention per kg weight of a human being or an animal, in the case of intramuscular administration, a daily dose of 0.01–100 mg of the compound in the present invention per kg weight of a human being or an animal, in case of oral administration, a daily dose of 0.01–200 mg of the compound in the present invention per kg weight of a human being or an animal is generally given for the prophylactic and/or therapeutic treatment of above-mentioned diseases in a human being or an animal.

The following Preparations and Examples are given for the purpose of illustrating this invention.

Preparation 1

Under nitrogen, a solution of N-benzyl-(3-ethoxycarbonylmethoxy-6,7,8,9-tetrahydro-5H-benzocyclohepten-6-yl)amine (2.0 g) in tetrahydrofuran (20 ml) was added di-tert-butyl dicarbonate (1.4 g) at 5° C., and the solution was stirred at room temperature for 2.5 hours. The resulting solution was evaporated in vacuo. The residue was chromatographed (hexane-ethyl acetate) over silica gel to afford [8-(N-benzyl-tert-butoxycarbonylamino)-6,7,8,9-tetrahydro-5H-benzocyclohepten-2-yloxy]acetic acid ethyl ester (2.58 g).

NMR (CDCl$_3$, δ): 1.29 (3H, t, J=7.1 Hz), 1.08–1.63 (11H, m), 1.87–2.18 (3H, m), 2.50–2.70 (3H, m), 3.17–3.35 (1H, m), 4.27 (2H, q, J=7.1 Hz), 4.37–4.70 (2H, m), 4.55 (2H, s), 6.60 (1H, dd, J=2.5 and 8.1 Hz), 6.93 (1H, d, J=8.3 Hz), 7.19–7.83 (4H, m)

Preparation 2

To a solution of [8-(N-benzyl-tert-butoxycarbonylamino)-6,7,8,9-tetrahydro-5H-benzocyclohepten-2-yloxy]acetic acid ethyl ester (2.5 g) in ethanol (25 ml) was added 1N sodium hydroxide aqueous solution at 5° C., and the solution was stirred at room temperature for 1 hour. The resulting solution was evaporated in vacuo to afford sodium [8-(N-benzyl-tert-butoxycarbonylamino)-6,7,8,9-tetrahydro-5H-benzocyclohepten-2-yloxy]acetate (2.35 g).

NMR (CDCl$_3$, δ): 1.04–1.60 (10H, m), 1.75–2.11 (3H, m), 2.41–2.67 (4H, m), 3.15–3.55 (1H, m) , 4.05 (2H, s), 4.27–4.65 (2H, m), 6.52 (2H, d, J=7.9 Hz), 6.88 (1H, d, J=8.2 Hz), 7.12–7.42 (5H, m)

Preparation 3

Under nitrogen, to a mixture of sodium [8-(N-benzyl-tert-butoxycarbonylamino)-6,7,8,9-tetrahydro-5H-benzocyclohepten-2-yloxy]acetate (0.50 g) in dichloromethane (5 ml) were added 4N hydrogenchloride in ethyl acetate (0.28 ml), 1-(3-dimethylaminopropyl)-3-ethylcarbodiimide hydrochloride (0.24 g), aniline (112 μl) and a catalytic amount of 4-dimethylaminopyridine at 5° C., and the mixture was stirred at room temperature for 3 hours. The resulting mixture was poured into 1N hydrogen chloride aqueous solution and extracted with ethyl acetate. The organic layer was washed with saturated aqueous sodium bicarbonate solution and brine, dried over magnesium sulfate, and evaporated in vacuo. The residue was chromatographed (hexane-ethyl acetate) over silica gel to afford N-benzyl-N-tert-butoxycarbonyl-(3-N-phenylcarbamoylmethoxy-6,7,8,9-tetrahydro-5H-benzocyclohepten-6-yl)amine (0.47 g)

NMR (CDCl$_3$, δ): 1.13–1.75 (11H, m), 1.90–2.25 (3H, m), 2.50–2.80 (3H, m), 3.24–3.38 (1H, m), 4.27–4.78 (2H, m), 4.53 (2H, s), 6.68 (1H, dd, J=2.5 and 8.1 Hz), 6.98 (1H, d, J=8.3 Hz), 7.12–7.43 (9H, m), 7.58–7.65 (2H, m)

The following compound was obtained according to a similar manner to that of Preparation 3.

Preparation 4

N-Benzyl-N-tert-butoxycarbonyl-(3-N-butylcarbamoylmethoxy-6,7,8,9-tetrahydro-5H-benzocyclohepten-6-yl)amine NMR (CDCl$_3$, δ): 0.93 (3H, t, J=7.2 Hz), 1.10–2.20 (17H, m), 2.50–2.75 (3H, m), 3.15–3.45 (4H, m), 4.28–4.77 (2H, m), 4.40 (2H, s), 6.60 (2H, dd, J=2.4 and 8.1 Hz), 6.95 (1H, d, J=8.3 Hz), 7.25–7.50 (5H, m)

Preparation 5

Under nitrogen, 4N hydrogenchloride in ethyl acetate (4 ml) was added to N-benzyl-N-tert-butoxycarbonyl-(3-N-phenylcarbamoylmethoxy-6,7,8,9-tetrahydro-5H-benzocyclohepten-6-yl)amine (0.45 g) at room temperature, and the solution was stirred at the same temperature for 3.5 hours. The resulting solution was evaporated in vacuo. The residue was dissolved in a mixture of saturated aqueous sodium bicarbonate solution and ethyl acetate. After separation, the organic layer was dried over magnesium sulfate and evaporated in vacuo to afford 2-(8-benzylamino-6,7,8,9-tetrahydro-5H-benzocyclohepten-2-yloxy)-N-phenylacetamide (346 mg).

NMR (CDCl$_3$, δ): 1.38–1.62 (1H, m), 1.63–2.14 (4H, m), 2.65–2.82 (3H, m), 2.90–2.98 (2H, m), 3.82 (2H, ABq, J=3.7 and 12.7 Hz), 4.58 (2H, s), 6.71 (1H, dd, J=2.7 and 8.2 Hz), 6.82 (1H, d, J=2.7 Hz), 7.04 (1H, d, J=8.2 Hz), 7.13–7.42 (8H, m), 7.56–7.65 (2H, m)

MASS (m/z) 401 (M+H)$^+$

The following compound was obtained according to a similar manner to that of Preparation 5.

Preparation 6

2-(8-Benzylamino-6,7,8,9-tetrahydro-5H-benzocyclohepten-2-yloxy)-N-butylacetamide NMR (CDCl$_3$, δ): 0.92 (3H, t, J=7.2 Hz), 1.25–1.61 (4H, m), 1.73–2.30 (4H, m), 2.63–3.05 (5H, m), 3.34 (2H, q, J=6.9 Hz), 3.85 (2H, ABq, J=13.1 and 17.0 Hz), 4.45 (2H, s), 6.64 (1H, dd, J=2.7 and 8.2 Hz), 7.01 (1H, d, J=8.2 Hz), 7.20–7.45 (5H, m)

MASS (m/z): 381 (M+H)$^+$

Preparation 7

A solution of N-benzyl-(6,7,8,9-tetrahydro-2-hydroxy-5H-benzocyclohepten-6-yl)amine (194 mg) and di-tert-butyl dicarbonate (174 mg) in tetrahydrofuran (2 ml) was stirred at room temperature for 20 hours and partitioned between ethyl acetate and an aqueous solution of sodium bicarbonate. The organic layer was separated, washed with brine, dried over sodium sulfate, and evaporated in vacuo. The residue was chromatographed (toluene-ethyl acetate) over silica gel (5.8 g) to afford N-benzyl-N-(6,7,8,9-tetrahydro-2-hydroxy-5H-benzocyclohepten-6-yl)-tert-butoxycarbonylamine as a pale yellow solid (196 mg).

mp: 150–156° C. (dec.)

IR (KBr): 3348 (br), 1666, 1246 cm$^{-1}$

NMR (DMSO-d$_6$, δ): 1.2–1.6 (10H, m), 1.96 (3H, m), 2.49–2.7 (3H, m), 3.10–3.85 (2H, m), 4.30–4.7 (2H, m), 6.46–6.54 (2H, m), 6.77 (1H, m), 7.15–7.36 (5H, m)

(+) API-ES MASS (m/z): 390 (M$^+$+Na)

Preparation 8

A solution of N-benzyl-N-(6,7,8,9-tetrahydro-2-hydroxy-5H-benzocyclohepten-6-yl)-tert-butoxycarbonylamine (166 mg) and N-chlorosuccinimide (66.4 mg) in 1,4-dioxane (2 ml) was refluxed for 28 hours, cooled to room temperature, and partitioned between ethyl acetate and brine. The organic layer was separated, washed with brine, dried over sodium sulfate, and evaporated in vacuo. The residue was chromatographed (toluene -ethyl acetate) over silica gel (3.6 g) to afford N-benzyl-N-(3-chloro-6,7,8,9-tetrahydro-2-hydroxy-5H-benzocyclohepten-6-yl)-tert-butoxycarbonylamine (139 mg) as a colorless gum.

IR (KBr): 3411 (br) , 3263 (br) , 1655, 1252 cm$^{-1}$

Preparation 9

A mixture of N-benzyl-N-(3-chloro-6,7,8,9-tetrahydro-2-hydroxy-5H-benzocyclohepten-6-yl)-tert-butoxycarbonylamine (135 mg) and 4N hydrogen chloride in ethyl acetate (3 ml) was stirred under ice-cooling for 2 hours and at room temperature for 5 hours and evaporated in vacuo. The residue was partitioned between ethyl acetate and an aqueous solution of sodium bicarbonate. The organic layer was separated, washed with brine, dried over sodium sulfate, and evaporated in vacuo to afford N-benzyl-(3-chloro-6,7,8,9-tetrahydro-2-hydroxy-5H-benzocyclohepten-6-yl)amine (100 mg) as a yellow gum.

IR (KBr): 3419 (br), 1238 cm$^{-1}$

NMR (CDCl$_3$, δ): 1.48–1.59 (1H, m), 1.71–2.03 (3H, m), 2.3–3.16 (6H, m), 3.78 (1H, d, J=13.0 Hz), 3.87 (1H, d, J=13.0 Hz), 6.73 (1H, s), 7.08 (1H, s), 7.15–7.32 (6H, m)

Preparation 10

Under nitrogen, to a suspension of sodium hydride (60% in oil, 47 mg) in N,N-dimethylformamide (3 ml) was dropwise added 8-benzylamino-6,7,8,9-tetrahydro-5H-benzocyclohepten-2-ol (300 mg) in N,N-dimethylformamide (2 ml) at 5° C., and the mixture was stirred at the same temperature for 30 minutes. To this one was added n-propyl bromide (0.10 ml), and the mixture was stirred at the same temperature for 3 hours. The resulting mixture was poured into saturated aqueous sodium hydrogencarbonate, and extracted with ethyl acetate. The organic layer was washed with brine, dried over anhydrous magnesium sulfate, and evaporated in vacuo. The residue was purified by column chromatography on silica gel (hexane:ethyl acetate =50:1 to 30:1) to give N-benzyl-(3- isopropoxy-6,7,8,9-tetrahydro-5H-benzocyclohepten-6-yl)amine (278 mg)

(+) ESI-MASS (m/z): 310 (M+H)$^+$

The following compounds [Preparation 11 and 12] were obtained according to a similar manner to that of Preparation 10.

Preparation 11

N-Benzyl-(3-hexyloxy-6,7,8,9-tetrahydro-5H-benzocyclohepten-6-yl)amine (+) APCI-MASS (m/z) 352 (M+H)$^+$ Preparation 12

N-Benzyl-(3-benzyloxy-6,7,8,9-tetrahydro-5H-benzocyclohepten-6-yl)amine

NMR (CDCl$_3$, δ): 1.2–1.6 (2H, m), 1.7–2.1 (3H, m), 2.6–2.95 (5H, m), 3.7–3.9 (2H, m), 5.03 (2H, s), 6.70 (1H, dd, J=2.7 and 8.2 Hz), 6.83 (1H, d, J=2.6 Hz), 6.98 (1H, d, J=8.2 Hz), 7.2–7.5 (10H, m)

Preparation 13

Under nitrogen, a solution of (2S)-1-[N-benzyl-(3-benzyloxy-6,7,8,9-tetrahydro-5H-benzocyclohepten-6-yl)amino]-3-phenoxy-2-propanol (20 g), chlorotriethylsilane (7.4 ml), imidazole (3.2 g) and 4-dimethylaminopyridine (0.48 g) in N,N-dimethylformamide (200 ml) was stirred at room temperature for 12 hours. The resulting mixture was poured into water, and extracted with ethyl acetate-hexane (1:1). The organic layer was successively washed with saturated aqueous sodium hydrogencarbonate and brine, dried over anhydrous magnesium sulfate, and evaporated in vacuo to give N-benzyl-N-(3-benzyloxy-6,7,8,9-tetrahydro-5H-benzocyclohepten-6-yl)-[(2S)-3-phenoxy-2-(triethylsilyloxy)-propyl]amine (25 g).

(+) ESI-MASS (m/z): 622 (M+H)$^+$

Preparation 14

A mixture of N-benzyl-N-(3-benzyloxy-6,7,8,9-tetrahydro-5H-benzocyclohepten-6-yl)-[(2S)-3-phenoxy-2-(triethylsilyloxy)propyl]amine (25 g) and 10% palladium on activated carbon (50% wet, 2.5 g) in methanol (250 ml) was stirred at room temperature in the presence of hydrogen at an atmospheric pressure for 5 hours. After filtration, the filtrate was evaporated in vacuo to give 8-[(2S)-3-phenoxy-2-(triethylsilyloxy)propylamino]-6,7,8,9-tetrahydro-5H-benzocyclohepten-2-ol (17 g).

(+) APCI-MASS (m/z): 442 (M+H)$^+$

Preparation 15

Under nitrogen, a mixture of 8-[(2S)-3-phenoxy-2-(triethylsilyloxy)propylamino]-6,7,8,9-tetrahydro-5H-benzocyclohepten-2-ol (17 g) and di-tert-butyl dicarbonate (9.5 g) in tetrahydrofuran (180 ml) was stirred at room temperature for 18 hours. After evaporation, the residue was purified by column chromatography on silica gel (hexane:ethyl acetate =20:1 to 10:1) to give N-(3-hydroxy-6,7,8,9-tetrahydro-5H-benzocyclohepten-6-yl)-N-[(2S)-3-phenoxy-2-(triethylsilyloxy)propyl]-tert-butoxycarbonylamine (17 g).

(+) APCI-MASS (m/z): 442 (M−Boc+2H)$^+$

Preparation 16

Under nitrogen, to a suspension of sodium hydride (60% in oil, 12 mg) in N,N-dimethylformamide (2 ml) was dropwise added N-(3-hydroxy-6,7,8,9-tetrahydro-5H-benzocyclohepten-6-yl)-N-[(2S)-3-phenoxy-2-(triethylsilyloxy)propyl]-tert-butoxycarbonylamine (150 mg) in N,N-dimethylformamide (1 ml) at 5° C., and the mixture was stirred at the same temperature for 30 minutes. To this one was added ethyl iodide (27 µl), and the mixture was stirred at room temperature for 2 hours. The resulting mixture was poured into saturated aqueous sodium hydrogencarbonate, and extracted with ethyl acetate. The organic layer was washed with brine, dried over anhydrous magnesium sulfate, and evaporated in vacuo. The residue was purified by column chromatography on silica gel (hexane:ethyl acetate=20:1) to give N-(3-ethoxy-6,7,8,9-tetrahydro-5H-benzocyclohepten-6-yl)-N-[(2S)-3-phenoxy-2-(triethylsilyloxy)propyl]-tert-butoxycarbonylamine (130 mg).

NMR (CDCl$_3$, δ): 0.55–0.75 (6H, m), 0.9–1.0 (9H, m), 1.2–1.55 (4H, m), 1.48 (9H, m), 1.9–2.2 (3H, m), 2.55–2.9 (3H, m), 3.1–3.65 (4H, m), 3.85–4.1 (4H, m), 4.2–4.4 (1H, m), 6.55–6.7 (2H, m), 6.85–7.0 (4H, m), 7.2–7.3 (2H, m)

(+) ESI-MASS (m/z): 592 (M+Na)$^+$

The following compound was obtained according to a similar manner to that of Preparation 16.

Preparation 17

N-(3-Allyloxy-6,7,8,9-tetrahydro-5H-benzocyclohepten-6-yl)-N-[(2S)-3-phenoxy-2-(triethylsilyloxy)propyl]-tert-butoxycarbonylamine NMR (DMSO-d$_6$, δ): 0.55–0.75 (6H, m), 0.8–1.1 (9H, m), 1.2–1.6 (1H, m), 1.48 (9H, m), 1.9–2.2 (3H, m), 2.6–2.9 (2H, m), 3.15–3.7 (4H, m), 3.8–4.05 (2H, m), 4.25–4.5 (3H, m), 5.25–5.45 (2H, m), 5.95–6.15 (1H, m), 6.6–6.75 (2H, m), 6.8–7.0 (4H, m), 7.25–7.3 (2H, m)

Preparation 18

Under nitrogen, to dimethylsulfoxide (3 ml) was added potassium hydroxide (31 mg) at room temperature, and the suspension was stirred at the same temperature for 1 hour. To this one were added N-(3-hydroxy-6,7,8,9-tetrahydro-5H-benzocyclohepten-6-yl)-N-[(2S)-3-phenoxy-2-(triethylsilyloxy)propyl]-tert-butoxycarbonylamine (150 mg) and isopropyl bromide (78 µl), and the mixture was stirred at room temperature for 3 hours. The resulting mixture was poured into aqueous 10% sodium hydrogencarbonate, and extracted with ethyl acetate. The organic layer was washed with brine, dried over anhydrous magnesium sulfate, and evaporated in vacuo. The residue was purified by column chromatography on silica gel (hexane:ethyl acetate =20:1) to give N-(3-isopropoxy-6,7,8,9-tetrahydro-5H-benzocyclohepten-6-yl)-N-[(2S)-3-phenoxy-2-(triethylsilyloxy)propyl]-tert-butoxycarbonylamine (96 mg).

(+) APCI-MASS (m/z): 326 (M−Boc+2H)$^+$

The following compounds [Preparations 19 to 21] were obtained according to a similar manner to that of Preparation 18.

Preparation 19

N-(3-Benzyloxy-6,7,8,9-tetrahydro-5H-benzocyclohepten-6-yl)-N-[(2S)-3-phenoxy-2-(triethylsilyloxy)propyl]-tert-butoxycarbonylamine (+) APCI-MASS (m/z): 532 (M−Boc+2H)$^+$ Preparation 20

N-Benzyl-N-[3-(3-cyanopyridin-2-yloxy)-6,7,8,9-tetrahydro-5H-benzocyclohepten-6-yl]-tert-butoxycarbonylamine (+) APCI-MASS (m/z): 370 (M−Boc+2H)$^+$ Preparation 21

N-Benzyl-N-(2-chloro-3-methoxy-6,7,8,9-tetrahydro-5H-benzocyclohepten-6-yl)-tert-butoxycarbonylamine (+) APCI-MASS (m/z): 316, 318 (M−Boc+2H)$^+$ Preparation 22

Under nitrogen, to a solution of N-(3-hydroxy-6,7,8,9-tetrahydro-5H-benzocyclohepten-6-yl)-N-[(2S)-3-phenoxy-2-(triethylsilyloxy)propyl]-tert-butoxycarbonylamine (150 mg) in tetrahydrofuran (5 ml) was added triphenylphosphine (290 mg), cyclopentanol (60 µl) and diethyl azodicarboxylate (174 µl) at 5° C., and the mixture was stirred at the same temperature for 5.5 hours. The resulting mixture was poured into saturated aqueous sodium hydrogencarbonate, and extracted with ethyl acetate. The organic layer was washed with brine, dried over anhydrous magnesium sulfate, and evaporated in vacuo. The residue was purified by column chromatography on silica gel (hexane:ethyl acetate=10:1) to give N-(3-cyclopentyloxy-6,7,8,9-tetrahydro-5H-benzocyclohepten-6-yl)-N-[(2S)-3-phenoxy-2-(triethylsilyloxy)propyl]-tert-butoxycarbonylamine (108 mg).

(+) APCI-MASS (m/z): 510 (M−Boc+2H)$^+$

The following compound was obtained according to a similar manner to that of Preparation 22.

Preparation 23

N-(3-Phenethyloxy-6,7,8,9-tetrahydro-5H-benzocyclohepten-6-yl)-N-[(2S)-3-phenoxy-2-(triethylsilyloxy)propyl-tert-butoxycarbonylamine (+) APCI-MASS (m/z): 546 (M−Boc+2H)$^+$ Preparation 24

Under nitrogen, to a suspension of potassium carbonate (76 mg) in a mixture of acetonitrile (5 ml) and N,N-dimethylformamide (2 ml) was added N-(3-hydroxy-6,7,8,9-tetrahydro-5H-benzocyclohepten-6-yl)-N-[(2S)-3-phenoxy-2-(triethylsilyloxy)propyl]-tert-butoxycarbonylamine (150 mg) at room temperature. After being stirred at the same temperature for 30 minutes, to this one was an excessive amount of bromofluoromethane, and the mixture was stirred for 12 hours. The resulting solution was poured into saturated aqueous sodium hydrogencarbonate, and extracted with ethyl acetate. The organic layer was washed with brine, dried over anhydrous magnesium sulfate, and evaporated in vacuo. The residue was purified by column chromatography on silica gel (hexane:ethyl acetate=10:1) to give N-(3-fluoromethoxy-6,7,8,9-tetrahydro-5H-benzocyclohepten-6-yl)-N-[(2S)-3-phenoxy-2-(triethylsilyloxy)propyl]-tert-butoxycarbonylamine (130 mg).

(+) APCI-MASS (m/z): 474 (M−Boc+2H)$^+$

Preparation 25

Under nitrogen, to a solution of N-(3-hydroxy-6,7,8,9-tetrahydro-5H-benzocyclohepten-6-yl)-N-[(2S)-3-phenoxy-2-(triethylsilyloxy)propyl]-tert-butoxycarbonylamine (150 mg) in dichloromethane (5 ml) were added pyridine (64 ml), 4-nitrophenyl chloroformate (116 mg) and a catalytic amount of 4-dimethylaminopyridine at 5° C. After being stirred at the same temperature for 2 hours, to this one was added about 6.8M ammonia in ethanol (0.5 ml), and the mixture was stirred at room temperature for 12 hours. The resulting mixture was pured into water, and extracted with ethyl acetate. The organic layer was washed with brine, dried over anhydrous magnesium sulfate, and evaporated in vacuo. The residue was purified by column chromatography on silica gel (hexane:ethyl acetate=3:1) to give N-[(2S)-3-phenoxy-2-(triethyl-silyloxy)propyl]-N-[3-carbamoyloxy-6,7,8,9-tetrahydro-5H-benzocyclohepten-6-yl]-tert-butoxycarbonylamine (129 mg).

(+) APCI-MASS (m/z): 485 (M−Boc+2H)$^+$

Preparation 26

Under nitrogen, a mixture of 8-benzylamino-6,7,8,9-tetrahydro-5H-benzocyclohepten-2-ol (7.7 g) and di-tert-butyl dicarbonate (6.9 g) in tetrahydrofuran (80 ml) was stirred at room temperature for 12 hours. After evaporation, the residue was purified by column chromatography on silica gel (hexane:ethyl acetate=7:1) to give N-benzyl-N-(3-hydroxy-6,7,8,9-tetrahydro-5H-benzocyclohepten-6-yl)-tert-butoxycarbonylamine (10 g).

NMR (CDCl$_1$, δ): 1.1–1.7 (10H, m), 1.85–2.1 (3H, m), 2.45–2.7 (3H, m), 3.15–3.85 (2H, m), 4.3–4.7 (2H, m), 5.05–5.25 (1H, m), 6.3–6.6 (2H, m), 6.86 (2H, d, J=8.1 Hz), 7.15–7.4 (6H, m)

Preparation 27

To N-benzyl-N-[3-(3-cyanopyridin-2-yloxy)-6,7,8,9-tetrahydro-5H-benzocyclohepten-6-yl]-tert-butoxycarbonylamine (480 mg) was added 4N hydrogen chloride in ethyl acetate (5 ml) at room temperature, and the mixture was stirred at the same temperature for 1 hour. After evaporation in vacuo, the residue was dissolved into a mixture of saturated aqueous sodium hydrogencarbonate and ethyl acetate, followed by being made basic with saturated aqueous sodium hydrogencarbonate. After separation, the organic layer was washed with brine, dried over anhydrous magnesium sulfate and evaporated in vacuo to give 2-(8-benzylamino-6,7,8,9-tetrahydro-5H-benzocyclohepten-2-yl)oxy-3-cyanopyridine (339 mg).

(+) APCI-MASS (m/z): 370 (M+H)$^+$

The following compounds [Preparations 28 to 30] were obtained according to a similar manner to that of Preparation 27.

Preparation 28

N-Benzyl- [3-(2-methoxyethoxy)-6,7,8,9-tetrahydro-5H-benzocyclohepten-6-yl]amine (+) APCI-MASS (m/z): 326 (M+H)$^+$ Preparation 29

N-Benzyl-(3-phenyl-6,7,8,9-tetrahydro-5H-benzocyclohepten-6-yl)amine (+) APCI-MASS (m/z): 328 (M+H)$^+$ Preparation 30

N-Benzyl-(2-chloro-3-methoxy-6,7,8,9-tetrahydro-5H-benzocyclohepten-6-yl)amine (+) APCI-MASS (m/z): 316, 318 (M+H)$^+$ Preparation 31

Under nitrogen, to dimethylsulfoxide (5 ml) was added potassium hydroxide (34 mg) at room temperature, and the suspension was stirred at the same temperature for 40 minutes. To this one were added N-benzyl-N-(3-hydroxy-6,7,8,9-tetrahydro-5H-benzocyclohepten-6-yl)-tert-butoxycarbonylamine (200 mg) and 2-chloroethyl methyl ether (55 μl), and the mixture was stirred at room temperature for 4 hours. The resulting mixture was poured into saturated aqueous sodium hydrogencarbonate and extracted with ethyl acetate. The organic layer was washed with brine, dried over anhydrous magnesium sulfate, and evaporated in vacuo. The residue was purified by column chromatography on silica gel (hexane:ethyl acetate=10:1 to 5:1) to give N-benzyl-N-[3-(2-methoxyethoxy)-6,7,8,9-tetrahydro-5H-benzocyclohepten-6-yl]-tert-butoxycarbonylamine (213 mg).

(+) APCI-MASS (m/z): 326 (M−Boc+2H)$^+$

Preparation 32

A solution of 2-(8-benzylamino-6,7,8,9-tetrahydro-5H-benzocyclohepten-2-yloxy)acetic acid ethyl ester (320 mg) and 28% ammonium hydroxide (1 ml) in methanol (3 ml) was stirred at room temperature for 12 hours. The mixture was evaporated in vacuo to give 2-(8-benzylamino-6,7,8,9-tetrahydro-5H-benzocyclohepten-2-yloxy)acetamide (270 mg).

(+) APCI-MASS (m/z): 325 (M+H)$^+$

Preparation 33

Under nitrogen, to a suspension of sodium hydride (60% in oil, 300 mg) in N,N-dimethylformamide (20 ml) was added N-benzyl-N-(3-hydroxy-6,7,8,9-tetrahydro-5H-benzocyclohepten-6-yl)-tert-butoxycarbonylamine (2.5 g) in N,N-dimethylformamide (25 ml) at 5° C. After being stirred at room temperature for 30 minutes, to this one were added ethyl bromoacetate (0.75 ml) and tetra-n- butylammonium bromide (1.1 g) at 5° C., and the mixture was stirred at room temperature for 32 hours. The resulting mixture was poured into saturated aqueous sodium hydrogencarbonate and extracted with ethyl acetate. The organic layer was washed with brine, dried over anhydrous magnesium sulfate, and evaporated in vacuo. The residue was purified by column chromatography on silica gel (hexane:ethyl acetate=5:1) to give 2-[8-(N-benzyl-N-tert-butoxycarbonylamino)-6,7,8,9-tetrahydro-5H-benzocyclohepten-2-yloxy]acetic acid ethyl ester (1.6 g).

NMR (CDCl$_3$, δ): 1.1–1.7 (10H, m), 1.30 (3H, t, J=7.1 Hz), 1.85–2.2 (3H, m), 2.5–2.7 (3H, m), 3.2–3.4 (1H, m), 4.27 (2H, q, J=7.2Hz), 4.3–4.7 (2H, m), 4.54 (2H, s), 6.4–6.65 (2H, m), 6.93 (1H, d, J=8.3 Hz), 7.2–7.4 (5H, m)

(+) APCI-MASS (m/z): 354 (M−Boc+2H)$^+$

Preparation 34

To a solution of 2-[8-(N-benzyl-N-tert-butoxycarbonyl-amino)-6,7,8,9-tetrahydro-5H-benzocyclohepten-2-yloxy] acetic acid ethyl ester (1.6 g) in ethanol (16 ml) was added aqueous iN sodium hydroxide at 5° C., and the mixture was stirred at room temperature for 1 hour. After evaporation in vacuo, the residue was dissolved into a mixture of aqueous 0.1N hydrochloric acid and ethyl acetate. After separation, the organic layer was washed with brine, dried over anhydrous magnesium sulfate and evaporated in vacuo. The residue was triturated with hexane and dried in vacuo to give 2-[8-(N-benzyl-N-tert-butoxycarbonylamino)-6,7,8,9-tetrahydro-5H-benzocyclohepten-2-yloxy]acetic acid (1.3 g).

NMR (DMSO-d$_6$, δ): 1.1–1.7 (10H, m), 1.75–2.2 (3H, m), 2.45–2.7 (1H, m), 3.15–3.75 (4H, m), 4.3–4.7 (2H, m), 4.57 (2H, s), 6.4–6.7 (2H, m), 6.96 (1H, d, J=8.2 Hz), 7.2–7.5 (5H, m), 12.9 (1H, br s)

(+) APCI-MASS (m/z) 326 (M−Boc+2H)$^+$

Preparation 35

Under nitrogen, a solution of 2-[8-(N-benzyl-N-tert-butoxycarbonylamino)-6,7,8,9-tetrahydro-5H-benzocyclohepten-2-yloxy]acetic acid (300 mg) in dichloromethane (3 ml) were added 1-(3-dimethylaminopropyl)-3-ethylcarbodiimide hydrochloride (150 mg), dimethylamine hydrochloride (63 mg) and 4-dimethylaminopyridine (130 mg) at 5° C., and the mixture was stirred at room temperature for 12 hours. The resulting mixture was poured into 0.1N hydrochloric acid and extracted with ethyl acetate. The organic layer was successively washed with saturated aqueous sodium hydrogencarbonate and brine, dried over magnesium sulfate and evaporated in vacuo. The residue was purified by column chromatography on silica gel (hexane:ethyl acetate=1:1) to give N-benzyl-N-(3-N,N-dimethylcarbamoylmethoxy-6,7, 8,9-tetrahydro-5H-benzocyclohepten-6-yl)-tert-butoxycarbonylamine (312 mg).

NMR (CDCl$_3$, δ) 1.1–1.65 (10H, m), 1.85–2.15 (3H, m), 2.5–2.7 (4H, m), 2.98 (3H, s), 3.08 (3H, s), 3.2–3.45 (1H, m), 4.5–4.7 (2H, m), 4.60 (2H, s), 6.45–6.7 (2H, s), 6.93 (1H, d, J=8.2 Hz), 7.2–7.4 (5H, m)

(+) APCI-MASS (m/z) 353 (M−Boc+2H)$^+$

Preparation 36

To N-benzyl-N-(3-N,N-dimethylcarbamoylmethoxy-6,7, 8,9-tetrahydyro-5H-benzocyclohepten-6-yl)-tert-butoxycarbonylamine (279 mg) was added 4N hydrogen chloride in ethyl acetate (3 ml), and the mixture was stirred at room temperature for 1.5 hours. After evaporation in vacuo, the residue was dissolved into saturated aqueous sodium hydrogencarbonate and ethyl acetate, followed by separation. The organic layer was washed with brine, dried over anhydrous magnesium sulfate and evaporated in vacuo. A mixture of the residue and 10% palladium on activated carbon (50% wet, 100 mg) in methanol (5 ml) was stirred at room temperature in the presence of hydrogen at an atmospheric pressure for 7 hours. After filtration, the filtrate was evaporated in vacuo to give 2-(8-amino-6,7,8,9-tetrahydro-5H-benzocyclohepten-2-yloxy)-N,N-dimethylacetamide (137 mg).

NMR (CDCl$_3$, δ) 1.4–2.1 (4H, m), 2.65–3.15 (5H, m), 2.98 (3H, m), 3.09 (3H, s), 4.65 (2H, s), 6.68 (1H, dd, J=2.7 and 8.1 Hz), 6.77 (1H, d, J=2.7 Hz), 6.98 (1H, d, J=8.2 Hz)

(+) APCI-MASS (m/z): 263 (M+H)$^+$

Preparation 37

Under nitrogen, to a solution of 3-nitro-5,7,8,9-tetrahydrobenzocyclohepten-6-one (300 mg) in 1,2-dichloroethane (10 ml) were added benzylamine (0.24 ml), sodium triacetoxyborohydride (460 mg) and acetic acid (0.17 ml) at room temperature, and the mixture was stirred at the same temperature for 5 hours. The resulting mixture was poured into aqueous 1N sodium hydroxide and extracted with ethyl acetate. The organic layer was washed with brine, dried over anhydrous magnesium sulfate and evaporated in vacuo. The residue was purified by column chromatography on silica gel (hexane:ethyl acetate=2:1 to 1:5) to give N-benzyl-(3-nitro-6,7,8,9-tetrahydro-5H-benzocyclohepten-6-yl)amine (342 mg).

(+) APCI-MASS (m/z): 297 (M+H)$^+$

The following compound was obtained according to a similar manner to that of Preparation 37.

Preparation 38

N-Benzyl-(6,7,8,9-tetrahydro-5H-benzocyclohepten-6-yl)-amine (+) APCI-MASS (m/z): 252 (M+H)$^+$ Preparation 39

Under nitrogen, to the solution of 1-tetralone (16 g) in dichloromethane (80 ml) were added zinc(II) iodide (0.69 g) and trimethylsilyl cyanide (15 g) at room temperature, and the mixture was stirred at the same temperature for 3 hours. The resulting mixture was poured into saturated aqueous sodium hydrogencarbonate and extracted with ethyl acetate. The organic layer was successively washed with saturated aqueous sodium hydrogencarbonate and brine, dried over anhydrous magnesium sulfate and evaporated in vacuo to give crude 1-(trimethylsilyloxy)-1-cyano-1,2,3,4-tetrahydronaphthalene (27 g), which was successively used in the next reaction.

The following compounds [Preparations 40 and 41] were obtained according to a similar manner to that of Preparation 39.

Preparation 40

7-Methyl-1-trimethylsilyloxy-1-cyano-1,2,3,4-tetrahydronaphthalene

Preparation 41

7-Chloro-1-trimethylsilyloxy-1-cyano-1,2,3,4-tetrahydronaphthalene

Preparation 42

Under nitrogen, to the suspension of lithium aluminum hydride (8.4 g) in tetrahydrofuran (120 ml) was dropwise added 1-trimethylsilyloxy-1-cyano-1,2,3,4-tetrahydronaphthalene (27 g) in tetrahydrofuran (120 ml) at 5° C., and the mixture was stirred at room temperature for 24 hours. To the mixture were added sodium fluoride (37 g) and water (12 ml) at 5° C., and the mixture was vigorously stirred at room temperature for 30 minutes. The precipitate was removed by filtration. The filtrate was evaporated in vacuo to give 1-aminomethyl-1-hydroxy-1,2,3,4-tetrahydronaphthalene (19 g)

(+) APCI-MASS (m/z): 178 (M+H)$^+$

The following compounds [Preparations 43 and 44] were obtained according to a similar manner to that of Preparation 42.

Preparation 43

1-Aminomethyl-7-chloro-1-hydroxy-1,2,3,4-tetrahydronaphthalene

NMR (CDCl$_3$, δ): 1.8–2.2 (4H, m), 2.6–2.95 (4H, m), 7.00 (1H, d, J=8.2 Hz), 7.13 (1H, dd, J=2.3 and 8.2 Hz), 7.52 (1H, d, J=2.2 Hz)

Preparation 44

1-Aminomethyl-7-methyl-1-hydroxy-1,2,3,4-tetrahydronaphthalene

NMR (CDCl$_3$, δ): 1.5–2.2 (7H, m), 2.31 (3H, s), 2.6–2.9 (4H, m), 6.9–7.05 (2H, m), 7.32 (1H, s)

Preparation 45

To a solution of 1-aminomethyl-1-hydroxy-1,2,3,4-tetrahydronaphthalene (19 g) in 10% acetic acid in water (380 ml) was dropwise added sodium nitrite (11 g) in water (56 ml) at 5° C., and the mixture was stirred at the same temperature for 2 hours. The resulting mixture was diluted with ethyl acetate and separated. The organic layer was successively washed with water, saturated aqueous sodium hydrogencarbonate and brine, dried over anhydrous magnesium sulfate and evaporated in vacuo. The residue was purified. by column chromatography on silica gel (hexane-ethyl acetate) to give 5,7,8,9-tetrahydrobenzocyclohepten-6-one (9.3 g).

(+) APCI-MASS (m/z): 161 (M+H)$^+$

The following compounds [Preparations 46 and 47] were obtained according to a similar manner to that of Preparation 45.

Preparation 46

3-Chloro-5,7,8,9-tetrahydrobenzocyclohepten-6-one

NMR (CDCl$_3$, δ): 1.9–2.1 (2H, m), 2.57 (2H, t, J=7.0 Hz), 2.9–3.0 (2H, m), 3.68. (2H, s), 7.09 (1H, d, J=7.8 Hz), 7.16 (1H, s), 7.18 (1H, d, J=7.8 Hz)

Preparation 47

3-Methyl-5,7,8,9-tetrahydrobenzocyclohepten-6-one

NMR (CDCl$_3$, δ): 1.9–2.05 (2H, m), 2.30 (3H, s), 2.57 (2H, t, J=6.8 Hz), 2.85–2.95 (2H, m), 3.69 (2H, s), 6.95–7.1 (3H, m)

Preparation 48

A stirred solution of (2S)-1-phenoxy-2,3-epoxypropane (1.0 g) and concentrated ammonium hydroxide (10 ml) in ethanol (10 ml) was sealed up at room temperature for 12 hours. The mixture was evaporated in vacuo and dried to give (2S)-1-amino-3-phenoxy-2-propanol (1.1 g).

(+) APCI-MASS (m/z): 168 (M+H)$^+$

Preparation 49

To a mixture of N-benzyl-N-(3-hydroxy-6,7,8,9-tetrahydro-5H-benzocyclohepten-6-yl)-tert-butoxycarbonylamine (1.01 g), 2,6-lutidine (0.38 ml) and N,N-dimethylaminopyridine (0.067 g) in dichloromethane (20 ml) was added dropwise trifluoromethanesulfonic anhydride (0.51 ml) at −30° C. The mixture was warmed to room temperature over 3 hours and then washed with water, dried over magnesium sulfate and evaporated in vacuo. The residue was purified by column chromatography on silica gel eluting with a mixture of hexane and ethyl acetate (20:1) to afford N-benzyl-N-tert-butoxycarbonyl-(3-trifluoromethylsulfonyloxy-6,7,8,9-tetrahydro-5H-benzocyclohepten-6-yl)amine (0.98 g).

NMR (DMSO-d$_6$, δ): 1.14–1.50 (11H, m), 1.80–2.15 (3H, m), 2.60–2.80 (3H, m), 3.30–3.60 (1H, m), 4.25–4.62 (2H, m), 6.98–7.50 (8H, m)

(+) ESI-MASS (m/z): 522 (M+Na)$^+$

Preparation 50

To a suspension of N-benzyl-N-tert-butoxycarbonyl-(3-trifluoromethoxy-6,7,8,9-tetrahydro-5H-benzocyclohepten-6-yl)amine (500 mg) in toluene (6 ml) and water (2 ml) were added phenylboronic acid (122 mg), sodium carbonate (210 mg) and tetrakis(triphenylphosphine)palladium(0) (35 mg), and the mixture was stirred at 80° C. for 3.5 hours. The resulting mixture was poured into water and extracted with ethyl acetate. The organic layer was washed with brine, dried over anhydrous magnesium sulfate and evaporated in vacuo. The residue was purified by column chromatography on silica gel (hexane:ethyl acetate=30:1 to 20:1) to give N-benzyl-N-(3-phenyl-6,7,8,9-tetrahydro-5H-benzocyclohepten-6-yl)-tert-butoxycarbonylamine (494 mg).

(+) ESI-MASS (m/z): 450 (M+Na)$^+$

Preparation 51

Under nitrogen, a suspension of N-benzyl-N-(3-hydroxy-6,7,8,9-tetrahydro-5H-benzocyclohepten-6-yl)-tert-butoxycarbonylamine (300 mg) and N-chlorosuccinamide (110 mg) in 1,4-dioxane (5 ml) was stirred at 10020 C. for 9 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (toluene:ethyl acetate=50:1 to 10:1) to give N-benzyl-N-(2-chloro-3-hydroxy-6,7,8,9-tetrahydro-5H-benzocyclohepten-6-yl)-tert-butoxycarbonylamine (152 mg) .

(+) APCI-MASS (m/z): 302, 304 (M−Boc+2H)$^+$

Preparation 52

Under nitrogen, to a solution of (2R)-1-tosyloxy-2,3-epoxypropane (3.0 g) in tetrahydrofuran (30 ml) were added N,N-diisopropylethylamine (2.5 ml) and thiophenol (1.3 ml) at 5° C., and the mixture was stirred at room temperature for 12 hours. The resulting mixture was poured into water and extracted with ethyl acetate. The organic layer was successively washed with saturated aqueous sodium hydrogencarbonate and brine, dried over anhydrous magnesium sulfate and evaporated in vacuo. The residue was purified by column chromatography on silica gel (hexane:ethyl acetate= 5:1 to 3:1) to give (2S)-3-phenylthio-1-tosyloxy-2-propanol (3.9 g).

NMR (CDCl$_3$, δ): 2.44 (3H, m), 2.75–3.25 (3H, m), 3.85–4.3 (3H, m), 7.15–7.4 (7H, m), 7.7–7.8 (2H, m)

Preparation 53

Under nitrogen, to a solution of (2S)-3-phenylthio-1-tosyloxy-2-propanol (3.9 g) in ethanol (40 ml) was added 20% sodium methoxide in ethanol (4.7 ml) at 5° C., and the mixture was stirred at the same temperature for 30 minutes. After being filtrated off to remove precipitates, the filtrate was concentrated in vacuo. The residue was dissolved into a mixture of aqueous 0.1N sodium hydroxide and diethyl ether. After separation, the organic layer was successively washed with water and brine, dried over anhydrous magnesium sulfate and evaporated in vacuo. The residue was purified by column chromatography on silica gel (hexane:ethyl acetate=20:1 to 10:1) to give (2S)-1-phenylthio-2,3-epoxypropane (1.5 g).

(+) APCI-MASS (m/z): 167 (M+H)$^+$

Preparation 54

Under nitrogen, to a solution of allylphenylamine (3 ml) in dichloromethane (30 ml) were added pyridine (2.1 ml) and benzyl chloroformate (3.5 ml) at 5° C., and the mixture was stirred at the same temperature for 3 hours. The resulting mixture was poured into aqueous 1N hydrogen chloride and extracted with ethyl acetate. The organic layer was successively washed with saturated aqueous sodium hydrogencarbonate and brine, dried over anhydrous magnesium sulfate and evaporated in vacuo. The residue was purified by column chromatography on silica gel (hexane:ethyl acetate= 20:1 to 10:1) to give N-allyl-N-phenylbenzyloxycarbonylamine (5.5 g).

(+) APCI-MASS (m/z): 268 (M+H)+

Preparation 55

Under nitrogen, to a solution of N-allyl-N-phenylbenzyloxycarbonylamine (5.5 g) in dichloromethane (50 ml) was added m-chloroperbenzoic acid (3.9 g) at 5° C., and the mixture was stirred at room temperature for 3 days. The resulting mixture was poured into aqueous sodium hydrogensulfite and extracted with ethyl acetate. The organic layer was successively washed with saturated aqueous sodium hydrogencarbonate and brine, dried over anhydrous magnesium sulfate and evaporated in vacuo. The residue was purified by column chromatography on silica gel (hexane:ethyl acetate=10:1 to 5:1) to give 1-(N-benzyloxycarbonyl-N-phenylamino)-2,3-epoxypropane (2.2 g).

(+) APCI-MASS (m/z): 284 (M+H)+

Preparation 56

To a suspension of but-3-butenylbenzene (3 ml) and sodium hydrogen carbonate (2.5 g) in a mixture of dichloromethane (200 ml) and water (60 ml) was added small portions of m-chloroperbenzoic acid (3.5 g) at room temperature, and the mixture was stirred at the same temperature for 4 hours. After separation, the organic layer was successively washed with saturated aqueous sodium hydrogencarbonate and brine, dried over anhydrous magnesium sulfate and evaporated in vacuo. The residue was purified by column chromatography on silica gel (hexane:ethyl acetate= 100:3) to give 2-phenethyloxirane (970 mg).

NMR (CDCl$_3$, δ): 1.7–1.9 (2H, m), 2.45–2.5 (1H, m), 2.7–3.0 (4H, m), 7.1–7.4 (5H, m)

Preparation 57

A mixture of N-benzyl-(3-methoxy-6,7,8,9-tetrahydro-5H-5 benzocyclohepten-6-yl)amine (1.0 g) and 10% palladium on activated carbon (50% wet, 300 mg) in methanol (10 ml) was stirred at room temperature in the presence of hydrogen at an atmospheric pressure for 5.5 hours. After filtration, the filtrate was evaporated in vacuo to give 3-methoxy-(6,7,8,9-tetrahydro-5H-benzocyclohepten-6-yl) amine (720 mg).

NMR (CDCl$_3$, δ): 1.4–1.6 (1H, m), 1.7–2.0 (2H, m), 2.1–2.3 (1H, m), 2.7–2.75 (2H, m), 2.85–3.3 (3H, m), 3.76 (3H, s), 6.66 (1H, dd, J=2.7 and 8.2 Hz), 6.76 (1H, d, J=2.6 Hz), 7.00 (1H, d, J=8.2 Hz)

The following compounds [Preparation 58 and 59] were obtained according to a similar manner to that of Preparation 57.

Preparation 58

2-(8-Amino-6,7,8,9-tetrahydro-5H-benzocyclohepten-2-yloxy)acetic acid tert-butyl ester NMR (CDCl$_3$, δ) 1.3–2.1 (4H, m), 1.49 (9H, s), 2.65–3.1 (5H, m), 4.48 (2H, m), 6.61 (1H, dd, J=2.7 and 8.2 Hz), 6.73 (1H, d, J=2.7 Hz), 6.98 (1H, d, J=8.2 Hz)

Preparation 59

2-(8-Amino-6,7,8,9-tetrahydro-5H-benzocyclohepten-2-yloxy)-N-phenylacetamide

NMR (CDCl$_3$, δ): 1.45–2.15 (4H, m), 2.7–3.1 (5H, m), 4.58 (2H, m), 6.72 (1H, dd, J=2.7 and 8.2 Hz), 6.83 (1H, d, J=2.7 Hz), 7.04 (1H, d, J=8.2 Hz), 7.1–7.25 (1H, m), 7.3–7.4 (2H, m), 7.55–7.7 (2H, m), 8.30 (1H, br s)

(+) ESI-MASS (m/z): 311 (M+H)+

Preparation 60

To a solution of N-benzyl-N-(3-hydroxy-6,7,8,9-tetrahydro-5H-benzocyclohepten-6-yl)-tert-butoxycarbonylamine (500 mg) in ethyl acetate (5 ml) was added 4N hydrogen chloride in ethyl acetate (5 ml) at room temperature, and the mixture was stirred at the same temperature for 1 hour. The mixture was poured into a mixture of saturated aqueous sodium hydrogencarbonate and ethyl acetate, followed by being made basic with saturated aqueous sodium hydrogencarbonate. After separation, the organic layer was dried over anhydrous magnesium sulfate and evaporated in vacuo to give crude 8-benzylamino-6,7, 8,9-tetrahydro-5H-benzocyclohepten-2-ol.

Under nitrogen, to a suspension of sodium hydride (60% in oil, 60 mg) in N,N-dimethylformamide (3 ml) was added above obtained one in N,N-dimethylformamide (4 ml) at 5° C. After being stirred at room temperature for 30 minutes, to this one were added tert-butyl bromoacetate (0.22 ml) and tetra-n-butylammonium bromide (220 mg) at 5° C., and the mixture was stirred at room temperature for 6 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (chloroform:methanol=50:1 to 20:1) to give 2-(8-benzylamino-6,7,8,9-tetrahydro-5H-benzocyclohepten-2-yloxy) acetic acid tert-butyl ester (474 mg)

(+) APCI-MASS (m/z): 382 (M+H)+

Preparation 61

A mixture of 6-(4-nitrophenylazo)pyridin-3-ol (300 mg) and 20% palladium hydroxide on carbon (60 mg) in a mixture of acetic acid (30 ml) and methanol (30 ml) was stirred at room temperature in the presence of hydrogen at an atmospheric pressure for 70 minutes. After filtration, the filtrate was evaporated in vacuo. Under nitrogen, to a mixture of the residue in dichloromethane (10 ml) was added bis(trimethylsilyl)acetamido (6.0 ml) at 5° C. After being stirred at room temperature for 30 minutes, to this one was added benzyl chloroformate (0.54 ml) at 5° C., and the mixture was stirred at the same temperature for 3 hours. The resulting mixture was poured into saturated aqueous sodium hydrogencarbonate and extracted with ethyl acetate. The organic layer was washed with brine, dried over anhydrous magnesium sulfate and evaporated in vacuo. To the residue was added chloroform, and insoluble materials were filtered off. After the filtrate was evaporated in vacuo, the residue was purified by column chromatography on silica gel (chloroform:methanol=50:1 to 20:1), followed by crystallization from toluene-methanol to give 2-benzyloxycarbonylamino-5-hydroxypyridine (159 mg).

(+) APCI-MASS (m/z): 245 (M+H)+

Preparation 62

Under nitrogen, to a suspension of sodium hydride (60% in oil, 189 mg) in N,N-dimethylformamide (20 ml) was dropwise added 2-benzyloxycarbonylamino-5-hydroxypyridine (1.1 g) in N,N-dimethylformamide (12 ml) at 5° C., and the mixture was stirred at room temperature for 1 hour. To this one was added (2S)-(+)-1-tosyloxy-2,3-epoxypropane (1.1 g) at 5° C., and the mixture was stirred at room temperature for 7 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (chloroform:ethyl acetate=9:1) to give 2-benzyloxycarbonylamino-5-[(2S)-oxiranylmethoxy]pyridine (780 mg).

(+) APCI-MASS (m/z): 301 (M+H)+

Preparation 63

To a mixture of 8-methoxy-1-tetralone (2.66 g) and zinc iodide (0.096 g) in dichloromethane (13 ml) was dropwise added trimethylsilylcyanide (2.65 ml) under a nitrogen atmosphere. The reaction mixture was stirred at room temperature overnight and then poured into a saturated aqueous sodium bicarbonate solution. The product was extracted with ethyl acetate, and the extract was washed with a saturated aqueous sodium bicarbonate solution and brine, dried over magnesium sulfate, and evaporated in vacuo. The residue was purified by column chromatography on silica gel eluting with a mixture of hexane and ethyl acetate (4:1) to afford 1-cyano-8-methoxy-1-trimethylsilyloxy-1,2,3,4-tetrahydronaphthalene (3.64 g).

NMR (DMSO-$d_6$, δ): 0.15 (9H, s), 1.70–1.81 (2H, m), 2.09–2.38 (2H, m), 2.70–2.77 (2H, m), 3.84 (3H, s), 6.76 (1H, d, J=8.0 Hz), 6.92 (1H, d, J=8.0 Hz), 7.29 (1H, d, J=8.0, 8.0 Hz)

(+) ESI-MASS (m/z): 298 (M+Na)+

Preparation 64

To a mixture of lithiumaluminumhydride (0.99 g) in tetrahydrofuran (18 ml) was added dropwise a solution of 1-cyano-8-methoxy-1-trimethylsilyloxy-1,2,3,4-tetrahydronaphthalene (3.59 g) in tetrahydrofuran (18 ml) under ice-cooling and a nitrogen atmosphere. After stirring at room temperature for 3 hours, sodium fluoride (1.09 g) and water (1.41 ml) were added to the reaction mixture under ice-cooling. After stirring for additional 30 minutes, insoluble materials were filtered off and washed with 5% ethanol in ethyl acetate. The filtrate was evaporated in vacuo to afford 1-aminomethyl-1-hydroxy-8-methoxy-1,2,3,4-tetrahydronaphthalene (2.60 g), which was used in the next step without purification.

NMR (DMSO-$d_6$, δ): 1.38–1.72 (3H, m), 2.07–2.14 (1H, m), 2.62–2.91 (6H, m), 3.77 (3H, s), 6.68 (1H, d, J=7.8 Hz), 6.80 (1H, d, J=7.8 Hz), 7.09 (1H, dd, J=7.8, 7.8 Hz)

(+) ESI-MASS (m/z): 190 (M−OH)+

Preparation 65

To a suspension of l-aminomethyl-1-hydroxy-8-methoxy-1,2,3,4-tetrahydronaphthalene (2.54 g) in 10% acetic acid was added dropwise a solution of sodium nitrite (1.27 g) in water (6.4 ml) under ice-cooling. The mixture was stirred at the same temperature for 2 hours and then partitioned between ethyl acetate and water. The organic layer was separated, washed with an aqueous sodium bicarbonate solution and brine, dried over magnesium sulfate and evaporated in vacuo. The residue was purified by column chromatography on silica gel eluting with a mixture of hexane and ethyl acetate (10:1) to afford 4-methoxy-6,7,8,9-tetrahydro-5H-benzocyclohepten-6-one (1.08 g).

NMR (DMSO-$d_6$, δ): 1.77–1.91 (2H, m), 2.47 (2H, t, J=7.0 Hz), 2.85–2.92 (2H, m), 3.76 (3H, s), 3.76 (2H, s), 6.76 (1H, d, J=7.5 Hz), 6.88 (1H, d, J=7.5 Hz), 7.16 (1H, dd, J=7.5 and 7.5 Hz)

(+) ESI-MASS (m/z): 213 (M+Na)+

Preparation 66

A solution of 4-methoxy-6,7,8,9-tetrahydro-5H-benzocyclohepten-6-one (500 mg) and benzylamine (0.29 ml) in the presence of catalytic amounts of p-toluenesulfonic acid monohydrate in toluene (5 ml) was refluxed for 2 hours to remove water as the toluene azeotrope, and then the mixture was evaporated in vacuo. To the solution of the residue in methanol (5 ml) was added sodium borohydride (99 mg) under nitrogen at 5° C., and the mixture was stirred at room temperature for 12 hours. After the resulting mixture was evaporated in vacuo, the residue was dissolved into ice-cold water and ethyl acetate. After separation, the organic layer was washed successively with water and brine, dried over anhydrous magnesium sulfate and evaporated in vacuo. The residue was purified by column chromatography on silica gel (hexane:ethyl acetate=5:1 to 1:1) to give N-benzyl-(4-methoxy-6,7,8,9-tetrahydro-5H-benzocyclohepten-6-yl)amine (660 mg).

NMR (DMSO-$d_6$, δ): 1.17–1.37 (1H, m), 1.53–2.02 (3H, m), 2.25–2.38 (1H, m), 2.50–3.80 (3H, m), 3.26–3.32 (2H, m), 3.67–3.86 (2H, m), 3.77 (3H, s), 6.68 (1H, d, J=7.5 Hz), 6.79 (1H, d, J=7.5 Hz), 7.01 (1H, dd, J=7.5 and 7.5 Hz), 7.17–7.30 (5H, m)

(+) ESI-MASS (m/z): 282 (M+H)+

Preparation 67

Into a mixture of N-benzyl-N-(3-trifluoromethyl-sulfonyloxy-6,7,8,9-tetrahydro-5H-benzocyclohepten-6-yl)-tert-butoxycarbonylamine (0.94 g), palladium acetate (0.084 g), 1,3-bis(diphenylphosphino)propane (0.16 g), triethylamine (0.79 ml) in methanol (2.8 ml) and N,N-dimethylformamide (7 ml) was introduced carbon oxide gas at room temperature for 1 hour. Then the mixture was heated at 75° C. for 2.5 hours with carbon oxide gas bubbling. After cooling, the reaction mixture was partitioned between water and ethyl acetate. The organic layer was separated, washed with water (twice) and brine, dried over magnesium sulfate and evaporated in vacuo. The residue was purified by column chromatography on silica gel eluting with a mixture of hexane and ethyl acetate (10:1) to afford 8-(N-benzyl-N-tert-butoxycarbonylamino)-6,7,8,9-tetrahydro-5H-benzocyclohepten-2-carboxylic acid methyl ester (0.76 g).

NMR (DMSO-$d_6$, δ) 1.13–1.50 (11H, m), 1.79–2.13 (3H, m), 2.58–2.79 (3H, m), 3.44–3.74 (1H, m), 3.83 (3H, s), 4.30–4.62 (2H, m), 7.20–7.38 (6H, m), 7.50–7.60 (1H, m), 7.67 (1H, d, J=7.7 Hz)

(+) ESI-MASS (m/z): 432 (M+Na)+

Preparation 68

To a solution of 8-(N-benzyl-N-tert-butoxycarbonylamino)-6,7,8,9-tetrahydro-5H-benzocycloheptene-2-carboxylic acid methyl ester (10.07 g) in dichloromethane (100 ml) was added trifluoroacetic acid (9.47 ml), and the mixture was stirred at room temperature overnight. The mixture was evaporated in vacuo and partitioned between ethyl acetate and an aqueous sodium bicarbonate solution. The organic layer was separated, washed with water and brine, dried over magnesium sulfate and evaporated in vacuo. The residue was purified by column chromatography on silica gel eluting with a mixture of chloroform and methanol (20:1) to afford 8-benzylamino-6,7,8,9-tetrahydro-5H-benzocycloheptene-2-carboxylic acid methyl ester (7.78 g).

NMR (DMSO-$d_6$, δ) 1.24–1.43 (1H, m), 1.59–2.08 (4H, m), 2.42–2.50 (1H, m), 2.76–3.03 (4H, m), 3.75 (2H, d, J=3.1 Hz), 3.83 (3H, s), 7.16–7.36 (6H, m), 7.67 (1H, dd, J=7.7, 1.8 Hz), 7.75 (1H, d, J=1.8 Hz)

(+) ESI-MASS (m/z) 310 (M+H)+

Preparation 69

To a mixture of 8-[N-tert-butoxycarbonyl-N-[(2S)-2-hydroxy-3-phenoxpropyl]amino]-6,7,8,9-tetrahydro-5H-benzocycloheptene-2-carboxylic acid methyl ester (4.80 g), imidazole (1.68 g) and catalytic amount of N,N-dimethylaminopyridine in N,N-dimethylformamide (100 ml) was added triethylsilyl chloride (3.82 ml) under ice-cooling. The reaction mixture was stirred at room temperature for 6 hours and partitioned between ethyl acetate and aqueous sodium bicarbonate solution. The organic layer was separated, washed with water (twice) and brine, dried over magnesium sulfate and evaporated in vacuo. The residue was purified by column chromatography on silica gel eluting with a mixture of hexane and ethyl acetate (20:1) to afford 8-(N-tert-butoxycarbonyl-N-[(2S)-3-phenoxy-2-(triethylsilyloxy)-propyl]amino)-6,7,8,9-tetrahydro-5H-benzocycloheptene-2-carboxylic acid methyl ester (6.07 g).

NMR (DMSO-$d_6$, δ): 0.50–0.67 (6H, m), 0.83–0.95 (9H, m), 1.13–1.37 (1H, m), 1.42 (9H, s), 1.89–2.22 (3H, m), 2.68–2.98 (3H, m), 3.20–3.48 (4H, m), 3.81, 3.83 (total 3H, s), 3.83–3.92 (1H, m), 3.97–4.07 (1H, m), 4.20–4.37 (1H, m), 6.86–6.97 (3H, m), 7.18–7.34 (3H, m), 7.68–7.75 (2H, m)

(+) APCI-MASS (m/z): 484 (M−Boc+2H)$^+$

Preparation 70

To a cold (−78° C.) solution of 8-[N-tert-butoxycarbonyl-N-[(2S)-3-phenoxy-2-(triethylsilyloxy)propyl]amino]-6,7,8,9-tetrahydro-5H-benzocycloheptene-2-carboxylic acid methyl ester (5.90 g) in tetrahydrofuran (120 ml) was added dropwise a solution of diisobutylaluminum hydride in hexane (0.95M, 53.2 ml). The reaction mixture was warmed to room temperature over 4 hours, and then saturated sodium bicarbonate solution was added dropwise to the mixture. The resulting precipitate was filtered off and washed with ethyl acetate. The filtrate was extracted with ethyl acetate, and the organic layer was washed with water and brine, dried over magnesium sulfate and evaporated in vacuo. The residue was purified by column chromatography on silica gel eluting with a mixture of hexane and ethyl acetate (5:1) to afford N-(3-hydroxymethyl-6,7,8,9-tetrahydro-5H-benzocyclohepten-6-yl)-N-[(2S)-3-phenoxy-2-(triethylsilyloxy)propyl]-tert-butoxy-carbonylamine (5.20 g).

NMR (DMSO-$d_6$, δ): 0.52–0.68 (6H, m), 0.85–0.97 (9H, m), 1.08–1.38 (1H, m), 1.41 (9H, s), 1.80–2.20 (3H, m), 2.50–2.88 (3H, m), 3.15–3.52 (4H, m), 3.80–3.90 (1H, m), 3.94–4.05 (1H, m), 4.22–4.40 (1H, m), 4.41 (2H, d, J=4.5 Hz), 5.06 (1H, t, J=4.5 Hz), 6.83–7.03 (6H, m), 7.30 (2H, dd, J=7.4 and 7.4 Hz)

(+) APCI-MASS (m/z): 456 (M−Boc+2H)$^+$

Preparation 71

To a mixture of N-(3-hydroxymethyl-6,7,8,9-tetrahydro-5H-benzocyclohepten-6-yl)-N-[(2S)-3-phenoxy-2-(triethylsilyl-oxy)propyl]-tert-butoxycarbonylamine (1.93 g) and triethylamine (0.58 ml) in dichloromethane (40 ml) was added dropwise methanesulfonyl chloride (0.27 ml) under ice-cooling. After stirring at room temperature for 6 hours, the reaction mixture was washed successively with water, sodium bicarbonate solution, water and brine. The organic layer was dried over magnesium sulfate and evaporated in vacuo to afford crude N-[(2S)-3-phenoxy-2-(triethylsilyloxy)propyl]-N-(3-methylsulfonyloxymethyl-6,7,8,9-tetrahydro-5H-benzocyclohepten-6-yl]-tert-butoxycarbonylamine (2.18 g) which was used without purification.

Preparation 72

To a solution of N-tert-butoxycarbonyl-N-[(2S)-3-phenoxy-2-(triethylsilyloxy)propyl]-(3-N,N-dimethylamino-methyl-6,7,8,9-tetrahydro-5H-benzocyclohepten-6-yl) amine (0.60 g) in tetrahydrofuran (3 ml) was added a solution of dimethylamine in tetrahydrofuran (2M, 1.89 ml) under ice-cooling. The mixture was stirred at room temperature overnight and then partitioned between water and ethyl acetate. The organic layer was separated, washed with water and brine, dried over magnesium sulfate and evaporated in vacuo. The residue was purified by column chromatography on silica gel eluting with a mixture of chloroform and methanol (50:1 to 20:1) to afford N-(3-N,N-dimethylaminomethyl-6,7,8,9-tetrahydro-5H-benzocyclohepten-6-yl)-N-[(2S)-3-phenoxy-2-(triethylsilyloxy)propyl]-tert-butoxycarbononylamine (0.41 g).

NMR (DMSO-$d_6$, δ): 0.43–0.67 (6H, m), 0.82–0.98 (9H, m), 1.10–1.35 (1H, m), 1.41 (9H, s), 1.81–2.08 (3H, m), 2.11 (6H, s), 2.50–2.90 (3H, m), 3.17–3.58 (5H, m), 3.78–4.22 (4H, m), 6.87–7.04 (6H, m), 7.22–7.34 (2H, m) (0.41 g).

(+) APCI-MASS (m/z): 583 (M+H)$^+$

Preparation 73

A mixture of 8-benzylamino-6,7,8,9-tetrahydro-5H-benzocycloheptene-2-carboxylic acid methyl ester (4.21 g) and sodium methoxide (2.21 g) in formamide (42 ml) was heated at 110° C. for 2 hours. After cooling, the reaction mixture was poured into water, and the product was extracted with ethyl acetate. The organic layer was washed with water (twice) and brine, dried over magnesium sulfate and evaporated in vacuo. The residue was purified by column chromatography on silica gel eluting with a mixture of chloroform and methanol (30:1 to 10:1) to afford 8-benzylamino-6,7,8,9-tetrahydro-5H-benzocycloheptene-2-carboxamide (2.71 g).

NMR (DMSO-$d_6$, δ): 1.24–1.42 (1H, m), 1.59–2.05 (4H, m), 2.40–2.50 (1H, m), 2.70–3.01 (4H, m), 3.67–3.84 (2H, m), 7.13 (1H, d, J=7.7 Hz), 7.18–7.36 (6H, m), 7.59 (1H, dd, J=7.7 and 1.8 Hz), 7.70 (1H, d, J=1.8 Hz), 7.86 (1H, s)

(+) APCI-MASS (m/z): 295 (M+H)$^+$

Preparation 74

To a solution of (R)-4-(3-toluenesulfonyloxy-2-hydroxy)propyl-1-benzyloxybenzene (110 mg) in acetonitrile (10 ml), a solution of nitronium tetrafluoroborate (536 mg) in acetonitrile (10 ml) was added dropwise with ice-bath cooling. The reaction mixture was stirred for 0.5 hour and worked up in a usual manner. The crude product was purified by a column chromatography (SiO$_2$ 50 cm$^3$, eluent; 33% ethyl acetate-hexane) to give (R)-1-(3-toluenesulfonyloxy-2-hydroxy)propyl-3-nitro-4-benzyloxybenzene (259 mg) as an oil.

IR (Film) 1623, 1533, 1356, 1267, 1174, 1095, 984, 816 cm$^{-1}$

NMR (CDCl$_3$, δ): 2.17 (1H, d, J=4.4 Hz), 2.46 (3H, s), 2.7–2.8 (2H, m), 3.9–4.2 (3H, m), 5.21 (2H, s), 7.06 (1H, t, J=8.7 Hz), 7.3–7.5 (7H, m), 7.66 (1H, d, J=2.1 Hz), 7.7–7.9 (3H, m)

Preparation 75

To a solution of 4-benzyloxybromobenzene (263 mg) in dry tetrahydrofuran (3 ml), butyllithium (1.54M hexane solution, 0.71 ml) was added dropwise at −78° C. under nitrogen, and the resulting mixture was stirred for 30 minutes. To the reaction mixture, boranetrifluoride diethyl ether (123 μl), and a solution of (R)-1-tosyloxy-2,3-epoxypropane (202 mg) in dry tetrahydrofuran (1 ml) were added below −50° C. The reaction mixture was worked up in a usual manner and purified by a column chromatography (SiO$_2$ 40 cm$^3$, 25% ethyl acetate-hexane) to give (R)-4-(3-toluenesulfonyloxy-2-hydroxy)propyl-1-benzyloxybenzene (144 mg) as an oil.

IR (Film) 1512, 1360, 1240, 1178, 978, 833, 814 cm$^{-1}$

NMR (CDCl$_3$, δ): 2.04 (1H, d, J=4.4 Hz), 2.45 (3H, s), 2.72 (2H, d, J=5.3 Hz), 3.9–4.1 (3H, m), 5.04 (2H, s), 6.89 (2H, d, J=8.7 Hz), 7.06 (2H, d, J=8.7 Hz), 7.3–7.5 (7H, m), 7.7–7.9 (3H, m)

Preparation 76

A mixture of (R)-1-(3-toluenesulfonyloxy-2-hydroxy)propyl-3-nitro-4-benzyloxybenzene (26 mg), iron powder, ammonium chloride (2.6 mg) and wet ethanol (0.5 ml) was heated at 80° C. for 1 hour and 20 minutes, filtered and worked up in the usual manner. The residue was treated with small amounts of potassium carbonate in methanol and worked up in the usual manner to give epoxide. The crude epoxide was dissolved in dichloromethane, treated with triethylamine followed by methanesulfonyl chloride, worked up in the usual manner and purified by preparative TLC (SiO$_2$, 50% ethyl acetate-hexane) to give (R)-1-(3-methanesulfonylamino-4-benzyloxy)phenyl-2,3-epoxypropane (10.8 mg) as an oil.

IR (Film) 2931, 1612, 1508, 1365, 1321, 1270, 1160, 975, 924 cm$^{-1}$

NMR (CDCl$_3$, δ): 2.50 (1H, dd, J=2.6 and 4.9 Hz), 2.7–3.0 (3H, m), 2.89 (3H, s), 3.1–3.2 (1H, m), 5.14 (2H, s), 7.02 (1H, d, J=8.4 Hz), 7.24 (1H, dd, J=2.2 and 9.6 Hz), 7.3–7.6 (6H, m)

Preparation 77

Under nitrogen, to a solution of 4-acetylaminophenol (569 mg) and sodium hydride (150 mg) in N,N-dimethylformamide (30 ml) was added (2S)-(+)-1-tosyloxy-2,3-epoxypropane (1.0 g) at 0° C., and the mixture was stirred at the same temperature for 0.5 hour. The mixture was allowed to warm to room temperature and stirred for 3 hours at this temperature. The resulting mixture was poured into 10% aqueous ammonium chloride solution and extracted with ethyl acetate. The organic layer was washed with brine, dried over magnesium sulfate and evaporated in vacuo. The residue was chromatographed (hexane-ethyl acetate) over silica gel to afford (2S)-1-(4-acetylamino)phenoxy-2,3-epoxypropane (285 mg).

(+) APCI-MASS (m/z): 149 (M+Na)$^+$

Preparation 78

Under nitrogen, to a solution of 2,3-dimethylbenzene-1,4-diol (25.0 g) and potassium hydroxide (40.6 g) in dimethylsulfoxide (100 ml) was added iodomethane (17 ml) at room temperature, and the mixture was stirred for 3 hours at this temperature. The resulting mixture was poured into water and extracted with ethyl acetate. The organic layer was washed with brine, dried over magnesium sulfate and evaporated in vacuo to afford 1,4-dimethoxy-2,3-dimethylbenzene (23.16 g).

(+) APCI-MASS (m/z): 167 (M+H)$^+$

Preparation 79

A solution of 1,4-dimethoxy-2,3-dimethylbenzene (23.16 g), benzoyl peroxide (673 mg) and N-bromosuccinimide (52.0 g) in carbontetrachloride (140 ml) was refluxed for 4 hours and filtered. The filtrate was evaporated in vacuo. The residue was chromatographed (hexane-ethyl acetate) over silica gel to afford 2,3-dibromomethyl-1,4-dimethoxybenzene (8.17 g).

(+) APCI-MASS (m/z): 325 (M+H)$^+$

Preparation 80

To a solution of N-isopropylcyclohexylamine (3.52 ml) in tetrahydrofuran (10 ml) was added 1M n-butyllithium in hexane (13.8 ml). After being stirred for 20 minutes at this temperature, the solution was treated dropwise with tert-butyl acetate (2.96 ml). And after stirred for 20 minutes, a solution of 2,3-dibromomethyl-1,4-dimethoxybenzene (2.73 g) in tetrahydrofuran (10 ml) was added below −68° C. After all had been introduced, the mixture was allowed to warm to −23° C. and stirred for 2.5 hours at this temperature. The resulting mixture was added dropwise to 1N hydrochloric acid (10 ml) with stirring under ice-cooling over 30 minutes and extracted with ethyl acetate. The organic layer was washed with brine, dried over magnesium sulfate and evaporated in vacuo. The residue was chromatographed (hexane-ethyl acetate) over silica gel to afford 3-[2-(2-tert-butoxycarbonylethyl)-3,6-dimethoxyphenyl]propionic acid tert-butyl ester (2.69 g).

NMR (CDCl$_3$, δ): 1.47 (18H, s), 2.29–2.43 (4H, m), 2.88–2.96 (4H, m), 3.75 (6H, s), 6.66 (2H, s)

Preparation 81

3-[2-(2-tert-butoxycarbonylethyl)-3,6-dimethoxyphenyl]-propionic acid tert-butyl ester (6.33 g) was added dropwise to a refluxed solution of sodium hydride (578 mg) in dry toluene (60 ml) and dry tert-butyl alcohol (0.5 ml), and stirred for 3 hours. After cooling, to the reaction mixture glacial acetic acid was added dropwise followed by addition of ice water and extracted with ethyl acetate. The organic layer was washed with brine, dried over magnesium sulfate and evaporated in vacuo. To the residue were added methanol (50 ml) and 6N hydrochloric acid (15 ml), and this mixture was refluxed for 3 hours, poured into ice and extracted with ethyl acetate. The residue was chromatographed (hexane-ethyl acetate) over silica gel to afford 1,4-dimethoxy-5,6,8,9-tetrahydrobenzocyclohepten-7-one (2.99 g).

MASS (m/z): 221 (M+H)$^+$

Preparation 82

A solution of 1,4-dimethoxy-5,6,8,9-tetrahydrobenzo-cyclohepten-7-one (670 mg) and benzylamine (0.5 ml) in toluene (60 ml) in the presence of a catalytic amount of p-toluenesulfonic acid monohydrate was refluxed for 2 hours to remove water as the toluene azeotrope, and then the mixture was evaporated in vacuo. To the residue in methanol (60 ml) was added sodium borohydride (0.5 g) under nitrogen at 5° C., and the mixture was stirred at room temperature for 12 hours. The resulting mixture was poured into ice-cold water and stirred for 30 minutes before adding ethyl acetate and brine. After separation, the organic layer was washed with brine, dried over anhydrous magnesium sulfate and evaporated in vacuo. The residue was chromatographed (hexane-ethyl acetate-methanol) over silica gel to afford N-benzyl-(1,4-dimethoxy-5,6,8,9-tetrahydrobenzcyclohepten-7-yl)amine (600 mg).

MASS (m/z): 312 (M+H)$^+$

Preparation 83

Under nitrogen, to fuming nitric acid (60 ml) was added 6,7,8,9-tetrahydrobenzocyclohepten-5-one (20 g) on ice-cooling, and the mixture was stirred at the same temperature for 1 hour. The resulting mixture was poured into ice water (200 ml). The precipitates were collected by filtration and dissolved into ethyl acetate. The organic layer was washed with brine, dried over magnesium sulfate and evaporated in vacuo to afford 3-nitro-6,7,8,9-tetrahydrobenzocyclohepten-5-one (14.87 g).

(+) APCI-MASS (m/z): 228 (M+Na)$^+$

Preparation 84

A mixture of 3-nitro-6,7,8,9-tetrahydrobenzocyclohepten-5-one (14.87 g), iron (14.87 g) and ammonium chloride (2.0 g) in ethanol (200 ml) and water (40 ml) was refluxed for 5 hours, and filtered. The filtrate was evaporated in vacuo to afford 3-amino-6,7,8,9-tetrahydrobenzocyclohepten-5-one (12.86 g).

NMR (CDCl$_3$, δ) 1.75–1.90 (4H, m), 2.60–2.90 (6H, m), 6.73–7.07 (3H, m)

Preparation 85

To a solution of 3-amino-6,7,8,9-tetrahydrobenzocyclohepten-5-one (12.53 g) in 10% sulfuric acid (130 ml) was added sodium nitrite (4.9 g) and sodium sulfite (694 mg) under ice-cooling. After being stirred for 20 minutes at this temperature, to the reaction mixture was added toluene (100 ml), stirred at the room temperature for 18 hours and extracted with ethyl acetate. The organic layer was washed with brine, dried over mag nesium sulfate and evaporated in vacuo to afford 3-hydroxy-6,7,8,9-tetrahydrobenzocyclohepten-5-one (7.08 g).

(+) APCI-MASS (m/z): 177 (M+H)$^+$

Preparation 86

A mixture of 3-hydroxy-6,7,8,9-tetrahydrobenzocyclohepten-5-one (7.02 g), potassium carbonate (8.25 g) and iodomethane (7.4 ml) in N,N-dimethylformamide (70 ml) was stirred at 50–55° C. for 7 hours. The resulting mixture was diluted with ethyl acetate. The organic layer was washed with brine, dried over magnesium sulfate and evaporated in vacuo to afford 3-methoxy-6,7,8,9-tetrahydrobenzocyclohepten-5-one (5.49 g).

(+) APCI-MASS (m/z): 191 (M+H)$^+$

Preparation 87

A solution of 3-methoxy-6,7,8,9-tetrahydrobenzocyclohepten-hepten-5-one (6.0 g) and benzylamine (3.4 ml) in toluene (60 ml) in the presence of a catalytic amount of p-toluenesulfonic acid monohydrate was refluxed for 2 hours to remove water at the toluene azeotrope, and then the mixture was evaporated in vacuo. To the residue in methanol (60 ml) was added sodium borohydride (1.2 g) under nitrogen at 5° C., and the mixture was stirred at room temperature for 12 hours. The resulting mixture was poured into ice-cold water and stirred for 30 minutes. After separation, the organic layer was washed with brine, dried over anhydrous magnesium sulfate and evaporated in vacuo. The residue was chromatographed (hexane-ethyl acetate-methanol) over silica gel to afford N-benzyl-(1-methoxy-6,7,8,9-tetrahydro-5H-benzocyclohepten-6-yl)amine (7.27 g).

(+) APCI-MASS (m/z): 282 (M+H)$^+$

Preparation 88

Methanesulfonyl chloride (1.4 ml) was added dropwise to a solution of acetic acid 3-amino-4-benzylphenyl ester (4.3 g) in pyridine (20 ml) under ice-cooling over 10 minutes, and the mixture was stirred at room temperature for a further 1 hour. Therein was added water (100 ml) and the resulting mixture was stirred at the same temperature for 1 hour. The precipitates were collected by filtration, dissolved into chloroform (100 ml), followed by its dryness over magnesium sulfate and its evaporation in vacuo. The residue was chromatographed (hexane-ethyl acetate) over silica gel to afford acetic acid 4-benzyloxy-3-methanesulfonylaminophenyl ester (1.6 g).

NMR (CDCl$_3$δ): 2.27 (3H, s), 2.95 (3H, s), 5.09 (2H, s), 6.80–7.03 (3H, m), 7.25–7.45 (6H, m)

(+) APCI-MASS (m/z): 336 (M+H)$^+$

Preparation 89

A solution of acetic acid 4-benzyloxy-3-methanesulfonylaminophenyl ester (1.6 g) and potassium hydride (2.67 g) in methanol (10 ml) was stirred for 18 hours at room temperature. The reaction mixture was acidified with 1N hydrochloric acid to pH 5–7 and extracted with ethyl acetate. The extract was washed with brine, dried over magnesium sulfate, and evaporated in vacuo. The residue was chromatographed (hexane-ethyl acetate) over silica gel to afford N-(2-benzyloxy-5-hydroxyphenyl)methanesulfonamide (750 mg).

NMR (CDCl$_3$, δ): 2.90 (3H, s), 5.04 (2H, s), 6.58 (1H, dd, J=2.9 and 8.8 Hz), 6.80–6.90 (2H, m), 7.09 (1H, d, J=2.9 Hz), 7.30–7.50 (6H, m)

(+) APCI-MASS (m/z): 294 (M+H)$^+$

Preparation 90

Under nitrogen, to a solution of N-(2-benzyloxy-5-hydroxyphenyl)methanesulfonamide (740 mg) and sodium hydride (92.4 mg) in N,N-dimethylformamide (30 ml) was added (2S)-(+)-1-tosyloxy-2,3-epoxypropane (616 mg) at 0° C. and the mixture was stirred at the same temperature for 0.5 hour. The mixture was allowed to warm to room temperature and stirred for 2.5 hours at this temperature. The resulting mixture was poured into 10% aqueous ammonium chloride solution and extracted with ethyl acetate. The extract was washed with brine, dried over magnesium sulfate and evaporated in vacuo. The residue was chromatographed (hexane-ethyl acetate) over silica gel to afford (2S)-1-(4-benzyloxy-3-methanesulfonylamino)phenoxy-2,3-epoxypropane (440 mg).

NMR (CDCl$_3$, δ): 2.75 (1H, dd, J=2.7 and 4.9 Hz), 2.84–2.95 (4H, m), 3.30–3.37 (1H, m), 3.90 (1H, dd, J=5.8 and 11.1 Hz), 4.07–4.25 (1H, m), 5.05 (2H, s), 6.63–7.48 (9H, m)

(+) APCI-MASS (m/z): 350 (M+H)$^+$

Preparation 91

To a solution of 2-[8-[(2S)-2-hydroxy-3-phenoxypropylamino]-6,7,8,9-tetrahydro-5H-benzocyclohepten-2-yloxy]acetic acid ethyl ester (3.29 g) and triethylamine (2.55 ml) in tetrahydrofuran (20 ml) was added di-tert-butyl dicarbonate (1.53 g) under ice-cooling, and the mixture was stirred at room temperature for 18 hours. The resulting mixture was poured into saturated aqueous sodium bicarbonate solution and extracted with ethyl acetate. The organic layer was washed with brine, dried over magnesium sulfate and evaporated in vacuo. The residue was chromatographed (hexane-ethyl acetate) over silica gel to afford 2-[8-[N -tert-butoxycarbonyl-N-[(2S)-2-hydroxy-3-phenoxypropyl]amino]-6,7,8,9-tetrahydro-5H-benzocyclohepten-2-yloxy]acetic acid ethyl ester (3.61 g).

NMR (CDCl$_3$, δ): 1.30 (3H, t, J=9.1 Hz), 1.49 (9H, s), 1.50–2.05 (4H, m), 1.60–1.80 (3H, m), 3.20–3.80 (4H, m), 3.90–4.20 (3H, m), 4.27 (2H, q, J=7.1 Hz), 4.57 (1H, s), 6.60–6.70 (2H, s), 6.90–7.05 (4H, m), 7.10–7.38 (2H, m)

Preparation 92

To a solution of 2-[8-[N-tert-butoxycarbonyl-N-[(2S)-2-hydroxy-3-phenoxypropyl]amino]-6,7,8,9-tetrahydro-5H-benzocyclohepten-2-yloxy]acetic acid ethyl ester (3.60 g) in ethanol (20 ml) was added 1N sodium hydroxide (7 ml) under ice-cooling, and the mixture was stirred at room temperature for 2 hours. The resulting mixture was acidified with hydrochloric acid to pH 2 and extracted with ethyl acetate. The organic layer was washed with brine, dried over magnesium sulfate and evaporated in vacuo. The residue was chromatographed (hexane-ethyl acetate) over silica gel to afford 2-[8-[N-tert-butoxycarbonyl-N-[(2S)-2-hydroxy-3-phenoxypropyl]amino]-6,7,8,9-tetrahydro-5H-benzocyclohepten-2-yloxy]acetic acid (3.2 g).

NMR (CDCl$_3$, δ): 1.49 (9H, s), 1.90–2.05 (4H, m), 2.60–2.80 (3H, m), 3.20–3.75 (4H, m), 3.80–4.30 (3H, m), 4.61 (2H, s), 6.60–6.75 (2H, m), 6.80–7.05 (4H, m), 7.20–7.40 (2H, m)

Preparation 93

Under nitrogen, to a solution of N-benzyl-(3-methoxy-6,7,8,9-tetrahydro-5H-benzocyclohepten-6-yl)amine (300 mg) and 1-[N-phenyl-N-benzyloxycarbonylamino]-2,3-epoxypropane (300 mg) in dichloromethane (5 ml) was added ytterbium(III) trifluoromethanesulfonate (66 mg) at room temperature, and the mixture was stirred at the same temperature for 24 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (hexane:ethyl acetate=10:1 to 4:1) to give N-[3-[N'-benzyl-N-(3-methoxy-6,7,8,9- tetrahydro-5H-benzocyclohepten-6-yl)amino]-2-hydroxypropyl[-N-benzyloxycarbonylphenylamine (307 mg).

(+) APCI-MASS (m/z): 565 (M+H)+

EXAMPLE 1

Under nitrogen, to a solution of N-benzyl-(3-methoxy-6,7,8,9-tetrahydro-5H-benzocyclohepten-6-yl)amine (487 mg) and (2S)-3-phenoxy-1,2,-epoxypropane (338 mg) in dichloromethane (10 ml) was added ytterbium(III) trifluoromethanesulfonate (107 mg) at room temperature, and the mixture was stirred at the same temperature for 3 hours. The resulting mixture was poured into saturated aqueous sodium bicarbonate solution, and extracted with ethyl acetate. The organic layer was washed with brine, dried over magnesium sulfate, and evaporated in vacuo. The residue was chromatographed (hexane-ethyl acetate) over silica gel to afford (2S)-1-[N-benzyl-N-(3-methoxy-6,7,8,9-tetrahydro-5H-benzocyclohepten-6-yl)amino]-3-phenoxy-2-propanol (750 mg).

NMR (CHCl$_3$, δ): 1.22–2.15 (4H, m), 2.45–3.10 (6H, m), 3.32–3.39 (1H, m), 3.70–4.10 (7H, m), 4.20–4.25 (1H, m), 6.58–7.00 (7H, m), 7.20–7.45 (6H, m)

MASS (m/z): 432 (M+H)+

The following compounds [Example 2 to 4] were obtained according to a similar manner to that of Example 1.

EXAMPLE 2

(2S)-1-[N-Benzyl-N-(1-methoxy-6,7,8,9-tetrahydro-5H-benzocyclohepten-6-yl) amino]-3-phenoxy-2-propanol NMR (CHCl$_3$, δ): 1.10–2.35 (5H, m), 2.50–3.15 (6H, m), 3.32–3.48 (1H, m), 3.64–3.98 (5H, m), 3.77 (3H, s), 6.69–7.09 (6H, m), 7.18–7.32 (7H, m)

MASS (m/z): 432 (M+H)+

EXAMPLE 3

2-[8-[N'-Benzyl-(2-hydroxy-3-phenoxypropyl)amino]-6,7,8,9-tetrahydro-5H-benzocyclohepten-2-yloxy]-N-phenylacetamide NMR (CDCl$_3$, δ): 1.22–2.33 (4H, m), 2.53–3.18 (7H, m), 3.67–4.05 (5H, m), 4.55–4.63 (2H, m), 6.65–6.78 (1H, m), 6.78–7.05 (5H, m), 7.05–7.47 (10H, m), 7.60 (2H, d, J=8.5 Hz)

MASS (m/z): 551 (M+H)+

EXAMPLE 4

2-[8-[N'-Benzyl-(2-hydroxy-3-phenoxypropyl)amino]-6,7,8,9-tetrahydro-5H-benzocyclohepten-2-yloxy]-N-butylacetamide NMR (CDCl$_3$, δ): 0.92 (3H, t, J=7.4 Hz), 1.15–2.30 (8H, m), 2.50–2.95 (6H, m), 2.98–3.15 (1H, m), 3.35 (2H, q, J=6.7 Hz), 3.63–4.01 (5H, m), 4.41–4.50 (2H, m), 6.47–7.03 (7H, m), 7.15–7.45 (7H, m)

MASS (m/z): 531 (M+H)+

EXAMPLE 5

N-Benzyl-(2-methoxy-6,7,8,9-tetrahydro-5H-benzocyclohepten-6-yl)amine hydrochloride was converted to the corresponding free base in a usual manner. A mixture of (2S)-3-phenoxy-1,2-epoxypropane (75 mg), N-benzyl-(2-methoxy-6,7,8,9-tetrahydro-5H-benzocyclohepten-6-yl)amine (140 mg), and ytterbium(III) trifluoromethanesulfonate (93 mg) in toluene (2.6 ml) was stirred at room temperature for 3 days and partitioned between ethyl acetate and aqueous sodium bicarbonate. The organic layer was separated, washed with brine, dried over sodium sulfate, and evaporated in vacuo. The residue was chromatographed (dichloromethane-methanol) over silica gel to afford (2S)-1-[N-benzyl-N-(2-methoxy-6,7,8,9-tetrahydro-5H-benzocyclohepten-6-yl)amino]-3-phenoxy-2-propanol (200 mg).

IR (KBr): 3427, 1248 cm$^{-1}$

NMR (CDCl$_3$, δ): 1.25–2.25 (4H, m), 2.5–3.02 (7H, m), 3.65–4.0 (8H, m), 6.63 (2H, m), 6.83–6.98 (3H, m), 7.03–7.08 (1H, m), 7.18–7.31 (7H, m)

MASS (m/z): 432 (M+H)+

EXAMPLE 6

A mixture of (2S)-1-[N-benzyl-(3-methoxy-6,7,8,9-tetrahydro-5H-benzocyclohepten-6-yl)amino]-3-phenoxy-2-propanol (750 mg) and 10% palladium on activated carbon (50% wet, 200 mg) in methanol (10 ml) was stirred at room temperature in the presence of hydrogen at an atmospheric pressure for 3 hours, and filtered. The filtrate was evaporated in vacuo and treated with 4N hydrogenchloride in ethyl acetate to afford (2S)-1-[(3-methoxy-6,7,8,9-tetrahydro-5H-benzocyclohepten-6-yl)amino]-3-phenoxy-2-propanol hydrochloride (446 mg).

NMR (DMSO-d$_6$, δ): 1.09–1.30 (1H, m), 1.80–2.10 (2H, m), 2.25–2.34 (1H, m), 2.55–2.70 (2H, m), 3.00–3.70 (5H, m), 3.73 (3H, s), 4.01 (2H, d, J=4.0 Hz), 4.20–4.30 (1H, m), 5.94 (1H, br s), 6.71 (1H, dd, J=2.6 and 8.2 Hz), 6.83 (1H, dd, J=2.7 and 6.2 Hz), 6.87–7.08 (4H, m), 7.23–7.36 (2H, m), 8.90 (1H, br s), 8.29 (1H, br s)

MASS (m/z): 342 (M+H)+

The following compounds [Example 7 and 8] were obtained according to a similar manner to that of Example 6.

EXAMPLE 7

(2S)-1-[(2-Methoxy-6,7,8,9-tetrahydro-5H-benzocyclohepten-6-yl)amino]-3-phenoxy-2-propanol hydrochloride IR (KBr): 3423, 2800–2350, 1246 cm$^{-1}$ NMR (DMSO-d$_6$, δ): 1.35 (1H, m), 1.75–2.05 (2H, m), 2.25–2.35 (1H, m), 2.70 (2H, m), 2.95–3.35 (5H, m), 3.71 (3H, s), 4.01 (2H, m), 4.24 (1H, m), 5.91 (1H, d, J=4.8 Hz), 6.66–6.73 (2H, m), 6.92–6.70 (3H, m), 7.12 (1H, dd, J=8.0 and 2.5 Hz), 7.31 (2H, t, J=7.8 Hz), 8.78 (1H, br), 9.07 (1H, br)

MASS (m/z): 342 (M+H)+

EXAMPLE 8

(2S)-1-[(1-Methoxy-6,7,8,9-tetrahydro-5H-benzocyclohepten-6-yl)amino]-3-phenoxy-2-propanol hydrochloride NMR (DMSO-d$_6$, δ): 1.04–1.32 (1H, m), 1.75–2.11 (2H, m), 2.23–2.40 (1H, m), 2.96–3.49 (7H, m), 3.75 (3H, s), 3.96–4.03 (2H, m), 4.26 (1H, br s), 5.92 (1H, br s), 6.81–7.01 (5H, m), 7.11 (1H, t, J=7.7 Hz), 7.31 (2H, t, J=7.7 Hz), 8.88 (1H, br s), 9.25 (1H, br s)

MASS (m/z): 342 (M+H)+

EXAMPLE 9

A mixture of 2-[8-[N'-benzyl-(2-hydroxy-3-phenoxypropyl) amino]-6,7,8,9-tetrahydro-5H- benzocyclohepten-2-yloxy]-N-phenylacetamide (360 mg) and 10% palladium on activated carbon (50% wet, 70 mg) in ethanol (5 ml) was stirred at room temperature in the presence of hydrogen at an atmospheric pressure for 4 hours and filtered. The filtrate was evaporated in vacuo. The residue was chromatographed (chloroform-methanol) over silica gel to afford 2-[8-(2-hydroxy-3-phenoxypropylamino)-6,7,8,9-tetrahydro-5H-benzocyclohepten-2-yloxy]-N-phenylacetamide (306 mg)

The above obtained compound (306 mg) was treated with methanesulfonic acid (43 μl) to afford 2-[8-(2-hydroxy-3-phenoxypropylamino)-6,7,8,9-tetrahydro-5H-benzocyclohepten-2-yloxy]-N-phenylacetamide methanesulfonate (303 mg)

NMR (DMSO-$d_6$, δ): 1.18–1.43 (1H, m), 1.74–2.13 (2H, m), 2.18–2.37 (1H, m), 2.39 (3H, s), 2.60–2.83 (2H, m), 2.95–3.38 (5H, m), 3.95–4.40 (3H, m), 4.68 (2H, s), 6.78 (1H, d, J=8.0 Hz), 6.86–7.14 (6H, m), 7.32 (4H, t, J=7.6 Hz), 7.65 (2H, d, J=8.0 Hz), 8.59 (2H, br s), 10.11 (1H, s)

MASS (m/z): 461 (M+H)$^+$

EXAMPLE 10

A mixture of 2-[8-(N'-benzyl-(2-hydroxy-3-phenoxypropyl)amino]-6,7,8,9-tetrahydro-5H-benzocyclohepten-2-yloxy]-N-butylacetamide (206 mg) and 10% palladium on activated carbon (50% wet, 40 mg) in ethanol (5 ml) was stirred at room temperature in the presence of hydrogen at an atmospheric pressure for 4 hours, and filtered. The filtrate was evaporated in vacuo. The residue was chromatographed (chloroform-methanol) over silica gel to afford 2-[8-(2-hydroxy-3-phenoxypropylamino)-6,7,8,9-tetrahydro-5H-benzocyclohepten-2-yloxy]-N-butylacetamide (171 mg).

The above obtained compound (70 mg) was treated with oxalic acid (14 mg) to afford 2-[8-(2-hydroxy-3-phenoxypropylamino)-6,7,8,9-tetrahydro-5H-benzocyclohepten-2-yloxy]-N-butylacetamide oxalate (28 mg)

NMR (DMSO-$d_6$, δ): 0.85 (3H, t, J=6.9 Hz), 1.10–1.50 (5H, m), 1.70–2.12 (2H, m), 2.15–2.37 (1H, m), 2.60–2.78 (2H, m), 2.90–3.37 (7H, m), 3.99 (2H, br s), 4.20 (1H, br s), 4.63 (2H, s), 6.72 (1H, d, J=8.0 Hz), 6.77–7.10 (5H, m), 7.31 (2H, d, J=7.4 Hz)

MASS (m/z): 441 (M+H)$^+$

EXAMPLE 11

A mixture of 4-oxiranylmethoxy-1,3-dihydro-2-benzimidazolone (82.5 mg) and N-benzyl-(6,7,8,9-tetrahydro-2-hydroxy-5H-benzocyclohepten-6-yl)amine (107 mg) in ethanol (1.5 ml) was stirred under reflux for 13 hours, cooled to room temperature and evaporated in vacuo. The residue was chromatographed (dichloromethane-methanol)by silica gel (4.2 g) to afford 1-[N-benzyl-N-(6,7,8,9-tetrahydro-2-hydroxy-5H-benzocyclohepten-6-yl)amino]-3-(1,3-dihydro-2-benzoimidazolon-4-yloxy)-2-propanol (123 mg) as a colorless powder.

mp: 111–133° C. (dec.)

IR (KBr): 3408 (br), 3257 (br), 1695, 1248 cm$^{-1}$

NMR (DMSO-$d_6$, δ): 1.03–1.97 (4H, m), 2.22–2.84 (6H, m), 3.63–4.17 (6H, m, 4.60 and 4.67 (1H, each d, J=4.1 Hz), 6.43 (2H, m), 6.53–6.63 (2H, m), 6.79–6.95 (2H, m), 7.11–7.35 (5H, m), 8.99 (1H, s), 10.55 (2H, br s)

(+) APCI-MASS (m/z): 474 (M+H)$^+$

EXAMPLE 12

A solution of (2S)-1,2-epoxy-3-phenoxypropane (53 mg) (IL FARMACO, 50 (10), 643 (1995)) and N-benzyl -(3-chloro-6,7,8,9-tetrahydro-2-hydroxy-5H-benzocyclohepten-6-yl)amine (89 mg) in ethanol (1 ml) was refluxed for 19 hours, cooled to room temperature and evaporated in vacuo. The residue was chromatographed (dichloromethane-methanol) by silica gel (2.9 g), and the eluate was treated with 4N hydrogen chloride in ethyl acetate to afford (2S)-1-[N-benzyl-N-(3-chloro-6,7,8,9-tetrahydro-2-hydroxy-5H-benzocyclohepten-6-yl) amino]-3-phenoxy-2-propanol hydrochloride (149 mg) as a colorless powder.

mp: 94–99° C. (dec.)

IR (KBr): 3421 (br), 2750–2450 (m), 1244 cm$^{-1}$

EXAMPLE 13

Under nitrogen, to a solution of N-benzyl-(3-isopropoxy-6,7,8,9-tetrahydro-5H-benzocyclohepten-6-yl)amine (258 mg) and (2S)-3-phenoxy-1,2-epoxypropane (138 mg) in dichloromethane (5 ml) was added ytterbium(III) trifluoromethanesulfonate (52 mg) at room temperature, and the mixture was stirred at the same temperature for 60 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (hexane:ethyl acetate=10:1 to 5:1) to give (2S)-1-[N-benzyl-N-(3-isopropoxy-6,7,8,9-tetrahydro-5H-benzocyclohepten-6-yl)-amino]-3-phenoxy-2-propanol (303 mg)

(+) APCI-MASS (m/z): 460 (M+H)$^+$

The following compounds [Examples 14 to 27] were obtained according to a similar manner to that of Example 13.

EXAMPLE 14

(2S)-1-[N-Benzyl-N-(3-hexyloxy-6,7,8,9-tetrahydro-5H-benzocyclohepten-6-yl) amino]-3-phenoxy-2-propanol (+) APCI-MASS (m/z): 502 (M+H)$^+$

EXAMPLE 15

(2S)-1-[N-Benzyl-N-(3-benzyloxy-6,7,8,9-tetrahydro-5H-benzocyclohepten-6-yl) amino]-3-phenoxy-2-propanol (+) ESI-MASS (m/z): 508 (M+H)$^+$

EXAMPLE 16

(2S)-1-[N-Benzyl-N-[3-(3-cyanopyridin-2-yloxy)-6,7,8,9-tetrahydro-5H-benzocyclohepten-6-yl]amino]-3-phenoxy-2-propanol (+) APCI-MASS (m/z): 520 (M+H)$^+$

EXAMPLE 17

(2S)-1-[N-Benzyl-N-[3-(2-methoxyethoxy)-6,7,8,9-tetrahydro-5H-benzocyclohepten-6-yl)]amino]-3-phenoxy-2-propanol (+) APCI-MASS (m/z): 476 (M+H)$^+$

EXAMPLE 18

(2S)-1-[N-Benzyl-N-(3-nitro-6,7,8,9-tetrahydro-5H-benzocyclohepten-6-yl) amino]-3-phenoxy-2-propanol (+) APCI-MASS (m/z): 447 (M+H)$^+$

EXAMPLE 19

(2S)-1-(N-Benzyl-N-(6,7,8,9-tetrahydro-5H-benzocyclohepten-6-yl)amino]-3-phenoxy-2-propanol (+) APCI-MASS (m/z): 402 (M+H)$^+$

EXAMPLE 20

(2S)-1-[N-Benzyl-N-(3-phenyl-6,7,8,9-tetrahydro-5H-benzocyclohepten-6-yl)amino]-3-phenoxy-2-propanol (+) ESI-MASS (m/z): 478 (M+H)+

EXAMPLE 21

(2S)-1-[N-Benzyl-N-(2-chloro-3-methoxy-6,7,8,9-tetrahydro-5H-benzocyclohepten-6-yl)amino]-3-phenoxy-2-propanol (+) ESI-MASS (m/z): 466, 468 (M+H)+

EXAMPLE 22

(2S)-1-[N-Benzyl-N-(3-methoxy-6,7,8,9-tetrahydro-5H-benzocyclohepten-6-yl)amino]-3-phenylthio-2-propanol (+) APCI-MASS (m/z): 448 (M+H)+

EXAMPLE 23

(2S)-1-[N-Benzyl-N-(3-methoxy-6,7,8,9-tetrahydro-5H-benzocyclohepten-6-yl)amino]-3-(4-fluorophenoxy)-2-propanol NMR (CDCl$_3$, δ): 0.85–1.25 (1H, m), 1.65–2.1 (2H, m), 2.2–2.4 (1H, m), 2.45–2.95 (7H, m), 3.65–3.85 (7H, m), 3.85–4.1 (1H, m), 6.55–6.6 (1H, m), 6.65–6.75 (1H, m), 6.8–7.4 (10H, m)

(+) APCI-MASS (m/z): 450 (M+H)+

EXAMPLE 24

(2S)-1-[N-Benzyl-N-(6,7,8,9-tetrahydro-4-methoxy-5H-benzocyclohepten-6-yl)amino]-3-phenoxy-2-propanol hydrochloride NMR (DMSO-d$_6$, δ): 1.10–1.38 (1H, m), 1.97–2.20 (2H, m), 2.38–2.52 (1H, m), 2.60–3.00 (4H, m), 3.18–3.58 (3H, m), 3.70–4.02 (3H, m), 3.79 (3H, s), 4.45–4.64 (2H, m), 6.01 (1H, br), 6.70–6.99 (5H, m), 7.13 (1H, dd, J=8.0, 8.0 Hz), 7.30 (2H, dd, J=7.9, 7.9 Hz), 7.40–7.56 (3H, m), 7.65–7.80 (2H, m), 9.42–10.09 (1H, br)

(+) ESI-MASS (m/z): 432 (M+H)+

EXAMPLE 25

(2S)-1-[N-Benzyl-N-(3-methoxycarbonyl-6,7,8,9-tetrahydro-5H-benzocyclohepten-6-yl)amino]-3-phenoxy-2-propanol hydrochloride NMR (DMSO-d$_6$, δ): 1.10–1.33 (1H, m), 1.99–2.21 (2H, m), 2.40–2.55 (1H, m), 2.75–2.91 (2H, m), 3.04–3.17 (1H, m), 3.26–3.38 (3H, m), 3.45–3.59 (2H, m), 3.70–4.01 (2H, m), 3.84 (3H, s), 4.39–4.69 (2H, m), 5.92–6.05 (1H, br), 6.81–7.00 (3H, m), 7.23–7.34 (3H, m), 7.38–7.48 (3H, m), 7.68–7.97 (4H, m), 9.67–9.95 (1H, br)

(+) ESI-MASS (m/z): 460 (M+H)+

EXAMPLE 26

(2S)-1-[N-Benzyl-N-(3-carbamoyl-6,7,8,9-tetrahydro-5H-benzocyclohepten-6-yl)amino]-3-phenoxy-2-propanol hydrochloride NMR (DMSO-d$_6$, δ): 1.18–1.34 (1H, m), 2.00–2.20 (2H, m), 2.33–2.58 (1H, m), 2.78–2.90 (2H, m), 3.02–3.50 (5H, m), 3.72–4.02 (3H, m), 4.28–4.62 (2H, m), 5.98 (1H, br), 6.80–6.98 (3H, m), 7.17–7.44 (7H, m), 7.63–7.91 (5H, m), 9.36–9.92 (1H, br)

(+) APCI-MASS (m/z): 445 (M+H)+

EXAMPLE 27

1-[N-Benzyl-N-(3-methoxy-6,7,8,9-tetrahdyro-5H-benzocyclohepten-6-yl)amino]-4-phenyl-2-butanol (+) APCI-MASS (m/z): 430 (M+H)+

EXAMPLE 28

Under nitrogen, to a solution of N-(3-fluoromethoxy-6,7,8,9-tetrahydro-5H-benzocyclohepten-6-yl)-N-tert-butoxycarbonyl-[(2S)-3-phenoxy-2-(triethylsilyloxy)propyl]-amine (300 mg) in tetrahydrofuran (5 ml) was added tetra-n-butylammonium fluoride (1M in tetrahydrofuran, 0.58 ml) at 5° C., and the mixture was stirred at the same temperature for 15 minutes. The resulting mixture was poured into water and extracted with ethyl acetate. The organic layer was washed with brine, dried over anhydrous magnesium sulfate and evaporated in vacuo. The residue was purified by column chromatography on silica gel (hexane:ethyl acetate=3:1) to give N-(3-fluoromethoxy-6,7,8,9-tetrahydro-5H-benzocyclohepten-6-yl)-N-tert-butoxycarbonyl-[(2S)-2-hydroxy-3-phenoxypropyl]amine (227 mg).

NMR (CDCl$_3$, δ): 1.1–1.6 (1H, m), 1.49 (9H, s), 1.9–2.1 (3H, m), 2.65–2.75 (3H, m), 3.15–3.7 (4H, m), 3.8–4.2 (3H, m), 5.67 (2H, d, J=54.8 Hz), 6.75–7.1 (5H, m), 7.25–7.3 (2H, m)

EXAMPLE 29

Under nitrogen, to a suspension of sodium hydride (60% in oil, 12 mg) in N,N-dimethylformamide (3 ml) was added N-(3-hydroxy-6,7,8,9-tetrahydro-5H-benzocyclohepten-6-yl)-N-tert-butoxycarbonyl-[(2S)-3-phenoxy-2-(triethylsilyloxy)-propyl]amine (150 mg) at 5° C. After being stirred at the same temperature for 1.5 hours, to this one was added dimethylsulfonyl chloride (31 μl), and the mixture was stirred at 60° C. for 15 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (hexane:ethyl acetate=3:1) to give (1): N-(3-dimethylsulfonyloxy-6,7,8,9-tetrahydro-5H-benzocyclohepten-6-yl)-N-tert-butoxycarbonyl-[(2S)-3-phenoxy-2-(triethylsilyloxy)propyl]amine (59 mg) and (2): N-(3-dimethylsulfonyloxy-6,7,8,9-tetrahydro-5H-benzocyclohepten-6-yl)-N-tert-butoxycarbonyl-[(2S)-2-hydroxy-3-phenoxypropyl]-amine (66 mg).

(1): NMR (CDCl$_3$, δ): 0.55–0.7 (6H, m), 0.9–1.05 (9H, m), 0.2–1.5 (1H, m), 1.48 (9H, m), 1.9–2.15 (3H, m), 2.7–3.0 (3H, m), 2.95 (6H, m), 3.1–3.7 (4H, m), 3.85–4.05 (2H, m), 4.3–4.4 (1H, m), 6.85–7.1 (6H, m), 7.25–7.3 (2H, m)

(+) APCI-MASS (m/z): 549 (M-Boc+2H)+

(2): NMR (CDCl$_6$, δ): 0.55–0.7 (6H, m), 0.9–1.05 (9H, m), 1.2–1.5 (1H, m), 1.48 (9H, m), 1.9–2.15 (3H, m), 2.7–3.0 (3H, m), 2.95 (6H, m), 3.1–3.7 (4H, m), 3.85–4.05 (2H, m), 4.3–4.4 (1H, m), 6.85–7.1 (6H, m), 7.25–7.3 (2H, m)

(+) APCI-MASS (m/z): 435 (M-Boc+2H)+

EXAMPLE 30

Under nitrogen, to a solution of 2-(8-benzylamino-6,7,8,9-tetrahydro-5H-benzocyclohepten-2-yloxy)acetamide (260 mg) and (2S)-3-phenoxy-1,2-epoxypropane (130 mg) in dichloromethane (3 ml) was added ytterbium(III) trifluoromethanesulfonate (50 mg) at room temperature, and the mixture was stirred at the same temperature for 12 hours. The resulting mixture was poured into saturated aqueous sodium hydrogencarbonate and extracted with dichloromethane. The organic layer was washed with brine, dried over anhydrous magnesium sulfate and evaporated in vacuo. The residue was purified by column chromatography on silica gel (chloroform:ethyl acetate=20:1 to 10:1), followed by treatment with methanesulfonic acid in chloroform to give 2-[8-[N-benzyl-N-[(2S)-2-hydroxy-3-phenoxypropyl]amino]-6,7,8,9-tetrahydro-5H-benzocyclohepten-2-yloxy]acetamide methanesulfonate (290 mg).

(+) APCI-MASS (m/z): 475 (M-MsOH+H)+

EXAMPLE 31

A solution of 2-[8-[N-benzyl-N-[(2S)-2-hydroxy-3-phenoxypropyl]amino]-6,7,8,9-tetrahydro-5H-benzocyclohepten-2-yloxy]acetic acid ethyl ester (200 mg) and N,N-dimethylethylenediamine (130 μl) in methanol (2 ml) was stirred at room temperature for 24 hours. After evaporation in vacuo, the residue was purified by preparative thin layer chromatography (silica gel, chloroform:methanol=10:1) to give 2-[8-[N'-benzyl-N'-[(2S)-2-hydroxy-3-phenoxypropyl]-amino]6,7,8,9-tetrahydro-5H-benzocyclohepten-2-yloxy]-N-(2-dimethylaminoethyl)acetamide (215 mg).

(+) APCI-MASS (m/z): 546 (M+H)+

EXAMPLE 32

Under nitrogen, a solution of 2-[8-[N-tert-butoxycarbonyl-N-[(2S)-2-hydroxy-3-phenoxypropyl]amino]-6,7,8,9-tetrahydro-5H-benzocyclohepten-2yloxy] acetic acid (100 mg) in dichloromethane (3 ml) were added N-methylbutylamine (29 μl) and 1-(3-dimethylaminopropyl)-3-ethylcarbodiimide hydrochloride (47 mg) in the presence of catalytic amounts of 4-dimethylaminopyridine at 5° C., and the mixture was stirred at room temperature for 12 hours. The resulting mixture was poured into 1N hydrochloric acid and extracted with ethyl acetate. The organic layer was successively washed with saturated aqueous sodium hydrogencarbonate and brine, dried over magnesium sulfate and evaporated in vacuo. The residue was purified by column chromatography on silica gel (hexane:ethyl acetate=1:1) to give N-[3-[(butylmethylcarbamoyl)methoxy]-6,7,8,9-tetrahydro-5H-benzocyclohepten-6-yl]-N-tert-butoxycarbonyl-[(2S)-2-hydroxy-3-phenoxypropyl]amine (96 mg).

NMR (CHCl$_3$, δ): 0.92 (3H, q, J=7.6 Hz), 1.18–1.70 (5H, m) , 1.49 (9H, s) , 1.93–2.15 (3H, m), 2.59–2.82 (3H, m), 2.94–3.04 (3H, m), 3.20–3.66 (6H, m), 3.83–4.25 (3H, m), 4.62–4.67 (2H, m,, 6.65–6.77 (2H, m), 6.87–7.02 (4H, m), 7.25–7.34 (2H, m)

(+) APCI-MASS (m/z): 455 (M-Boc+2H)+

The following compounds[Examples 33 to 38] were obtained according to a similar manner to that of Example 32.

EXAMPLE 33

N-[(2S)-2-Hydroxy-3-phenoxypropyl]-N-tert-butoxycarbonyl-[3-(sec-butylcarbamoylmethoxy)-6,7,8,9-tetrahydro-5H-benzocyclohepten-6-yl]amine (+) APCI-MASS (m/z): 441 (M-Boc+2H)+

EXAMPLE 34

N-(3-Cyclohexylcarbamoylmethoxy-6,7,8,9-tetrahydro-5H-benzocyclohepten-6-yl)-N-tert-butoxycarbonyl-[(3S)-2-hydroxy-3-phenoxypropyl)amine (+) APCI-MASS (m/z): 467 (M-Boc+2H)+

EXAMPLE 35

N-[3-(Benzylcarbamoylmethoxy)-6,7,8,9-tetrahydro-5H-benzocyclohepten-6-yl]-N-tert-butoxycarbonyl-[(2S)-2-hydroxy-3-phenoxypropyl]amine (+) APCI-MASS (m/z): 475 (M-Boc+2H)+

EXAMPLE 36

N-[(2S)-2-Hydroxy-3-phenoxypropyl]-N-tert-butoxycarbonyl-[3-[(2-methylthioethylcarbamoyl)methoxy]-6,7,8,9-tetrahydro-5H-benzocyclohepten-6-yl]amine (+) APCI-MASS (m/z): 459 (M-Boc+2H) +

EXAMPLE 37

N-[(2S)-2-Hydroxy-3-phenoxypropyl)-N-tert-butoxycarbonyl-[3-(2-piperidinocarbonylethoxy)-6,7,8,9-tetrahydro-5H-benzocyclohepten-6-yl]amine (+) APCI-MASS (m/z): 453 (M-Boc+2H)+

EXAMPLE 38

N-[(2S)-2-Hydroxy-3-phenoxypropyl]-N-tert-butoxycarbonyl-[3-[(1H-indol-5-yl-carbamoyl)methoxy]-6,7,8,9-tetrahydro-5H-benzocyclohepten-6-yl]amine NMR (CDCl$_3$, δ): 1.22–1.70 (1H, m), 1.50 (9H, s), 1.96–2.18 (3H, m), 2.66–2.88 (3H, m), 3.26–3.70 (4H, m), 3.85–4.26 (3H, m), 4.59 (2H, s), 6.51–6.56 (1H, m), 6.68–6.87 (2H, m), 6.88–7.09 (4H, m), 7.23–7.39 (6H, m), 7.92 (1H, m), 8.16–8.37 (2H, m)

(+) APCI-MASS (m/z): 500 (M-Boc+2H)+

EXAMPLE 39

A suspension of powdered iron (160 mg) and ammonium chloride (15 mg) in a mixture of ethanol (6 ml) and water (2 ml) was refluxed, and to this one was dropwise added (2S)-1-[N-benzyl-N-(3-nitro-6,7,8,9-tetrahydro-5H-benzocyclohepten-6-yl)amino]-3-phenoxy-2-propanol (158 mg) in ethanol (3 ml). After being further refluxed for 1 hour, insoluble materials were filtered off. The filtrate was evaporated in vacuo. The residue was dissolved into a mixture of saturated aqueous sodium hydrogencarbonate and ethyl acetate. After separation, the organic layer was washed with brine, dried over anhydrous magnesium sulfate and evaporated in vacuo. The residue was purified by column chromatography on silica gel (hexane:ethyl acetate=2:1 to 1:1) to give (2S)-1-[N-(3-amino-6,7,8,9-tetrahydro-5H-benzocyclohepten-6-yl)-N-benzylamino]-3-phenoxy-2-propanol (122 mg).

(+) ESI-MASS (m/z): 417 (M+H) +

EXAMPLE 40

Under nitrogen, a solution of (2S)-1-[N-(3-amino-6,7,8,9-tetrahydro-5H-benzocyclohepten-6-yl)-N-benzylamino]-3-phenoxy-2-propanol (200 mg), methyl iodide (0.15 ml) and N,N-diisopropylethylamine (0.25 ml) in dichloromethane (5 ml) was stirred at room temperature for 12 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (hexane:ethyl acetate=4:1) to give a less polar diastereomer: (2S)-1-[N-benzyl-N-(3-dimethylamino-6,7,8,9-tetrahydro-5H-benzocyclohepten-6-yl)amino]-3-phenoxy-2-propanol (28 mg) and a more polar diastereomer: (2S)-1-[N-benzyl-N-(3-dimethylamino-6,7,8,9-tetrahydro-5H-benzocyclohepten-6-yl)amino]-3-phenoxy-2-propanol (25 mg).

A Less Polar Diastereomer (+) APCI-MASS (m/z): 445 (M+H)$^+$

A More Polar Diastereomer (+) APCI-MASS (m/z): 445 (M+H)$^+$

EXAMPLE 41

Under nitrogen, a solution of (2S)-1-[N-(3-amino-6,7,8,9-tetrahydro-5H-benzocyclohepten-6-yl)-N-benzylamino]-3-phenoxy-2-propanol (113 mg), acetic anhydride (28 µl) and pyridine (24 µl) in dichloromethane (5 ml) was stirred at 5° C. for 1 hour. The resulting mixture was poured into water and extracted with ethyl acetate. The organic layer was washed with brine, dried over anhydrous magnesium sulfate and evaporated in vacuo. The residue was purified by column chromatography on silica gel (hexane:ethyl acetate=1:1 to 1:2) to give N-benzyl-N-[(2S)-2-hydroxy-3-phenoxypropyl]-3-acetylamino-6,7,8,9-tetrahydro-5H-benzocyclohepten-6-yl) amine (92 mg).

(+) APCI-MASS (m/z): 459 (M+H)$^+$

EXAMPLE 42

Under nitrogen, a solution of (2S)-1-[N-(3-amino-6,7,8,9-tetrahydro-5H-benzocyclohepten-6-yl)-N-benzylamino]-3-phenoxy-2-propanol (150 mg), benzoyl chloride (44 µl), pyridine (35 µl ), and catalytic amounts of 4-dimethylaminopyridine in dichloromethane (5 ml) was stirred at room temperature for 5 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (hexane:ethyl acetate=2:1) to give N-benzyl-N-[(2S)-2-hydroxy-3-phenoxypropyl]-3-benzoylamino-6,7,8,9-tetrahydro-5H-benzocyclohepten-2-ylamine (163 mg).

(+) APCI-MASS (m/z): 521 (M+H)$^+$

EXAMPLE 43

Under nitrogen, a solution of (2S)-1-[N-(3-amino-6,7,8,9-tetrahydro-5H-benzocyclohepten-6-yl)-N-benzylamino]-3-phenoxy-2-propanol (150 mg), methanesulfonyl chloride (29 µl), pyridine (35 µl), and catalytic amounts of 4-dimethylaminopyridine in dichloromethane (5 ml) was stirred at room temperature for 4 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (hexane:ethyl acetate=2:1) to give N-benzyl-N-[(2S)-2-hydroxy-3-phenoxypropylamino]-3-methylsulfonylamino-6,7,8,9-tetrahydro-5H-benzocyclohepten-2-ylamine (178 mg).

(+) APCI-MASS (m/z): 495 (M+H)$^+$

The following compound was obtained according to a similar manner to that of Example 43.

EXAMPLE 44

N-Benzyl-N-[(2S)-2-hydroxy-3-phenoxypropylamino]-6,7,8,9-tetrahydro-5H-benzocyclohepten-2-ylamine (+) ESI-MASS (m/z): 557 (M+H)$^+$

EXAMPLE 45

Under nitrogen, a solution of (2S)-1-(N-(3-amino-6,7,8,9-tetrahydro-5H-benzocyclohepten-6-yl)-N-benzylamino]-3-phenoxy-2-propanol (150 mg), methyl chloroformate (29 µl), pyridine (25 µl) and catalytic amounts of 4-dimethylaminopyridine in dichloromethane (3 ml) was stirred at room temperature for 1.5 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (hexane:ethyl acetate=3:1) to give (2S)-1-[N-(3-methoxycarbonylamino-6,7,8,9-tetrahydro-5H-benzocyclohepten-6-yl)-N-benzylamino]-3-phenoxy-2-propanol (158 mg).

(+) APCI-MASS (m/z): 475 (M+H)$^+$

The following compound was obtained according to a similar manner to that of Example 46.

EXAMPLE 46

(2S)-1-[N-(3-phenoxycarbonylamino-6,7,8,9-tetrahydro-5H-benzocyclohepten-6-yl)-N-benzylamino]-3-phenoxy-2-propanol (+) APCI-MASS (m/z): 537 (M+H)$^+$

EXAMPLE 47

Under nitrogen, a solution of (2S)-1-[N-(3-amino-6,7,8,9-tetrahydro-5H-benzocyclohepten-6-yl)-N-benzylamino]-3-phenoxy-2-propanol (150 mg), dimethylaminosulfonyl chloride (43 µl) and pyridine (31 µl)in toluent (5 ml) was stirred at 80° C. for 24 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (hexane:ethyl acetate=2:1) to give (2S)-1-[N-(3-dimethylaminosulfonylamino-6,7,8,9-tetrahydro-5H-benzocyclohepten-6-yl)-N-benzylamino]-3-phenoxy-2-propanol (156 mg).

(+) APCI-MASS (m/z): 524 (M+H)$^+$

The following compound was obtained according to a similar manner to that of Example 47.

EXAMPLE 48

(2S)-1-[N-(3-Sulfamoylamino-6,7,8,9-tetrahydro-5H-benzocyclohepten-6-yl)-N-benzylamino]-3-phenoxy-2-propanol (+) APCI-MASS (m/z): 496 (M+H)$^+$

EXAMPLE 49

To a solution of (2S)-1-[N-benzyl-N-(3-methoxy-6,7,8,9-tetrahydro-5H-benzocyclohepten-6-yl)amino]-3-phenylthio-2-propanol (221 mg) in methanol (10 ml) was added OXONE (610 mg) in water (3 ml) at room temperature, and the mixture was stirred at the same temperature for 5 hours. The resulting mixture was filtered off to remove precipitates and the filtrate was evaporated in vacuo. The residue was dissolved into a mixture of saturated aqueous sodium hydrogencarbonate and ethyl acetate. After separation, the organic layer was washed with brine, dried over anhydrous magnesium sulfate and evaporated in vacuo.

The residue was purified by column chromatography on silica gel (hexane:ethyl acetate=2:1) to give (2S)-1-[N-benzyl-N-(3-methoxy-6,7,8,9-tetrahydro-5H-benzocyclohepten-6-yl)amino]-3-phenylsulfonyl-2-propanol (170 mg).

(+) APCI-MASS (m/z): 480 (M+H)$^+$

EXAMPLE 50

A mixture of N-benzyl-N-(3-methoxy-6,7,8,9-tetrahydro-5H-benzocyclohepten-6-yl)amine (200 mg) and 10% palladium on activated carbon (50% wet, 50 mg) in methanol (5 ml) was stirred at room temperature in the presence of hydrogen at an atmospheric pressure for 3 hours. After filtration, the filtrate was evaporated in vacuo. A mixture of the residue and [5-[(2S)-oxiranyl)methoxypyridin-2-yl] carbamic acid benzyl ester (174 mg) in methanol (10 ml) was refluxed for 20 hours. After removal of the solvent in vacuo, the residue was purified by column chromatography on silica gel (chloroform:methanol=50:1 to 20:1) to give N-[5-[(2S)-2-hydroxy-3-(3-methoxy-6,7,8,9-tetrahydro-5H-benzocyclohepten-6-ylamino)propoxy]pyridin-2-yl] benzyloxycarbonylamine (200 mg).

(+) APCI-MASS (m/z): 492 (M+H)$^+$

The following compound was obtained according to a similar manner to that of Example 50.

EXAMPLE 51

4-[2-Hydroxy-3-(3-methoxy-6,7,8,9-tetrahydro-5H-benzocyclohepten-6-ylamino)propoxy]-1,3-dihydrobenzimidazol-2-one hydrochloride (+) APCI-MASS (m/z): 398 (M-HCl +H)$^+$

EXAMPLE 52

8-[[(2S)-2-Hydroxy-3-phenoxypropyl]amino]-6,7,8,9-tetrahydro-5H-benzocycloheptene-2-carboxylic acid methyl ester hydrochloride (8.40 g) was converted to the corresponding free base in a usual manner. The free base was dissolved in tetrahydrofuran (60 ml), and a solution of di-tert-butyl dicarbonate (4.52 g) in tetrahydrofuran (10 ml) was added to the mixture. After stirring overnight, the reaction mixture was evaporated in vacuo, and the residue was purified by column chromatography on silica gel eluting with a mixture of hexane and ethyl acetate (5:1 to 3:1) to afford 8-[N-tert-butoxycarbonyl-N-[(2S)-2-hydroxy-3-phenoxypropyl]-amino]-6,7,8,9-tetrahydro-5H-benzocycloheptene-2-carboxylic acid methyl ester (9.88 g).

NMR (DMSO-d$_6$, δ): 1.15–1.40 (1H, m), 1.41 (9H, s), 1.86–2.35 (3H, m), 2.68–3.60 (7H, m), 3.83 (3H, s), 3.85–4.08 (3H, m), 5.19 (1H, d, J=5.1 Hz), 6.89–6.99 (3H, m), 7.22–7.33 (3H, m), 7.70 (1H, dd, J=7.7 and 1.6 Hz), 7.75 (1H, s)

(+) ESI-MASS (m/z): 492 (M+Na)$^+$

EXAMPLE 53

To a solution of 8-[N-tert-butoxycarbonyl-N-[(2S)-2-hydroxy-3-phenoxypropyl]amino]-6,7,8,9-tetrahydro-5H-benzocycloheptene-2-carboxylic acid methyl ester (4.5 g) in methanol (45 ml) and tetrahydrofuran (15 ml) was added 1N sodium hydroxide aqueous solution. After stirring at room temperature for 6 hours, the reaction mixture was concentrated under reduced pressure, neutralized with 1N hydrochloric acid solution under ice-cooling. The product was extracted with ethyl acetate, and the organic layer was washed with brine, dried over magnesium sulfate and evaporated in vacuo to afford 8-[N-tert-butoxycarbonyl-N-[(2S)-2-hydroxy-3-phenoxypropyl]amino]-6,7,8,9-tetrahydro-5H-benzocycloheptene-2-carboxylic acid (4.48 g).

NMR (DMSO-d$_6$, δ): 1.19–1.40 (1H, m), 1.41 (9H, s), 1.89–2.37 (3H, m), 2.71–3.58 (7H, m), 3.80–4.03 (3H, m), 5.17 (1H, d, J=5.0 Hz), 6.88–6.95 (3H, m), 7.19–7.32 (3H, m), 7.67 (1H, d, J=7.7 Hz), 7.74 (1H, s)

(+) APCI-MASS (m/z): 356 (M-Boc+2H)$^+$

EXAMPLE 54

To a mixture of 8-[N-tert-butoxycarbonyl-N-[(2S)-2-hydroxy-3-phenoxypropyl]amino]-6,7,8,9-tetrahydro-5H-benzocycloheptene-2-carboxylic acid (0.30 g), 1-(3-dimethylaminopropyl)-3-ethylcarbodiimide hydrochloride (0.15 g) and 1-hydroxybenzotriazole (0.11 g) in dichloromethane (6 ml) was added a solution of methylamine in tetrahydrofuran (2.0M, 0.40 ml). The reaction mixture was stirred at room temperature overnight, and partitioned between ethyl acetate and aqueous sodium bicarbonate solution. The organic layer was separated, washed with brine, dried over magnesium sulfate and evaporated in vacuo. The residue was purified by column chromatography on silica gel eluting with a mixture of chloroform and methanol (100:1 to 10:1) to afford N-[(2S)-2-hydroxy-3-phenoxypropyl]-N-tert-butoxycarbonyl-(3-methylcarbamoyl-6,7,8,9-tetrahydro-5H-benzocyclohepten-6-yl)amine (0.13 g).

NMR (DMSO-d$_6$, δ): 1.16–1.35 (1H, m), 1.40 (9H, s), 1.87–2.24 (3H, m), 2.76 (3H, d, J=4.6 Hz), 2.70–2.92 (2H, m), 3.03–3.56 (5H, m), 3.85–4.02 (3H, m), 5.14 (1H, d, J=5.1 Hz), 6.89–6.95 (3H, m), 7.15 (1H, d, J=7.7 Hz), 7.28 (2H, dd, J=7.7 and 7.7 Hz), 7.55 (1H, d, J=7.7 Hz), 7.63 (1H, s), 8.28 (1H, t-like, J=4.6 Hz)

(+) ESI-MASS (m/z): 491 (M+Na)$^+$

The following compounds [Examples 55 and 56] were obtained according to a similar manner to that of Example 54.

EXAMPLE 55

N-[(2S)-2-Hydroxy-3-phenoxypropyl]-N-tert-butoxycarbonyl-(3-dimethylcarbamoyl-6,7,8,9-tetrahydro-5H-benzocyclohepten-6-yl)amine NMR (DMSO-d$_6$, δ): 1.19–1.38 (1H, m), 1.40 (9H, s), 1.90–2.08 (2H, m), 2.12–2.30 (1H, m), 2.68–3.10 (4H, m), 2.93 (6H, s), 3.18–3.60 (3H, m), 3.85–4.08 (3H, m), 5.16 (1H, br), 6.88–6.95 (3H, m), 7.12–7.17 (3H, m), 7.28 (2H, dd, J=8.0 and 8.0 Hz)

(+) ESI-MASS (m/z): 505 (M+Na)$^+$

EXAMPLE 56

N-[(2S)-2-Hydroxy-3-phenoxypropyl]-N-tert-butoxycarbonyl-(3-phenylcarbamoyl-6,7,8,9-tetrahydro-5H-benzocyclohepten-6-yl)amine NMR (DMSO-d$_6$, δ): 1.19–1.20 (1H, m), 1.41 (9H, s), 1.88–2.36 (3H, m), 2.75–3.60 (7H, m, 3.85–4.10 (3H, m), 5.19 (1H, d, J=5.0 Hz), 6.85–6.93 (3H, m), 7.09 (1H, dd, J=7.4 and 7.4 Hz), 7.22–7.39 (5H, m), 7.64–7.78 (4H, m), 10.11 (1H, s)

(+) ESI-MASS (m/z): 553 (M+Na)$^+$

EXAMPLE 57

To a solution of 8-[N-benzyl-N-[(2S)-2-hydroxy-3-phenoxypropyl]amino]-6,7,8,9-tetrahydro-5H-benzocycloheptene-2-carboxamide (3.00 g) in dry tetrahydrofuran (90 ml) was gradually added lithium aluminum hydride (1.02 g) under ice-cooling and nitrogen atmosphere. The mixture was then heated to reflux for 3 hours. Saturated sodium bicarbonate solution was added dropwise to the reaction mixture under ice-cooling, and the resulting precipitate was filtered off and washed with ethyl acetate. The filtrate was extracted with ethyl acetate, and the organic layer was washed with water and brine, dried over magnesium sulfate and evaporated in vacuo. The residue was purified by column chromatography on silica gel eluting with a mixture of chloroform and methanol (30:1 to 5:1) to afford (2S)-1-[N-(3-aminomethyl-6,7,8,9-tetrahydro-5H-benzocyclohepten-6-yl)-N-benzylamino]-3-phenoxy-2-propanol (2.75 g).

NMR (DMSO-$d_6$, δ): 1.00–1.20 (1H, m), 1.67–2.10 (3H, m) , 2.23–2.40 (1H, m) , 2.50–3.10 (8H, m) , 3.62 (2H, d, J=3.0 Hz), 3.70–3.86 (4H, m), 3.92–4.02 (1H, m), 4.78 (1H, br), 6.83–7.00 (5H, m), 7.05–7.38 (8H, m)

(+) APCI-MASS (m/z): 431 (M+H)$^+$

EXAMPLE 58

To a mixture of (2S)-1-[N-(3-aminomethyl-6,7,8,9-tetrahydro-5H-benzocyclohepten-6-yl)-N-benzylamino]-3-phenoxy-2-propanol (0.30 g) and triethylamine (0.107 ml) in dichloromethane (6 ml) was added dropwise acetyl chloride (0.05 ml) under ice-cooling. The mixture was stirred at room temperature overnight and partitioned between water and ethyl acetate. The organic layer was separated, washed with water and brine, dried over magnesium sulfate and evaporated in vacuo. The residue was purified by column chromatography on silica gel eluting with a mixture of chloroform and methanol (50:1). The product was treated with 4N hydrogen chloride in ethyl acetate and powdered from diisopropyl ether to afford N-6-[N'-benzyl-N'-(2S)-2-hydroxy-3-phenoxypropyl)amino]-6,7,8,9-tetrahydro-5H-benzocyclohepten-3-ylmethyl]acetamide (0.29 g).

NMR (DMSO-$d_6$, δ): 1.09–1.30 (1H, m), 1.86–1.90 (total 3H, s), 1.98–2.18 (2H, m), 2.38–2.62 (1H, m), 2.70–2.82 (2H, m), 3.03–3.68 (5H, m), 3.74–4.04 (3H, m), 4.10–4.24 (2H, m), 4.40–4.68 (2H, m), 6.01 (1H, br), 6.83–7.10 (6H, m), 7.24–7.34 (2H, m), 7.40–7.52 (3H, m), 7.65–7.82 (2H, m), 8.37 (1H, t, J=6.0 Hz), 9.68–10.24 (1H, br)

(+) APCI-MASS (m/z): 473 (M+H)$^+$

The following compounds [Example 59 to 61] were obtained according to a similar manner to that of Example 58.

EXAMPLE 59

N-[8-[N'-Benzyl-N'-[(2S)-2-hydroxy-3-phenoxypropyl]-amino]-6,7,8,9-tetrahydro-5H-benzocyclohepten-2-ylmethyl]-benzamide hydrochloride NMR (DMSO-$d_6$, δ): 1.09–1.28 (1H, m), 1.93–2.19 (2H, m), 2.40–2.60 (1H, m), 2.67–2.84 (2H, m), 2.98–3.50 (5H, m), 3.74–4.02 (3H, m), 4.32–4.56 (4H, m), 6.00 (1H, br), 6.83–6.98 (3H, m), 7.07–7.53 (11H, m), 7.66–7.78 (2H, m), 7.94 (2H, dd, J=8.3 and 8.3 Hz), 9.12 (1H, t, J=6.0 Hz), 9.81–10.38 (1H, br)

(+) APCI-MASS (m/z) 535 (M+H)$^+$

EXAMPLE 60

N-[8-[N'-Benzyl-[N'-(2S)-2-hydroxy-3-phenoxypropyl]-amino]-6,7,8,9-tetrahydro-5H-benzocyclohepten-2-ylmethyl]-methanesulfonamide hydrochloride NMR (DMSO-$d_6$, δ): 1.08–1.23 (1H, m), 1.97–2.18 (2H, m), 2.39–2.60 (1H, m), 2.66–2.80 (2H, m), 2.82, 2.89 (total 3H, s), 3.00–3.64 (5H, m), 3.74–4.13 (5H, m), 4.40–4.70 (2H, m), 5.95 (1H, br), 6.83–6.98 (3H, m), 7.09–7.60 (9H, m), 7.67–7.78 (2H, m), 9.73–10.36 (1H, br)

(+) APCI-MASS (m/z): 509 (M+H)$^+$

EXAMPLE 61

N-[8-[N'-Benzyl-N'-[(2S)-2-hydroxy-3-phenoxypropyl]-amino]-6,7,8,9-tetrahydro-5H-benzocyclohepten-2-ylmethyl]-benzenesulfonamide hydrochloride NMR (DMSO-$d_6$, δ): 1.05–1.23 (1H, m), 1.96–2.18 (2H, m), 2.41–2.85 (3H, m), 2.99–3.48 (5H, m), 3.70–4.03 (5H, m), 4.45–4.70 (2H, m), 5.98–6.06 (1H, br), 6.83–7.06 (5H, m), 7.23–7.34 (3H, m), 7.40–7.84 (10H, m), 8.12–8.22 (1H, m), 9.71–10.31 (1H, br)

(+) APCI-MASS (m/z): 571 (M+H)$^+$

EXAMPLE 62

A mixture of (2R)-1-(3-methylsulfonylamino-4-benzyloxy)phenyl-2,3-epoxypropane (39 mg), (RS)-N-benzyl-(3-methoxy-6,7,8,9-tetrahydro-5H-benzocyclohepten-6-yl)amine (58 mg), ytterbium triflate (113 mg) and dichloromethane (1 ml) was stirred at room temperature overnight. The reaction mixture was washed up in the usual manner. The crude product was dissolved in isopropylalchol (1.5 ml), heated with refluxing for 4.5 hours, evaporated and purified by column chromatography (silica gel, 20 cm$^3$, eluent; 20% ethyl acetate-toluene) to give (2R)-N-[3-(3-methylsulfonylamino-4-benzyloxy)phenyl-2-hydroxypropyl]-N-[(6RS)-(3-methoxy-6,7,8,9-tetrahydro-5H-benzocyclohepten-6-yl)]benzylamine (40.2 mg) as an oil.

IR (Film): 3272, 2927, 1610, 1508, 1456, 1332, 1261, 1161, 1122, 975 cm$^{-1}$

NMR (CDCl$_3$, δ): 1.4–1.8 (4H, m), 2.4–3.1 (11H, m), 2.88 (3H, d, J=2.4 Hz), 3.5–3.8 (1H, m), 3.79 (3H, s), 5.08 (2H, s), 6.6–6.8 (2H, m), 6.9–7.0 (3H, m), 7.1–7.5 (11H, m)

EXAMPLE 63

Under nitrogen, to a solution of N-benzyl-(3-methoxy-6,7,8,9-tetrahydro-5H-benzocyclohepten-6-yl)amine (120 mg) and (2S)-1-(4-acetylamino)phenoxy-2,3-epoxypropane (89 mg) in dichloromethane (10 ml) was added ytterbium (III) trifluoromethanesulfonate (50 mg) at room temperature, and the mixture was stirred at the same temperature for 3 hours. The resulting mixture was poured into saturated aqueous sodium bicarbonate solution and extracted with ethyl acetate. The organic layer was washed with brine, dried over magnesium sulfate and evaporated in vacuo. The residue was chromatographed (hexane-ethyl acetate) over silica gel to afford (2S)-1-[N-benzyl-N-(3-methoxy-6,7,8,9-tetrahydro-5H-benzocyclohepten-6-yl)amino]-3-(4-acetylaminophenoxy)-2-propanol (80 mg).

(+) APCI-MASS (m/z): 489 (M+H)$^+$

EXAMPLE 64

Under nitrogen, to a solution of 2-(8-benzylamino-6,7,8,9-tetrahydro-5H-benzocyclohepten-2-yloxy)-N-butylacetamide (200 mg) and (2S)-1-(1H-indol-5-yloxy)-2,3-epoxypropane (130 mg) in dichloromethane (10 ml) was added ytterbium(III) trifluoromethanesulfonate (33 mg) at room temperature, and the mixture was stirred at the same temperature for 3 hours. The resulting mixture was poured into saturated aqueous sodium bicarbonate solution and extracted with ethyl acetate. The organic layer was washed with brine, dried over magnesium sulfate and evaporated in vacuo. The residue was chromatographed (hexane-ethyl acetate) over silica gel to afford 2-[8-[N-benzyl-N-[(2S)-2-hydroxy-3-(1H-indol-5-yloxy)propyl]amino]-6,7,8,9-tetrahydro-5H-benzocyclohepten-2-yloxy]-N-butylacetamide (160 mg)

(+) APCI-MASS (m/z): 570 (M+H)+

EXAMPLE 65

Under nitrogen, to a solution of 2-(8-benzylamino-6,7,8,9-tetrahydro-5H-benzocyclohepten-2-yloxy)-N-butylacetamide (388 mg) and (2S)-1-(4-benzyloxyphenoxy)-2,3-epoxypropane (340 mg) in dichloromethane (10 ml) was added ytterbium(III) trifluoromethanesulfonate (63 mg) at room temperature, and the mixture was stirred at the same temperature for 3 hours. The resulting mixture was poured into saturated aqueous sodium bicarbonate solution and extracted with ethyl acetate. The organic layer was washed with brine, dried over magnesium sulfate and evaporated in vacuo. The residue was chromatographed (hexane-ethyl acetate) over silica gel to afford 2-[8-[N-benzyl-N-[(2S)-3-(4-benzyloxyphenoxy)-2-hydroxypropyl]amino]-6,7,8,9-tetrahydro-5H-benzocyclohepten-2-yloxy]-N-butylacetamide (300 mg).

(+) APCI-MASS (m/z): 637 (M+H)+

EXAMPLE 66

Under nitrogen, to a solution of N-benzyl-(3-hydroxy-6,7,8,9-tetrahydro-5H-benzocyclohepten-6-yl)amine hydrochloride (300 mg) and (2S)-1-phenoxy-2,3-epoxypropane (193 mg) in dichloromethane (10 ml) was added ytterbium (III) trifluoromethanesulfonate (61 mg) at room temperature, and the mixture was stirred at the same temperature for 3 hours. The resulting mixture was poured into saturated aqueous sodium bicarbonate solution and extracted with ethyl acetate. The organic layer was washed with brine, dried over magnesium sulfate and evaporated in vacuo. The residue was chromatographed (hexane-ethyl acetate) over silica gel to afford (2S)-1-[N-benzyl-N-(3-hydroxy-6,7,8,9-tetrahydro-5H-benzocyclohepten-6-yl)amino]-3-phenoxy-2-propanol (340 mg).

NMR (CDCl$_3$, δ): 1.20–140 (1H, m), 1.60–2.30 (4H, m), 2.50–2.95 (7H, m), 3.80–4.05 (5H, m), 6.50–6.75 (2H, m), 6.85–7.03 (4H, m), 7.20–7.38 (8H, m)

(+) APCI-MASS (m/z): 418 (M+H)+

EXAMPLE 67

Under nitrogen, to a solution of N-benzyl-(2,3-dimethoxy-6,7,8,9-tetrahydro-5H-benzocyclohepten-6-yl)amine (440 mg) and (2S)-1-phenoxy-2,3-epoxypropane (190 mg) in dichloromethane (10 ml) was added ytterbium (III) trifluoromethanesulfonate (157 mg) at room temperature, and the mixture was stirred at the same temperature for 3 hours. The resulting mixture was poured into saturated aqueous sodium bicarbonate solution and extracted with ethyl acetate. The organic layer was washed with brine, dried over magnesium sulfate and evaporated in vacuo. The residue was chromatographed (hexane-ethyl acetate) over silica gel to afford (2S)-1-[N-benzyl-N-(2,3-dimethoxy-6,7,8,9-tetrahydro-5H-benzocyclohepten-6-yl)amino]-3-phenoxy-2-propanol (400 mg).

(+) APCI-MASS (m/z): 462 (M+H)+

EXAMPLE 68

Under nitrogen, to a solution of N-benzyl-(1,4-dimethoxy-5,6,8,9-tetrahdydro-5H-benzocyclohepten-7-yl) amine (200 mg) and (2S)-1-phenoxy-2,3-epoxypropane (100 mg) in dichloromethane (10 ml) was added ytterbium (III) trifluoromethanesulfonate (80 mg) at room temperature, and the mixture was stirred at the same temperature for 3 hours. The resulting mixture was poured into saturated aqueous sodium bicarbonate solution and extracted with ethyl acetate. The organic layer was washed with brine, dried over magnesium sulfate and evaporated in vacuo. The residue was chromatographed (hexane-ethyl acetate) over silica gel to afford (2S)-1-[N-benzyl-N-(1,4-dimethoxy-5,6,8,9-tetrahydro-5H-benzocyclohepten-7-yl)amino]-3-phenoxy-2-propanol (70 mg).

(+) APCI-MASS (m/z): 462 (M+H)+

EXAMPLE 69

Under nitrogen, to a solution of N-benzyl-(3-methoxy-6,7,8,9-tetrahydro-5H-benzocyclohepten-5-yl)amine (187 mg) and (2S)-1-phenoxy-2,3-epoxypropane (100 mg) in dichloromethane (10 ml) was added ytterbium(III) trifluoromethanesulfonate (50 mg) at room temperature, and the mixture was stirred at the same temperature for 3 hours. The resulting mixture was poured into saturated aqueous sodium bicarbonate solution and extracted with ethyl acetate. The organic layer was washed with brine, dried over magnesium sulfate and evaporated in vacuo. The residue was chromatographed (hexane-ethyl acetate) over silica gel to afford (2S)-1-[N-benzyl-N-(3-methoxy-6,7,8,9-tetrahydro-5H-benzocyclohepten-5-yl)amino]-3-phenoxy-2-propanol (190 mg).

(+) APCI-MASS (m/z): 432 (M+H)+

EXAMPLE 70

To a solution of 1-[N-(3-aminomethyl-6,7,8,9-tetrahydro-5H-benzocyclohepten-6-yl)benzylamino]-3-phenoxy-2-propanol (150 mg) in N,N-dimethylformamide (2 ml) and 1N hydrochloric acid (0.8 ml) was added potassium cyanate (56.8 mg) at room temperature, and the mixture was stirred at the same temperature for 24 hours. The resulting mixture was poured into saturated aqueous sodium bicarbonate solution and extracted with ethyl acetate. The organic layer was washed with brine, dried over magnesium sulfate and evaporated in vacuo. The residue was chromatographed (hexane-ethyl acetate) over silica gel to afford N-[8-[N'-benzyl-N'-[(2S)-2-hydroxy-3-phenoxypropyl]amino]-6,7,8,9-tetrahydro-5H-benzocyclohepten-2-ylmethyl]urea (160 mg).

(+) APCI-MASS (m/z): 474 (M+H)+

EXAMPLE 71

To a solution of 1-[N-(3-aminomethyl-6,7,8,9-tetrahydro-5H-benzocyclohepten-6-yl) benzylamino]-3-phenoxy-2-propanol (140 mg) and triethylamine (0.046 ml) in tetrahydrofuran (10 ml) were added chloroformic acid 4-nitrophenyl ester (66.5 mg) and butylamine (0.030 ml) at room temperature, and the mixture was stirred at the same temperature for 18 hours. The resulting mixture was poured into saturated aqueous sodium bicarbonate solution and extracted with ethyl acetate. The organic layer was washed with brine, dried over magnesium sulfate and evaporated in vacuo. The residue was chromatographed (hexane-ethyl acetate) over silica gel to afford 1-[8-N-[benzyl-[(2S)-2-hydroxy-3-phenoxypropyl)amino]-6,7,8,9-tetrahydro-5H-benzocyclohepten-2-ylmethyl]-3-butylurea (110 mg).

(+) APCI-MASS (m/z): 530 (M+H)+

EXAMPLE 72

To a solution of (2S)-1-[N-(3-aminomethyl-6,7,8,9-tetrahydro-5H-benzocyclohepten-6-yl)benzylamino]-3- phenoxy-2-propanol (100 mg) in methanol (2 ml) was added tert-butylacrylate (0.033 ml) at room temperature, and the mixture was stirred at the same temperature for 18 hours. The resulting mixture was evaporated in vacuo. The residue was chromatographed (hexane-ethyl acetate) over silica gel to afford 3-(8-[N-benzyl-(2S)-(2-hydroxy-3-phenoxypropyl)amino]-6,7,8,9-tetrahydro-5H-benzocyclohepten-2-ylmethylamino]-propionic acid tert-butyl ester (100 mg).

(+) APCI-MASS (m/z): 559 (M+H)$^+$

EXAMPLE 73

Under nitrogen, to a solution of 2-(8-benzylamino-6,7,8,9-tetrahydro-5H-benzocyclohepten-2-yloxy)-N-butylacetamide (170 mg) and (2S)-1-(4-benzyloxy-3-methanesulfonylamino)phenoxy-2,3-epoxypropane (108 mg) in dichloromethane (10 ml) was added ytterbium(III) trifluoromethanesulfonate (56 mg) at room temperature, and the mixture was stirred at the same temperature for 3 hours. The resulting mixture was poured into saturated aqueous sodium bicarbonate solution and extracted with ethyl acetate. The organic layer was washed with brine, dried over magnesium sulfate and evaporated in vacuo. The residue was chromatographed (hexane-ethyl acetate) over silica gel to afford 2-[8-[N-benzyl-N-[(2S)-3-(4-benzyloxy-3-methanesulfonylamino) phenoxy-2-hydroxypropyl]amino]-6,7,8,9-tetrahydro-5H-benzocyclohepten-2-yloxy]-N-butylacetamide (120 mg).

NMR (CDCl$_3$, δ): 0.92 (3H, t, J=7.3 Hz), 1.20–1.65 (7H, m), 1.95–2.05 (1H, m), 2.60–2.80 (4H, m), 2.60–2.80 (4H, m), 2.87 (3H, s), 3.30–3.40 (2H, m), 3.70–4.00 (5H, m), 4.45 (2H, d, J=2.0 Hz), 5.05 (2H, s), 6.55–6.75 (2H, m), 6.80–7.25 (14H, m)

(+) APCI-MASS (m/z): 730 (M+H)$^+$

EXAMPLE 74

Under nitrogen, to a solution of N-benzyl-(3-methoxy-6,7,8,9-tetrahydro-5H-benzocyclohepten-6-yl)amine (487 mg) and (2S)-1-(4-benzyloxy-3-methanesulfonylamino) phenoxy-2,3-epoxypropane (338 mg) in dichloromethane (10 ml) was added ytterbium(III) trifluoromethanesulfonate (107 mg) at room temperature, and the mixture was stirred at the same temperature for 3 hours. The resulting mixture was poured into saturated aquous sodium bicarbonate solution and extracted with ethyl acetate. The organic layer was washed with brine, dried over magnesium sulfate and evaporated in vacuo. The residue was chromatographed (hexane-ethyl acetate) over silica gel to afford (2S)-1-[N-benzyl-N-(3-methoxy-6,7,8,9-tetrahydro-5H-benzocyclohepten-6-yl) amino]-3-(4-benzyloxy-3-methanesulfonylamino)phenoxy-2-propanol (750 mg).

(+) APCI-MASS (m/z): 432 (M+H)$^+$

EXAMPLE 75

A mixture of (2S)-1-[N-benzyl-N-(6,7,8,9-tetrahydro-2-hydroxy-5H-benzocyclohepten-6-yl) amino]-3-phenoxy-2-propanol (300 mg) and 10% Pd/C (50% wet, 80 mg) in methanol (4.5 ml) was stirred at room temperature in the presence of hydrogen at an atmospheric pressure for 2 hours and 30 minutes and filtered. The filtrate was evaporated in vacuo, and the residue was chromatographed (chloroform-methanol) over silica gel (6.0 g). The eluate was treated with 4N hydrogen chloride in ethyl acetate and evaporated in vacuo. The residue was triturated in diethyl ether, and the precipitated powder was collected by decantation to afford (2S)-1-(6,7,8,9-tetrahydro-2-hydroxy-5H-benzocyclohepten-6-yl) amino-3-phenoxy-2-propanol hydrochloride (238 mg) as a colorless powder.

mp: 53.5° C. (dec.)

IR (KBr): 3411, 2750–2650, 1241 cm$^{-1}$

NMR (DMSO-d$_6$, δ): 1.32 (1H, m), 1.75–2.05 (2H, m), 2.24 (1H, m), 2.62 (2H, m), 2.95–3.45 (5H, m), 4.00 (2H, m), 4.24 (1H, m), 5.90 (1H, d, J=4.5 Hz), 6.50–6.55 (2H, m), 6.95–7.00 (4H, m), 7.31 (2H, t, J=7.8 Hz), 8.77 (1H, br), 9.0 (1H, br), 9.28 (1H, s)

(+) APCI-MASS (m/z): 328 (M+H)$^+$ Anal. Calcd. for C$_{20}$H$_{26}$ClNO$_3$.0.5H$_2$O: C, 64.42; H, 7.30; N, 3.76. Found: C, 63.73; H, 7.37; N, 3.58.

EXAMPLE 76

The following compounds [Examples 76 and 77] were obtained according to a similar manner to that of Example 75.

(2S)-1-Phenoxy-3-(6,7,8,9-tetrahydro-1-hydroxy-5H-benzocyclohepten-6-yl)amino-2-propanol hydrochloride mp: 73–84° C. (dec.) (from diethyl ether)

IR (KBr): 3357 (br), 2850–2650, 1242 cm$^{-1}$

NMR (DMSO-d$_6$, δ) 1.23 (2H, m), 1.75–2.05 (2H, m), 2.28 (2H, m), 2.95–3.45 (5H, m), 4.00 (2H, m), 4.22 (1H, m), 5.90 (1H, J=4.9 Hz), 6.63–6.75 (2H, m), 6.87–7.00 (4H, m), 7.27–7.36 (2H, m), 8.74 (1H, br), 8.95 (1H, br), 9.34 (1H, s)

(+) APCI-MASS (m/z): 328 (M+H)$^+$ Anal. Calcd. for C$_{20}$H$_{26}$ClNO$_3$.1/4H$_2$O: C, 65.21; H, 7.25; N, 3.80. Found: C, 65.24; H, 7.50; N, 3.61.

EXAMPLE 77

1-(1,3-Dihydro-2-benzoimidazolon-4-yl)oxy-3-(6,7,8,9-tetrahydro-2-hydroxy-5H-benzocyclohepten-6-yl)amino-2-propanol hydrochloride mp 100.5° C. (dec.) (from diisopropyl ether)

IR (KBr): 3410 (br), 3257 (br), 2800–2650, 1695, 1259, 1244 cm$^{-1}$

NMR (DMSO-d$_6$, δ): 1.12–1.4 (1H, m), 1.75–2.2 (2H, m), 2.2–2.4 (1H, m), 2.4–2.8 (2H, m), 2.8–3.5 (5H, m), 3.95–4.3 (3H, m), 5.7 (1H, br), 6.51–6.66 (4H, m), 6.88 (1H, t, J=8.2 Hz), 6.99 (1H, d, J=6.9 Hz), 8.68 (1H, br), 8.93 (1H, br), 9.25 (1H, br)

(+) APCI-MASS (m/z): 384 (M+H)$^+$

EXAMPLE 78

A mixture of (2S)-1-[N-benzyl-N-(3-chloro-6,7,8,9-tetrahydro-2-hydroxy-5H-benzocyclohepten-6-yl)amino]-3-phenoxy-2-propanol hydrochloride (121 mg) and 10% Pd/C (50% wet, 18 mg) in chlorobenzene (1.8 ml) and MeOH (0.4 ml) was stirred at room temperature in the presence of hydrogen at an atmospheric pressure for 1 hour and filtered. The filtrate was evaporated in vacuo, and the residue was partitioned between ethyl acetate and a saturated aqueous solution of sodium bicarbonate. The organic layer was separated, washed with brine, dried over sodium sulfate and evaporated in vacuo. The residue was chromatographed (dichloromethane-methanol) over silica gel (2.0 g). The eluate was treated with 4N hydrogen chloride in ethyl acetate and evaporated in vacuo. The residue was triturated in diisopropyl ether, and the precipitated powder was collected by filtration to afford (2S)-1-(3-chloro-6,7,8,9-tetrahydro-2-hydroxy-5-H-benzocyclohepten-6-yl)amino-3- phenoxy-2-propanol hydrochloride (74 mg, 75%) as a colorless powder.

IR (KBr): 3384 (br), 2800–2600, 1242 cm$^{-1}$

NMR (DMSO-d$_6$, δ): 1.17–1.31 (1H, m), 1.84–1.99 (2H, m), 2.16–2.24 (1H, m), 2.61–2.74 (2H, m), 3.00–3.22 (4H, m), 3.98–4.24 (3H, m), 5.89 (1H, d, J=3.9 Hz), 6.77 (1H, m), 6.86–7.02 (3H, m), 7.14–7.32 (3H, m), 8.73 (1H, br), 8.88 (1H, br), 10.03 (1H, s)

(+) APCI-MASS (m/z): 362 and 364 (M+H)$^+$

EXAMPLE 79

A mixture of (2S)-1-[N-benzyl-N-(3-isopropoxy-6,7,8,9-tetrahydro-5H-benzocyclohepten-6-yl)amino]-3-phenoxy-2-propanol (281 mg) and 10% palladium on activated carbon (50% wet, 100 mg) in methanol (5 ml) was stirred at room temperature in the presence of hydrogen at an atmospheric pressure for 6 hours. After filtration, the filtrate was evaporated in vacuo, followed by treatment with 4N hydrogen chloride in ethyl acetate to give (2S)-1-(3-isopropoxy-6,7,8,9-tetrahydro-5H-benzocyclohepten-6-yl)amino-3-phenoxy-2-propanol hydrochloride (130 mg).

(+) APCI-MASS (m/z): 370 (M−HCl+H)$^+$

The following compounds [Examples 80 to 108] were obtained according to a similar manner to that of Example 79.

EXAMPLE 80

(2S)-1-(3-Hexyloxy-6,7,8,9-tetrahydro-5H-benzocyclohepten-6-yl)amino-3-phenoxy-2-propanol hydrochloride NMR (DMSO-d$_6$, δ): 0.8 (3H, m), 1.1–1.5 (7H, m), 1.6–2.15 (4H, m), 2.25–2.4 (1H, m), 2.5–2.8 (2H, m), 2.9–3.5 (5H, m), 3.85–4.1 (4H, m), 4.15–4.25 (1H, m), 5.9–6.05 (1H, m), 6.65–7.1 (6H, m), 7.2–7.4 (2H, m), 8.7–9.3 (2H, m)

(+) APCI-MASS (m/z): 412 (M+H)$^+$

EXAMPLE 81

(2S)-1-[3-(3-Cyano-pyridin-2-yl)oxy-6,7,8,9-tetrahydro-5H-benzocyclohepten-6-yl)amino]-3-phenoxy-2-propanol hydrochloride (+) ESI-MASS (m/z): 464 (M−HCl−H)$^+$

EXAMPLE 82

(2S)-1-[3-(2-Methoxyethoxy)-6,7,8,9-tetrahydro-5H-benzocyclohepten-6-yl]amino-3-phenoxy-2-propanol hydrochloride (+) APCI-MASS (m/z): 386 (M−HCl+H)$^+$

EXAMPLE 83

N-(2-Dimethylaminoethyl)-2-[8-[(2S)-2-hydroxy-3-phenoxypropyl]amino-6,7,8,9-tetrahydro-5H-benzocyclohepten-2-yloxy]acetamide dihydrochloride (+) APCI-MASS (m/z): 456 (M−HCl+H)$^+$

EXAMPLE 84

(2S)-1-(3-Amino-6,7,8,9-tetrahydro-5H-benzocyclohepten-6-yl)amino-3-phenoxy-2-propanol dihydrochloride (+) APCI-MASS (m/z): 327 (M−HCl+H)$^+$

EXAMPLE 85

(2S)-1-(3-Dimethylamino-6,7,8,9-tetrahydro-5H-benzocyclohepten-6-yl)amino-3-phenoxy-2-propanol hydrochloride (+) APCI-MASS (m/z): 355 (M−HCl+H)$^+$

EXAMPLE 86

(2S)-1-(3-Dimethylamino-6,7,8,9-tetrahydro-5H-benzocyclohepten-6-yl)amino-3-phenoxy-2-propanol hydrochloride (+) APCI-MASS (m/z): 355 (M−HCl+H)$^+$

EXAMPLE 87

N-[8-[(2S)-2-Hydroxy-3-phenoxypropyl]amino-6,7,8,9-tetrahydro-5H-benzocyclohepten-2-yl]acetamide hydrochloride (+) ESI-MASS (m/z): 369 (M−HCl+H)$^+$

EXAMPLE 88

N-[8-[(2S)-2-Hydroxy-3-phenoxypropyl]amino-6,7,8,9-tetrahydro-5H-benzocyclohepten-2-yl]benzamide hydrochloride (+) APCI-MASS (m/z): 431 (M−HCl+H)$^+$

EXAMPLE 89

N-[8-[(2S)-2-Hydroxy-3-phenoxypropyl]amino-6,7,8,9-tetrahydro-5H-benzocyclohepten-2-yl]methanesulfonamide hydrochloride (+) APCI-MASS (m/z): 405 (M−HCl+H)$^+$

EXAMPLE 90

N-[8-[(2S)-2-Hydroxy-3-phenoxypropyl]amino-6,7,8,9-tetrahydro-5H-benzocyclohepten-2-yl]benzenesulfonamide hydrochloride (+) APCI-MASS (m/z): 467 (M−HCl+H)$^+$

EXAMPLE 91

6-[(2S)-2-Hydroxy-3-phenoxypropyl]amino-3-methoxycarbonylamino-6,7,8,9-tetrahydro-5H-benzocycloheptene hydrochloride (+) APCI-MASS (m/z): 385 (M−HCl+H)$^+$

EXAMPLE 92

6-[(2S)-2-Hydroxy-3-phenoxypropyl]amino-3-phenoxycarbonylamino-6,7,8,9-tetrahydro-5H-benzocycloheptene hydrochloride (+) APCI-MASS (m/z): 447 (M−HCl+H)$^+$

EXAMPLE 93

N,N-Dimethyl-N'-[8-[(2S)-2-hydroxy-3-phenoxypropyl]amino-6,7,8,9-tetrahydro-5H-benzocyclohepten-2-yl]sulfonamide hydrochloride (+) APCI-MASS (m/z): 434 (M−HCl+H)$^+$

EXAMPLE 94

N-[8-[(2S)-2-Hydroxy-3-phenoxypropyl]amino-6,7,8,9-tetrahydro-5H-benzocyclohepten-2-yl]sulfonamide hydrochloride (+) APCI-MASS (m/z): 406 (M−HCl+H)$^+$

EXAMPLE 95

(2S)-3-Phenoxy-1-(6,7,8,9-tetrahydro-5H-benzocyclohepten-6-yl)amino-2-propanol hydrochloride (+) ESI-MASS (m/z): 312 (M−HCl+H)$^+$

EXAMPLE 96

(2S)-1-Phenoxy-3-(3-phenyl-6,7,8,9-tetrahydro-5H-benzocyclohepten-6-yl)amino-2-propanol hydrochloride (+) ESI-MASS (m/z): 388 (M–HCl+H)$^+$

EXAMPLE 97

(2S)-3-Phenylsulfonyl-1-(3-methoxy-6,7,8,9-tetrahydro-5H-benzocyclohepten-6-yl)amino-2-propanol hydrochloride (+) APCI-MASS (m/z): 390 (M–HCl+H)$^+$

EXAMPLE 98

1-(3-Methoxy-6,7,8,9-tetrahydro-5H-benzocyclohepten-6-yl)amino-3-phenylamino-2-propanol dihydrochloride (+) APCI-MASS (m/z): 341 (M–2HCl+H)$^+$

EXAMPLE 99

(2S)-1-(6-Aminopyridin-3-yl)oxy-3-(3-methoxy-6,7,8,9-tetrahydro-5H-benzocyclohepten-6-yl)amino-2-propanol hydrochloride (+) APCI-MASS (m/z): 358 (M–3HCl+H)$^+$

EXAMPLE 100

(2S)-1-(4-Fluorophenoxy)-3-(3-methoxy-6,7,8,9-tetrahydro-5H-benzocyclohepten-6-yl)amino-2-propanol hydrochloride NMR (DMSO-d$_6$, δ) 1.1–1.4 (1H, m), 1.7–2.1 (2H, m), 2.2–2.4 (1H, m), 2.6–2.8 (2H, m), 2.95–3.5 (5H, m), 3.72 (3H, s), 3.9–4.0 (2H, m), 4.22 (1H, br s), 5.93 (1H, br s), 6.71 (1H, dd, J=2.6 and 8.2 Hz), 6.82 (1H, dd, J=2.6 and 6.5 Hz), 6.9–7.25 (5H, m), 8.82 (1H, br s), 9.16 (1H, br s)

(+) APCI-MASS (m/z): 360 (M–HCl+H)$^+$

EXAMPLE 101

(2S)-1-(4-Methoxy-6,7,8,9-tetrahydro-5H-benzocyclohepten-6-yl)amino-3-phenoxy-2-propanol hydrochloride IR (KBr): 3369, 2937, 1591, 1452, 1259, 1236, 1074 cm$^{-1}$ NMR (DMSO-d$_6$, δ): 1.22–1.42 (1H, m), 1.80–2.10 (2H, m), 2.25–2.39 (1H, m), 2.66–2.83 (3H, m), 2.90–3.23 (3H, m), 3.53–3.60 (1H, m), 3.78 (3H, s), 3.98–4.05 (2H, m), 4.20–4.31 (1H, m), 5.91 (1H, br), 6.75 (1H, d, J=7.9 Hz), 6.86 (1H, d, J=7.9 Hz), 6.92–7.00 (3H, m), 7.12 (1H, dd, J=7.9 and 7.9 Hz), 7.32 (2H, dd, J=8.1 and 8.1 Hz), 8.89 (2H, br)

(+) APCI-MASS (m/z): 342 (M+H)$^+$

EXAMPLE 102

8-[(2S)-2-Hydroxy-3-phenoxypropyl]amino-6,7,8,9-tetrahydro-5H-benzocycloheptene-2-carboxylic acid methyl ester hydrochloride IR (KBr): 3378, 2950, 2796, 1716, 1438, 1280, 1243 cm$^{-1}$ NMR (DMSO-d$_6$, δ) 1.20–1.42 (1H, m), 1.81–2.13 (2H, m), 2.25–2.40 (1H, m), 2.74–2.91 (2H, m), 3.02–3.37 (5H, m), 3.84 (3H, s), 4.01 (2H, d, J=4.6 Hz), 4.20–4.36 (1H, m), 5.93 (1H, br), 6.92–6.99 (3H, m), 7.27–7.35 (3H, m), 7.76 (1H, d, J=7.8 Hz), 7.87 (1H, d, J=7.8 Hz), 8.92–9.18 (2H, br)

(+) ESI-MASS (m/z): 370 (M+H)$^+$

EXAMPLE 103

8-[(2S)-2-Hydroxy-3-phenoxypropyl]amino-6,7,8,9-tetrahydro-5H-benzocycloheptene-2-carboxamide hydrochloride IR (KBr): 3353, 2937, 1662, 1600, 1243 cm$^{-1}$ NMR (DMSO-d$_6$, δ): 1.21–1.42 (1H, m), 1.78–2.13 (2H, m), 2.24–2.40 (1H, m), 2.74–2.85 (2H, m), 3.02–3.44 (5H, m), 4.01 (2H, d, J=4.5 Hz), 4.18–4.30 (1H, m), 5.92 (1H, d, J=4.0 Hz), 6.92–6.99 (3H, m), 7.21 (1H, d, J=7.8 Hz), 7.27–7.35 (3H, m), 7.67 (1H, d, J=7.8 Hz), 7.79 (1H, d, J=2.0 Hz), 7.91 (1H, s), 8.84 (1H, br s), 9.12 (1H, br s)

(+) APCI-MASS (m/z): 355 (M+H)$^+$

EXAMPLE 104

N-[8-[(2S)-2-Hydroxy-3-phenoxypropyl]amino-6,7,8,9-tetrahydro-5H-benzocyclohepten-2-ylmethyl]acetamide hydrochloride IR (KBr) 3278, 2935, 1648, 1494, 1241 cm$^{-1}$ NMR (DMSO-d$_6$, δ): 1.17–1.37 (1H, m), 1.78–2.10 (2H, m), 1.86 (3H, s), 2.25–2.37 (1H, m), 2.67–2.77 (2H, m), 2.98–3.40 (5H, m), 4.01 (2H, d, J=3.9 Hz), 4.15–4.35 (1H, m), 4.19 (2H, d, J=5.7 Hz), 6.92–7.10 (6H, m), 7.31 (2H, dd, J=7.8 and 7.8 Hz), 8.30–8.40 (1H, m), 8.85 (1H, br s), 9.20 (1H, br s)

(+) APCI-MASS (m/z): 383 (M+H)$^+$

EXAMPLE 105

N-[8-[(2S)-2-Hydroxy-3-phenoxypropyl]amino-6,7,8,9-tetrahydro-5H-benzocyclohepten-2-ylmethyl]benzamide hydrochloride IR (KBr): 3330, 2933, 1639, 1538, 1455, 1241 cm$^{-1}$ NMR (DMSO-d$_6$, δ) 1.18–1.38 (1H, m), 1.79–2.08 (2H, m), 2.23–2.37 (1H, m), 2.68–2.78 (2H, m), 2.98–3.30 (5H, m), 3.97–4.03 (2H, m), 4.16–4.28 (1H, m), 4.44 (2H, d, J=5.4 Hz), 5.91 (1H, br), 6.91–6.98 (3H, m), 7.10–7.18 (3H, m), 7.30 (2H, dd, J=7.7 and 7.7 Hz), 7.41–7.57 (3H, m), 7.91 (2H, d, J=7.7 Hz), 8.75–9.10 (2H, br), 9.03–9.13 (1H, m)

(+) APCI-MASS (m/z): 445 (M+H)$^+$

EXAMPLE 106

N-[8-[(2S)-2-Hydroxy-3-phenoxypropyl]amino-6,7,8,9-tetrahydro-5H-benzocyclohepten-2-ylmethyl]methanesulfonamide hydrochloride IR (KBr): 3326, 2933, 1594, 1496, 1313, 1241, 1147 cm$^{-1}$ NMR (DMSO-d$_6$, δ): 1.15–1.38 (1H, m), 1.75–2.09 (2H, m), 2.23–2.37 (1H, m), 2.68–2.78 (2H, m), 2.87 (3H, s), 2.93–3.32 (5H, m), 4.00 (2H, d, J=4.1 Hz), 4.10 (2H, d, J=6.3 Hz), 4.17–4.30 (1H, m), 5.93 (1H, br), 6.91–7.00 (3H, m), 7.11–7.20 (3H, m), 7.31 (2H, dd, J=7.8 and 7.8 Hz), 7.50–7.59 (1H, m), 8.80–9.10 (2H, br)

(+) APCI-MASS (m/z): 419 (M+H)$^+$

EXAMPLE 107

N-[8-[(2S)-2-Hydroxy-3-phenoxypropyl]amino-6,7,8,9-tetrahydro-5H-benzocyclohepten-2-ylmethyl]benzenesulfonamide hydrochloride IR (KBr): 2935, 1594, 1496, 1448, 1322, 1241, 1157 cm$^{-1}$ NMR (DMSO-d$_6$, δ): 1.13–1.38 (1H, m), 1.75–2.08 (2H, m), 2.24–2.38 (1H, m), 2.65–2.75 (2H, m), 2.92–3.35 (5H, m), 3.92 (2H, d, J=6.2 Hz), 4.01 (2H, d, J=4.4 Hz), 4.18–4.30 (1H, m), 5.92 (1H, br), 6.92–7.02 (5H, m), 7.10 (1H, s), 7.31 (2H, dd, J=7.8 and 7.8 Hz), 7.50–7.68 (3H, m), 7.79 (2H, d, J=7.8 Hz), 8.12–8.22 (1H, m), 8.86 (2H, br)

(+) APCI-MASS (m/z): 481 (M+H)$^+$

EXAMPLE 108

1-(3-Methoxy-6,7,8,9-tetrahydro-5H-benzocyclohepten-6-yl)amino-4-phenyl-2-butanol hydrochloride (+) APCI-MASS (m/z): 340 (M−HCl+H)$^+$

EXAMPLE 109

A solution of N-(3-ethoxy-6,7,8,9-tetrahydro-5H-benzocyclohepten-6-yl)-N-[(2S)-3-phenoxy-2-(triethylsilyloxy)propyl]-tert-butoxycarbonylamine (115 mg) and concentrated hydrochloric acid (0.5 ml) in methanol (5 ml) was stirred at room temperature for 48 hours. The mixture was evaporated in vacuo. The residue was triturated with diethyl ether-diisopropyl ether, followed by decantation and dryness in vacuo to give (2S)-1-(3-ethoxy-6,7,8,9-tetrahydro-5H-benzocyclohepten-6-yl)amino-3-phenoxy-2-propanol hydrochloride (30 mg).

NMR (DMSO-d$_6$, δ) 1.1–1.4 (4H, m), 1.7–2.1 (2H, m), 2.2–2.35 (1H, m), 2.55–2.75 (2H, m), 2.9–3.4 (5H, m), 3.9–4.1 (4H, m), 4.25 (1H, br s), 5.9–6.0 (1H, m), 6.69 (1H, dd, J=2.5 and 8.2 Hz), 6.82 (1H, dd, J=2.4 and 6.8 Hz), 6.9–7.1 (4H, m), 7.31 (2H, t, J=7.9 Hz), 8.7–9.4 (2H, m)

(+) APCI-MASS (m/z): 356 (M+H)$^+$

EXAMPLE 110

To N-(3-isopropoxy-6,7,8,9-tetrahydro-5H-benzocyclohepten-6-yl)-N-[(2S)-3-phenoxy-2-(triethylsilyloxy)propyl]-tert-butoxycarbonylamine (79 mg) was added 4N hydrogen chloride in ethyl acetate (3 ml) at room temperature, and the mixture was stirred at room temperature for 1 hour. After evaporation in vacuo, the residue was triturated with diisopropyl ether and dried in vacuo to give (2S)-1-(3-isopropoxy-6,7,8,9-tetrahydro-5H-benzocyclohepten-6-yl)amino-3-phenoxy-2-propanol hydrochloride (35 mg)

(+) APCI-MASS (m/z): 370 (M−HCl+H)$^+$

The following compounds [Examples 111 to 116] were obtained according to a similar manner to that of Example 110.

EXAMPLE 111

(2S)-1-(3-Allyloxy-6,7,8,9-tetrahydro-5H-benzocyclohepten-6-yl)amino-3-phenoxy-2-propanol hydrochloride (−) ESI-MASS (m/z): 402 (M−HCl−H)$^+$

EXAMPLE 112

(2S)-1-(3-Cyclopentyloxy-6,7,8,9-tetrahydro-5H-benzocyclohepten-6-yl)amino-3-phenoxy-2-propanol hydrochloride (+) APCI-MASS (m/z): 396 (M−HCl+H)$^+$

EXAMPLE 113

(2S)-1-(3-Benzyloxy-6,7,8,9-tetrahydro-5H-benzocyclohepten-6-yl)amino-3-phenoxy-2-propanol hydrochloride (+) APCI-MASS (m/z): 418 (M−HCl+H)$^+$

EXAMPLE 114

(2S)-1-(3-Phenethyloxy-6,7,8,9-tetrahydro-5H-benzocyclohepten-6-yl)amino-3-phenoxy-2-propanol hydrochloride (+) APCI-MASS (m/z): 432 (M−HCl+H)$^+$

EXAMPLE 115

(2S)-1-(3-Carbamoyloxy-6,7,8,9-tetrahydro-5H-benzocyclohepten-6-yl)amino-3-phenoxy-2-propanol hydrochloride (+) APCI-MASS (m/z) 371 (M−HCl+H)$^+$

EXAMPLE 116

(2S)-1-(3-Dimethylsulfonyloxy-6,7,8,9-tetrahydro-5H-benzocyclohepten-6-yl)amino-3-phenoxy-2-propanol NMR (DMSO-d$_6$, δ) 1.2–1.45 (1H, m), 1.7–2.1 (2H, m), 2.3–2.4 (1H, m), 2.7–3.35 (7H, m), 2.90 (6H, m), 4.00 (2H, d, J=8.6 Hz), 4.2–4.35 (1H, m), 6.9–7.35 (8H, m)

(+) APCI-MASS (m/z): 435 (M−HCl+H)$^+$

EXAMPLE 117

To a solution of N-(3-fluoromethoxy-6,7,8,9-tetrahydro-5H-benzocyclohepten-6-yl)-N-[(2S)-2-hydroxy-3-phenoxypropyl]-tert-butoxycarbonylamine (41 mg) in ethyl acetate (2 ml) was added 4N hydrogen chloride in ethyl acetate (0.45 ml) at room temperature, and the mixture was stirred at the same temperature for 5.5 hours. The mixture was poured into a mixture of saturated aqueous sodium hydrogencarbonate and ethyl acetate, followed by being made basic with saturated aqueous sodium hydrogencarbonate. After separation, the organic layer was dried over anhydrous magnesium sulfate and evaporated in vacuo. The residue was purified by preparative thin layer chromatography (silica gel, chloroform:methanol=10:1) to give (2S)-1-(3-fluoromethoxy-6,7,8,9-tetrahydro-5H-benzocyclohepten-6-yl)amino-3-phenoxy-2-propanol (23 mg).

(+) APCI-MASS (m/z): 360 (M+H)$^+$

EXAMPLE 118

A mixture of 2-[8-[N-benzyl-N-[(2S)-2-hydroxy-3-phenoxypropyl]amino]-6,7,8,9-tetrahydro-5H-benzocyclohepten-2-yloxy]acetamide methanesulfonate (240 mg) and 10% palladium on activated carbon (50% wet, 50 mg) in ethanol (5 ml) was stirred at room temperature in the presence of hydrogen at an atmospheric pressure for 2 hours. After filtration, the filtrate was evaporated in vacuo and followed by trituration with diisopropyl ether to give 2-[8-[(2S)-2-hydroxy-3-phenoxypropyl]amino-6,7,8,9-tetrahydro-5H-benzocyclohepten-2-yloxy]acetamide methanesulfonate (187 mg).

(+) APCI-MASS (m/z): 385 (M−MsOH+H)$^+$

EXAMPLE 119

A solution of 2-[8-[N-benzyl-N-[(2S)-2-hydroxy-3-phenoxypropyl]amino]-6,7,8,9-tetrahydro-5H-benzocyclohepten-2-yloxy]acetic acid ethyl ester (200 mg) and ethylamine (70% in water, 77 μl) in methanol (2 ml) were stirred at room temperature for 12 hours. After evaporation in vacuo, the crude product and 10% palladium on activated carbon (50% wet, 60 mg) in methanol (2 ml) were stirred at room temperature in the presence of hydrogen at an atmospheric pressure for 2.5 hours. After filtration, the filtrate was evaporated in vacuo. The residue was purified by column chromatography on silica gel (chloroform:methanol=10:1) and followed by treatment with 4N hydrogen chloride in ethyl acetate to give N-ethyl-2-[8-[(2S)-2-hydroxy-3-phenoxypropyl]amino-6,7,8,9- tetrahydro-5H-benzocyclohepten-2-yloxy]acetamide hydrochloride (120 mg).

NMR (DMSO-d$_6$, δ): 1.0–1.1 (3H, m), 1.1–1.4 (1H, m), 1.7–2.1 (2H, m), 2.25–2.4 (1H, m), 2.6–2.8 (2H, m), 2.9–3.7 (7H, m), 3.95–4.1 (2H, m), 4.15–4.35 (1H, m), 4.40 (2H, s), 6.73 (1H, dd, J=2.6 and 8.3 Hz), 6.85–7.1 (5H, m), 7.31 (2H, t, J=8.0 Hz), 8.15–8.2 (1H, m), 8.7–9.3 (2H, m)

EXAMPLE 120

A solution of 2-[8-[N-benzyl-N-[(2S)-2-hydroxy-3-phenoxypropyl]amino-6,7,8,9-tetrahydro-5H-benzocyclohepten-2-yloxy]acetic acid ethyl ester (220 mg) and n-hexylamine (173 μl) in methanol (2 ml) was stirred at room temperature for 36 hours. And then to this one was added 10% palladium on activated carbon (50% wet, 60 mg), and the mixture was stirred at room temperature in the presence of hydrogen at an atmospheric pressure for 4 hours. After filtration, the filtrate was evaporated in vacuo. The residue was purified by preparative thin layer chromatography (silica gel, chloroform:methanol=10:1) and followed by treatment with 4N hydrogen chloride in ethyl acetate to give N-hexyl-2-[8-[(2S)-2-hydroxy-3-phenoxypropyl]amino-6,7,8,9-tetrahydro-5H-benzocyclohepten-2-yloxy]acetamide hydrochloride (169 mg).

(+) APCI-MASS (m/z): 469 (M–HCl+H)$^+$

The following compound was obtained according to a similar manner to that of Example 120.

EXAMPLE 121

2-[8-[(2S)-2-Hydroxy-3-phenoxypropyl]amino-6,7,8,9-tetrahydro-5H-benzocyclohepten-2-yloxy]-N-(2-methoxyethyl)acetamide hydrochloride NMR (DMSO-d$_6$, δ): 1.1–1.4 (1H, m), 1.7–2.1 (2H, m), 2.25–2.4 (1H, m), 2.6–2.8 (2H, m), 3.0–3.45 (12H, m), 3.95–4.1 (2H, m), 4.2–4.35 (1H, m), 4.43 (2H, s), 5.9–6.0 (1H, m), 6.7–6.8 (1H, m), 6.85–7.1 (5H, m), 7.25–7.4 (2H, m), 8.0–8.1 (1H, m), 8.7–9.3 (2H, m)

(+) APCI-MASS (m/z): 443 (M–HCl+H)$^+$

EXAMPLE 122

To a solution of N-[3-(N'-butylmethylcarbamoyl)methoxy-6,7,8,9-tetrahydro-5H-benzocyclohepten-6-yl]-N-[(2S)-2-hydroxy-3-phenoxypropyl]-tert-butoxycarbonylamine (85 mg) in ethyl acetate (2 ml) was added 4N hydrogen chloride in ethyl acetate (1 ml) at 5° C., and the mixture was stirred at room temperature for 2 hours. After evaporation in vacuo, the residue was triturated with diisopropyl ether and dried in vacuo to give N-butyl-2-[8-[(2S)-2-hydroxy-3-phenoxypropyl]amino-6,7,8,9-tetrahydro-5H-benzocyclohepten-2-yloxy]-N-methylacetamide hydrochloride (45 mg).

NMR (DMSO-d$_6$, δ): 0.88 (3H, q, J=7.3 Hz), 1.10–1.65 (5H, m), 1.70–2.16 (2H, m), 2.23–2.40 (1H, m), 2.58–3.43 (12H, m), 3.85–4.10 (2H, m), 4.17–4.35 (1H, m), 4.73 (2H, s), 5.83–5.99 (1H, m), 6.59–7.08 (6H, m), 7.31 (2H, t, J=7.7 Hz), 8.81 (1H, br s), 9.15 (1H, br s)

(+) APCI-MASS (m/z): 455 (M+H)$^+$

The following compounds [Examples 123 to 128] were obtained according to a similar manner to that of Example 122.

EXAMPLE 123

N-sec-Butyl-2-[8-[(2S)-2-hydroxy-3-phenoxypropyl]amino-6,7,8,9-tetrahydro-5H-benzocyclohepten-2-yloxy]acetamide hydrochloride (+) APCI-MASS (m/z): 441 (M+H)$^+$

EXAMPLE 124

N-Cyclohexyl-2-[8-[(2S)-2-hydroxy-3-phenoxypropyl]amino-6,7,8,9-tetrahydro-5H-benzocyclohepten-2-yloxy]acetamide hydrochloride (+) APCI-MASS (m/z): 467 (M+H)$^+$

EXAMPLE 125

N-Benzyl-2-[8-[(2S)-2-hydroxy-3-phenoxypropyl]amino-6,7,8,9-tetrahydro-5H-benzocyclohepten-2-yloxy]acetamide hydrochloride (+) APCI-MASS (m/z): 475 (M+H)$^+$

EXAMPLE 126

2-[8-[(2S)-2-Hydroxy-3-phenoxypropyl]amino-6,7,8,9-tetrahydro-5H-benzocyclohepten-2-yloxy]-N-(2-methylthioethyl)acetamide hydrochloride (+) APCI-MASS (m/z): 459 (M+H)$^+$

EXAMPLE 127

6-[(2S)-2-Hydroxy-3-phenoxypropyl]amino-3-piperidinocarbonylmethoxy-6,7,8,9-tetrahydro-5H-benzocycloheptene hydrochloride (+) APCI-MASS (m/z): 453 (M+H)$^+$

EXAMPLE 128

2-[8-[(2S)-2-Hydroxy-3-phenoxypropyl]amino-6,7,8,9-tetrahydro-5H-benzocyclohepten-2-yloxy]-N-(1H-indol-5-yl)acetamide hydrochloride NMR (DMSO-d$_6$, δ): 1.14–1.49 (1H, m), 1.70–2.12 (2H, m), 2.25–2.39 (1H, m), 2.57–2.82 (2H, m), 2.94–4.13 (7H, m), 4.19–4.32 (1H, m), 4.52–4.78 (2H, m), 6.72–7.49 (13H, m), 7.50–7.93 (1H, m), 8.69–9.33

(+) APCI-MASS (m/z): 500 (M+H)$^+$

EXAMPLE 129

Under nitrogen, to a solution of (2S)-1-amino-3-phenoxy-2-propanol (280 mg) in 1,2-dichloroethane (10 ml) were added 3-chloro-5,7,8,9-tetrahydrobenzocyclohepten-6-one (300 mg), sodium triacetoxyborohydride (820 mg) and acetic acid (0.26 ml) at room temperature, and the mixture was stirred at the same temperature for 6.5 hours. The resulting mixture was poured into aqueous 1N sodium hydroxide and extracted with ethyl acetate. The organic layer was washed with brine, dried over anhydrous magnesium sulfate and evaporated in vacuo. The residue was purified by column chromatography on silica gel (chloroform:methanol=20:1 to 10:1) and followed by treatment with 4N hydrogen chloride in ethyl acetate to give (2S)-1-(3-chloro-6,7,8,9-tetrahydro-5H-benzocyclohepten-6-yl)amino-3-phenoxy-2-propanol hydrochloride (260 mg).

(+) ESI-MASS (m/z): 346, 348 (M–HCl+H)$^+$

The following compounds [Examples 130 and 131] were obtained according to a similar manner to that of Example 129.

EXAMPLE 130

(2S)-1-(3-Nitro-6,7,8,9-tetrahydro-5H-benzocyclohepten-6-yl)amino-3-phenoxy-2-propanol hydrochloride (+) ESI-MASS (m/z): 357 (M–HCl+H)$^+$

EXAMPLE 131

(2S)-1-(3-Methyl-6,7,8,9-tetrahydro-5H-benzocyclohepten-6-yl)amino-3-phenoxy-2-propanol hydrochloride (+) ESI-MASS (m/z): 325 (M−HCl+H)$^+$

EXAMPLE 132

A mixture of (2S)-1-[N-benzyl-N-(2-chloro-3-methoxy-6,7,8,9-tetrahydro-5H-benzocyclohepten-6-yl) amino]-3-phenoxy-2-propanol (172 mg) and 10% palladium on activated carbon (50% wet, 50 mg) in a mixture of chlorobenzene (2 ml) and methanol (2 ml) was stirred at room temperature in the presence of hydrogen at an atmospheric pressure for 2 hours. After filtration, the filtrate was evaporated in vacuo. The residue was purified by column chromatography on silica gel (chloroform:methanol=20:1 to 10:1) and followed by treatment with 4N hydrogen chloride in ethyl acetate to give 1-(2-chloro-3-methoxy-6,7,8,9-tetrahydro-5H-benzocyclohepten-6-yl)amino-3-phenoxy-2-propanol hydrochloride (95 mg).

(+) APCI-MASS (m/z): 376, 378 (M−HCl+H)$^+$

EXAMPLE 133

Under nitrogen, to a solution of 3-methoxy-6,7,8,9-tetrahydro-5H-benzocyclohepten-6-ylamine (330 mg) and (2S)-1-phenylthio-2,3-epoxypropane (290 mg) in dichloromethane (5 ml) was added ytterbium(III) trifluoromethanesulfonate (110 mg) at room temperature, and the mixture was stirred at the same temperature for 24 hours. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (chloroform:methanol=50:1 to 20:1) followed by treatment with 4N hydrogen chloride in ethyl acetate to give (2S)-1-(3-methoxy-6,7,8,9-tetrahydro-5H-benzocyclohepten-6-yl) amino-3-phenylthio-2-propanol hydrochloride (360 mg).

(+) APCI-MASS (m/z): 358 (M−HCl+H)$^+$

EXAMPLE 134

8-[(2S)-2-Hydroxy-3-phenoxypropyl]amino-6,7,8,9-tetrahydro-5H-benzocycloheptene-2-carboxylic acid methyl ester hydrochloride was converted to the corresponding free base in a usual manner. A solution of the base (91 mg) in methanol (1 ml) and 1N sodium hydroxide aqueous solution (0.246 ml) was stirred at 70° C. for 6 hours and evaporated in vacuo. The residue was triturated in diisopropyl ether, and the precipitated powder was collected by filtration to afford sodium 8-[(2S)-2-hydroxy-3-phenoxypropyl]amino-6,7,8,9-tetrahydro-5H-benzocycloheptene-2-carboxylate (74 mg).

IR (KBr): 3380, 2925, 1592, 1550,1386, 1245 cm$^{-1}$

NMR (DMSO-d$_6$, δ) 1.23–1.70 (3H, m), 1.75–2.06 (2H, m), 2.38–2.90 (7H, m), 3.79–3.98 (3H, m), 5.11 (1H, br), 6.87–6.98 (4H, m), 7.27 (2H, dd, J=8.0 and 8.0 Hz), 7.58 (1H, d, J=7.5 Hz), 7.65 (1H, s)

(+) ESI-MASS (m/z): 356 (M−Na+2H)$^+$, 378 (M+H)$^+$

EXAMPLE 135

A solution of N-[(2S)-2-hydroxy-3-phenoxypropyl]-N-(3-methylcarbamoyl-6,7,8,9-tetrahydro-5H-benzocyclohepten-6-yl)-tert-butoxycarbonylamine (108 mg) in ethyl acetate (1 ml) was treated with 4N hydrogen chloride in ethyl acetate solution (0.58 ml) overnight. The mixture was evaporated in vacuo and triturated in diisopropyl ether, and the precipitated powder was collected by filtration to afford 6-[(2S)-2-hydroxy-3-phenoxypropyl] amino-3-methylcarbamoyl-6,7,8,9-tetrahydro-5H-benzocycloheptene hydrochloride (86 mg).

IR (KBr): 3332, 2937, 1631, 1457, 1241 cm$^{-1}$

NMR (DMSO-d$_6$, δ): 1.22–1.42 (1H, m), 1.80–2.11 (2H, m), 2.23–2.39 (1H, m), 2.77 (3H, d, J=4.4 Hz), 2.79–2.86 (2H, m), 3.02–3.45 (5H, m), 4.00 (2H, d, J=4.0 Hz), 4.19–4.30 (1H, m), 5.83 (1H, br), 6.92–6.99 (3H, m), 7.21 (1H, d, J=7.8 Hz), 7.31 (2H, dd, J=8.0 and 8.0 Hz), 7.62 (1H, d, J=7.3 Hz), 7.75 (1H, s), 8.40 (1H, t like, J=4.4 Hz), 8.81 (1H, br s), 9.09 (1H, br s)

(+) ESI-MASS (m/z): 369 (M+H)$^+$

The following compounds [Examples 136 and 137] were obtained according to a similar mannder to that of Example 135.

EXAMPLE 136

6-[(2S)-2-Hydroxy-3-phenoxypropyl]amino-3-dimethylcarbamoyl-6,7,8,9-tetrahydro-5H-benzocycloheptene hydrochloride IR (KBr) 3382, 2935, 1602, 1492, 1241 cm$^{-1}$ NMR (DMSO-d$_6$, δ) 1.22–1.43 (1H, m), 1.83–2.10 (2H, m), 2.23–2.38 (1H, m), 2.76–2.83 (2H, m), 2.94 (6H, s), 3.00–3.40 (5H, m), 3.97–4.03 (2H, m), 4.18–4.30 (1H, m), 6.90–7.02 (3H, m), 7.19–7.35 (5H, m), 8.80 (1H, br), 9.10 (1H, br)

(+) ESI-MASS (m/z): 383 (M+H)$^+$

EXAMPLE 137

6-[(2S)-2-Hydroxy-3-phenylpropyl]amino-3-phenylcarbamoyl-6,7,8,9-tetrahydro-5H-benzocycloheptene hydrochloride IR (KBr): 3380, 2937, 1648, 1598, 1536, 1498, 1241 cm$^{-1}$ NMR (DMSO-d$_6$, δ): 1.20–1.44 (1H, m), 1.80–2.18 (2H, m), 2.20–2.40 (1H, m), 2.78–2.90 (2H, m), 3.02–3.40 (5H, m), 3.98–4.08 (2H, m), 4.18–4.31 (1H, m), 5.92 (1H, d, J=4.9 Hz), 6.91–6.99 (4H, m), 7.09 (1H, dd, J=7.3 and 7.3 Hz), 7.26–7.39 (5H, m), 7.75–7.87 (4H, m), 8.76 (1H, br), 8.91 (1H, br), 10.21 (1H, s)

(+) ESI-MASS (m/z): 431 (M+H)$^+$

EXAMPLE 138

To N-(3-hydroxymethyl-6,7,8,9-tetrahydro-5H-benzocyclohepten-6-yl)-N-[(2S)-3-phenoxy-2-(triethylsilyloxy)propyl]-tert-butoxycarbonylamine (200 mg) was added 4N hydrogen chloride in ethyl acetate (6 ml) at room temperature, and the mixture was stirred at the same temperature for 1 hour. After evaporation in vacuo, the residue was dissolved into a mixture of saturated aqueous sodium hydrogencarbonate and ethyl acetate. After separation, the organic layer was washed with brine, dried over anhydrous magnesium sulfate and evaporated in vacuo. The residue was purified by preparative thin layer chromatography (silica gel, chloroform:methanol=5:1) and followed by treatment with 4N hydrogen chloride in ethyl acetate to give (2S)-1-(3-hydroxymethyl-6,7,8,9-tetrahydro-5H-benzocyclohepten-6-yl)amino-3-phenoxy-2-propanol hydrochloride (45 mg).

(+) APCI-MASS (m/z): 342 (M−HCl+H)$^+$

EXAMPLE 139

A solution of N-(3-hydroxymethyl-6,7,8,9-tetrahydro-5H-benzocyclohepten-6-yl)-N-[(2S)-3-phenoxy-2-(triethylsilyloxy)propyl]-tert-butoxycarbonylamine (188 mg) in ethyl acetate (2 ml) was treated with 4N hydrogen chloride in ethyl acetate (2 ml) for 3 hours. The mixture was evaporated in vacuo and washed with diethyl ether three times. The residue was triturated in diisopropyl ether, and precipitated powder was collected by filtration to afford 6-[(2S)-2-hydroxy-3phenoxypropyl]amino-3-acetyloxymethyl-6,7,8,9-tetrahydro-5H-benzocycloheptene (113 mg).

NMR (DMSO-$d_6$, δ): 1.12–1.41 (1H, m), 1.75–2.10 (2H, m), 2.05 (3H, s), 2.22–2.39 (1H, m), 2.65–2.85 (2H, m), 2.97–3.37 (5H, m), 3.94–4.04 (2H, m), 4.18–4.35 (1H, m), 5.02 (2H, s), 5.93 (1H, d, J=4.3 Hz), 6.92–7.00 (3H, m), 7.08–7.38 (5H, m), 8.89 (1H, br), 9.27 (1H, br)

(+) APCI-MASS (m/z): 384 (M+H)$^+$

The following compound was obtained according to a similar manner to that of Example 139.

EXAMPLE 140

(2S)-1-(3-Dimethylaminomethyl-6,7,8,9-tetrahydro-5H-benzocyclohepten-6-yl)amino-3-phenoxy-2-propanol dichloride IR (KBr): 3380, 2937, 2709, 1594, 1494, 1457, 1243 cm$^{-1}$ NMR (DMSO-$d_6$, δ) 1.12–1.43 (1H, m), 1.80–2.10 (2H, m), 2.22–2.42 (1H, m), 2.67 (6H, s), 2.72–2.88 (2H, m), 2.98–3.45 (5H, m), 3.95–4.05 (2H, m), 4.10–4.35 (3H, m), 5.92 (1H, br), 6.90–7.02 (3H, m), 7.16–7.42 (5H, m), 8.87 (1H, br), 9.27 (1H, br), 10.81 (1H, br)

(+) APCI-MASS (m/z): 369 (M+H)$^+$

EXAMPLE 141

A mixture of N-[8-[(2S)-2-hydroxy-3-phenoxypropyl]amino-6,7,8,9-tetrahydro-5H-benzocyclohepten-2-yl]methyl acetamide hydrochloride (100 mg) and 1N aqueous hydrochloric acid solution (2 ml) was heated to reflux for 18 hours. The solvent was removed under reduced pressure to dryness. The residue was triturated in diisopropyl ether, and the precipitated powder was collected by filtration to afford (2S)-1-[(3-aminomethyl-6,7,8,9-tetrahydro-5H-benzocyclohepten-6-yl)amino]-3-phenoxy-2-propanol dihydrochloride (94 mg).

IR (KBr) 3382, 2933, 1594, 1494, 1241 cm$^{-1}$

NMR (DMSO-$d_6$, δ): 1.12–1.38 (1H, m), 1.77–2.10 (2H, m), 2.28–2.42 (1H, m), 2.70–2.82 (2H, m), 2.95–3.32 (5H, m), 3.88–4.00 (2H, m), 4.02 (2H, d, J=4.6 Hz), 4.23–4.33 (1H, m), 5.94 (1H, br), 6.92–6.99 (3H, m), 7.18 (1H, d, J=7.5 Hz), 7.27–7.74 (4H, m), 8.49 (3H, br s), 9.00 (1H, br s), 9.46 (1H, br s)

(+) APCI-MASS (m/z): 341 (M+H)$^+$

EXAMPLE 142

A mixture of N-[(2R)-3-(3-methylsulfonylamino-4-benzyloxy)phenyl-2-hydroxypropyl]-N-[(6RS)-(3-methoxy-6,7,8,9-tetrahydro-5H-benzocyclohepten-6-yl)benzylamine (34 mg), 50% wet palladium (10%) on charcoal (10 mg) and methanol (1 ml) was stirred under hydrogen (1 atm) at room temperature for 1.5 hours. The reaction mixture was filtered and evaporated. The residue was purified by preparative TLC (eluent; 25% methanol-dichloromethane) to give N-[(2R)-3-(3-methylsulfonylamino-4-hydroxy)phenyl-2-hydroxypropyl]-[(6RS)-(3-methoxy-6,7,8,9-tetrahydro-5H-benzocyclohepten-6-yl]amine (6.9 mg).

IR (KBr): 3446, 2925, 1612, 1500, 1267, 1157, 1106 cm$^{-1}$

NMR (CD$_3$OD, δ) 1.4–2.2 (4H, m), 2.40–2.9 (9H, m), 2.86 (3H, d, J=2.0 Hz), 3.74 (3H, s), 3.7–3.9 (1H, m), 6.57–6.83 (4H, m), 6.95 (1H, d, J=8.1 Hz), 7.15 (1H, br s)

MASS (m/z): 435 (M)$^+$

EXAMPLE 143

A mixture of (2S)-3-[N-benzyl-N-(3-methoxy-6,7,8,9-tetrahydro-5H-benzocyclohepten-6-yl)amino]-1-(4-acetylamino)phenoxy-2-propanol (80 mg) and 10% palladium on activated carbon (50% wet, 10 mg) in methanol (10 ml) was stirred at room temperature in the presence of hydrogen at an atmospheric pressure for 3 hours and filtered. The filtrate was evaporated in vacuo and treated with 4N hydrogen chloride in ethyl acetate to afford (2S)-3-(3-methoxy-6,7,8,9-tetrahydro-5H-benzocyclohepten-6-yl)amino-1-(4-acetylamino)-phenoxy-2-propanol hydrochloride (80 mg).

(+) APCI-MASS (m/z): 435 (M+H)$^+$

EXAMPLE 144

A mixture of 2-[8-[N'-benzyl-[(2S)-2-hydroxy-3-(1H-indol-5-yloxy)propyl]amino]-6,7,8,9-tetrahydro-5H-benzocyclohepten-2-yl]oxy-N-butylacetamide (160 mg) and 10% palladium on activated carbon (50% wet, 30 mg) in methanol (10 ml) was stirred at room temperature in the presence of hydrogen at an atmospheric pressure for 3 hours and filtered. The filtrate was evaporated in vacuo and treated with 4N hydrogen chloride in ethyl acetate to afford N-butyl-2-[8-[(2S)-2-hydroxy-3-(1H-indol-5-yloxy)propylamino]-6,7,8,9-tetrahydro-5H-benzocyclohepten-2-yloxy]acetamide hydrochloride (133 mg).

(+) APCI-MASS (m/z): 480 (M+H)$^+$

EXAMPLE 145

A mixture of 2-[8-[N'-benzyl-N'-[(2S)-3-(4-benzyloxyphenoxy)-2-hydroxypropyl]amino]-6,7,8,9-tetrahydro-5H-benzocyclohepten-2-yl]oxy-N-butylacetamide (300 mg) and 10% palladium on activated carbon (50% wet, 100 mg) in methanol (10 ml) was stirred at room temperature in the presence of hydrogen at an atmospheric pressure for 3 hours and filtered. The filtrate was evaporated in vacuo and treated with 4N hydrogen chloride in ethyl acetate to afford N-butyl-2-[8-[(2S)-2-hydroxy-3-(4-hydroxyphenoxy)propyl]amino-6,7,8,9-tetrahydro-5H-benzocyclohepten-2-yloxy]acetamide hydrochloride (190 mg).

(+) APCI-MASS (m/z): 457 (M+H)$^+$

EXAMPLE 146

A mixture of (2S)-1-[N-benzyl-N-(3-hydroxy-6,7,8,9-tetrahydro-5H-benzocyclohepten-6-yl)amino]-3-phenoxy-2-propanol (320 mg) and 10% palladium on activated carbon (50% wet, 100 mg) in methanol (20 ml) was stirred at room temperature in the presence of hydrogen at an atmospheric pressure for 3 hours and filtered. The filtrate was evaporated in vacuo and treated with 4N hydrogen chloride in ethyl acetate to afford (2S)-1-[3-hydroxy-6,7,8,9-tetrahydro-5H-benzocyclohepten-6-yl)amino]-3-phenoxy-2-propanol hydrochloride (161 mg).

NMR (DMSO-$d_6$, δ): 1.20–1.35 (1H, m), 1.75–2.10 (2H, m), 2.20–2.30 (1H, m), 2.60–2.75 (2H, m), 2.90–3.35 (5H, m), 4.00 (2H, s), 4.22 (1H, br s), 5.90 (1H, d, J=4.8 Hz), 6.50–6.70 (2H, m), 6.80–7.05 (4H, m), 7.20–7.45 (2H, m), 9.25 (1H, s)

(+) APCI-MASS (m/z): 328 (M+H)+

EXAMPLE 147

A mixture of (2S)-1-[N-benzyl-N-(2,3-dimethoxy-6,7,8,9-tetrahydro-5H-benzocyclohepten-6-yl)amino]-3-phenoxy-2-propanol (400 mg) and 10% palladium on activated carbon (50% wet, 100 mg) in methanol (10 ml) was stirred at room temperature in the presence of hydrogen at an atmospheric pressure for 3 hours and filtered. The filtrate was evaporated in vacuo and treated with 4N hydrogen chloride in ethyl acetate to afford (2S)-1-[2,3-dimethoxy-6,7,8,9-tetrahydro-5H-benzocyclohepten-6-yl)amino]-3-phenoxy-2-propanol hydrochloride (282 mg).

(+) APCI-MASS (m/z): 372 (M+H)+

EXAMPLE 148

A mixture of (2S)-1-[N-benzyl-N-(1,4-dimethoxy-5,6,8,9-tetrahydro-5H-benzocyclohepten-7-yl) amino]-3-phenoxy-2-propanol (70 mg) and 10% palladium on activated carbon (50% wet, 10 mg) in methanol (10 ml) was stirred at room temperature in the presence of hydrogen at an atmospheric pressure for 3 hours and filtered. The filtrate was evaporated in vacuo and treated with 4N hydrogen chloride in ethyl acetate to afford (2S)-1-[1,4-dimethoxy-5,6,8,9-tetrahydro-5H-benzocyclohepten-7-yl)amino]-3-phenoxy-2-propanol hydrochloride (446 mg).

(+) APCI-MASS (m/z): 408 (M+H)+

EXAMPLE 149

A mixture of (2S)-1-[N-benzyl-N-(3-methoxy-6,7,8,9-tetrahydro-5H-benzocyclohepten-5-yl) amino]-3-phenoxy-2-propanol (750 mg) and 10% palladium on activated carbon (50% wet, 200 mg) in methanol (10 ml) was stirred at room temperature in the presence of hydrogen at an atmospheric pressure for 3 hours and filtered. The filtrate was evaporated in vacuo and treated with 4N hydrogen chloride in ethyl acetate to afford (2S)-1-[3-methoxy-6,7,8,9-tetrahydro-5H-benzocyclohepten-5-yl)amino]-3-phenoxy-2-propanol hydrochloride (100 mg).

(+) APCI-MASS (m/z): 342 (M+H)+

EXAMPLE 150

To a solution of 2-[8-[N-tert-butoxycarbonyl-N-[(2S)-2-hydroxy-3-phenoxypropyl]amino]-6,7,8, 9-tetrahydro-5H-benzocyclohepten-2-yloxy]acetic acid (100 mg), 1-(3-dimethylaminopropyl)-3-ethylcarbodiimide (61 mg) and 1-hydroxybenzotriazole (33 mg) in dichloromethane (10 ml) was added 5-aminotetrazole monohydrate (19.3 mg). The resulting mixture was stirred at room temperature for 18 hours and extracted with ethyl acetate. The extract was washed with brine, dried over magnesium sulfate and evaporated in vacuo. The residue was chromatographed (hexane-ethyl acetate) over silica gel and treated with 4N hydrogen chloride in ethyl acetate to afford 2-[8-[(2S)-2-hydroxy-3-phenoxypropyl)amino]-6,7,8,9-tetrahydro-5H-benzocyclohepten-2-yloxy]-2-(tetrazol-5-yl)acetamide (50 mg).

NMR (DMSO-d$_6$, δ): 1.60–2.10 (3H, m), 2.20–2.30 (1H, m), 2.60–3.60 (7H, m), 3.80–4.30 (2H, m), 4.71 (1H, s), 4.85 (1H, s), 6.60–7.40 (8H, m)

EXAMPLE 151

To a solution of guanidine hydrochloride (463 mg) in N,N-dimethylformamide (20 ml) was added 28% sodium ethoxide (0.22 ml) under ice-cooling, and the mixture was stirred at room temperature for 5 minutes. To the resulting mixture was added 2-[8-[(2S)-2-hydroxy-3-phenoxypropyl] amino-6,7,8,9-tetrahydro-5H-benzocyclohepten-2-yloxy] acetic acid ethyl ester (400 mg). After being stirred at room temperature for 2 hours, the precipitates were collected by filtration and treated with 4N hydrogen chloride in ethyl acetate to afford N-[2-[8-[(2S)-2-hydroxy-3-phenoxypropyl]amino-6,7,8,9-tetrahydro-5H-benzocyclohepten-2-yloxy]acetyl]guanidine hydrochloride (243 mg).

(+) APCI-MASS (m/z): 427 (M+H)+

EXAMPLE 152

A mixture of N-[8-[N-benzyl-N-[(2S)-2-hydroxy-3-phenoxypropyl]amino]-6,7,8,9-tetrahydro-5H-benzocyclohepten-2-ylmethyl]urea (160 mg) and 10% palladium on activated carbon (50% wet, 50 mg) in methanol (10 ml) was stirred at room temperature in the presence of hydrogen at an atmospheric pressure for 3 hours and filtered. The filtrate was evaporated in vacuo and treated with 4N hydrogen chloride in ethyl acetate to afford N-[8-[(2S)-2-hydroxy-3-phenoxypropyl]amino-6,7,8,9-tetrahydro-5H-benzocyclohepten-2-ylmethyl]urea hydrochloride (100 mg).

(+) APCI-MASS (m/z): 384 (M+H)+

EXAMPLE 153

A mixture of 1-[8-[N-benzyl-N-[(2S)-2-hydroxy-3-phenoxypropyl]amino]-6,7,8,9-tetrahydro-5H-benzocyclohepten-2-ylmethyl]-3-butylurea (105 mg) and 10% palladium on activated carbon (50% wet, 50 mg) in methanol (10 ml) was stirred at room temperature in the presence of hydrogen at an atmospheric pressure for 3 hours and filtered. The filtrate was evaporated in vacuo and treated with 4N hydrogen chloride in ethyl acetate to afford 1-butyl-3-[8-(2S)-2-hydroxy-3-phenoxypropyl)amino-6,7,8,9-tetrahydro-5H-benzocyclohepten-2-ylmethyl]urea hydrochloride (80 mg).

(+) APCI-MASS (m/z): 440 (M+H)+

EXAMPLE 154

A mixture of 3-[[8-[N-benzyl-N-[(2S)-2-hydroxy-3-phenoxypropyl]amino]-6,7,8,9-tetrahydro-5H-benzocyclohepten-2-ylmethyl]amino]propionic acid tert-butyl ester (100 mg) and 10% palladium on activated carbon (50% wet, 10 mg) in methanol (10 ml) was stirred at room temperature in the presence of hydrogen at an atmospheric pressure for 3 hours and filtered. The filtrate was evaporated in vacuo and treated with 4N hydrogen chloride in ethyl acetate to afford 3-[[8-[(2S)-2-hydroxy-3-phenoxypropylamino]-6,7,8,9-tetrahydro-5H-benzocyclohepten-2-ylmethyl]amino]propionic acid dihydrochloride (80 mg).

NMR (DMSO-d$_6$, δ): 1.10–1.40 (1H, m), 1.70–2.10 (3H, m), 2.15–3.30 (13H, m), 3.95–4.25 (3H, m), 6.80–7.40 (8H, m), 8.63 (1H, br s)

EXAMPLE 155

A mixture of 2-[8-[N-benzyl-N-[(2S)-2-hydroxy-3-[4-benzyloxy-3-methanesulfonylamino]phenoxypropyl]amino]-6,7,8,9-tetrahydro-5H-benzocyclohepten-2-yloxy]-N-butylacetamide (160 mg) and 10% palladium on activated carbon (50% wet, 30 mg) in methanol (10 ml) was stirred at room temperature in the presence of hydrogen at an atmospheric pressure for 3 hours and filtered. The filtrate was evaporated in vacuo and treated with 4N hydrogen chloride in ethyl acetate to afford N-butyl-2-[8-[[(2S)-2-hydroxy-3-[4-hydroxy-3-methanesulfonylamino]phenoxypropyl]amino]-6,7,8,9-tetrahydro-5H-benzocyclohepten-2-yloxy]acetamide hydrochloride (446 mg).

NMR (DMSO-$d_6$, δ) 0.85 (3H, t, J=7.1 Hz), 1.20–1.50 (5H, m), 1.60–2.10 (2H, m), 2.22–2.30 (1H, m), 2.70–2.80 (1H, m), 2.94 (3H, s), 3.05–3.30 (7H, m), 3.90 (2H, d, J=4.5 Hz), 4.10–4.25 (1H, m), 4.41 (2H, s), 6.60–6.80 (2H, m), 6.85–6.95 (3H, m), 7.05 (1H, d, J=8.2 Hz), 8.04 (1H, br s)

(+) APCI-MASS (m/z): 480 (M+H)$^+$

EXAMPLE 156

A mixture of (2S)-1-[N-benzyl-N-(3-methoxy-6,7,8,9-tetrahydro-5H-benzocyclohepten-6-yl)amino]-3-(4-benzyloxy-3-methanesulfonylamino)phenoxy-2-propanol (750 mg) and 10% palladium on activated carbon (50% wet, 200 mg) in methanol (10 ml) was stirred at room temperature in the presence of hydrogen at an atmospheric pressure for 3 hours and filtered. The filtrate was evaporated in vacuo and treated with 4N hydrogen chloride in ethyl acetate to afford (2S)-3-[3-methoxy-6,7,8,9-tetrahydro-5H-benzocyclohepten-6-yl]amino-1-(4-hydroxy-3-methanesulfonylamino)phenoxy-2-propanol hydrochloride (446 mg).

(+) APCI-MASS (m/z): 342 (M+H)$^+$

EXAMPLE 157

To a solution of 2-[8-[N-tert-butoxycarbonyl-N-[(2S)-2-hydroxy-3-phenoxypropyl]amino]-6,7,8,9-tetrahydro-5H-benzocyclohepten-2-yloxy]acetic acid (200 mg), 1-(3-dimethylaminopropyl)-3-ethylcarbodiimide (122 mg) and 1-hydroxyenzotriazole hydrate (66 mg) in dichloromethane (20 ml) was added dimethylamine hydrochloride (38.4 mg), and the mixture was stirred at room temperature for 18 hours. The resulting mixture was diluted with ethyl acetate. The organic layer was washed with brine, dried over magnesium sulfate and evaporated in vacuo. The residue was chromatographed (hexane-ethyl acetate) over silica gel and treated with 4N hydrogen chloride in ethyl acetate to afford 2-[8-[[(2S)-2-hydroxy-3-phenoxypropyl]amino]-6,7,8,9-tetrahydro-5H-benzocyclohepten-2-yloxy]-N,N-dimethylacetamide (100 mg).

NMR (DMSO-$d_6$, δ): 1.10–1.40 (1H, m), 1.60–2.10 (2H, m), 2.20–2.30 (1H, m), 2.55–3.30 (13H, m), 3.90–4.30 (3H, m), 4.70 (2H, s), 6.89–7.35 (8H, m)

(+) APCI-MASS (m/z): 413 (M+H)$^+$

EXAMPLE 158 TO EXAMPLE 201

Coupling of 2-[8-[N-tert-butoxycarbonyl-N-[(2S)-2-hydroxy-3-phenoxypropyl]amino]-6,7,8,9-tetrahydro-5H-benzocyclohepten-2-yloxy]acetic Acid with n Different Type of Amines To a solution of 2-[8-[N-tert-butoxycarbonyl-N-[(2S)-2-hydroxy-3-phenoxypropyl]amino]-6,7,8,9-tetrahydro-5H-benzocyclohepten-2-yloxy]acetic acid (Starting compound) (n×0.01 mmol), 1-(3-dimethylaminopropyl)-3-ethylcarbodiimide (n×0.015 mmol) and 1-hydroxybenzotriazole (n×0.012 mmol) in N,N'-dimethylformamide (n×0.1 ml) was added 1M N,N-dimethylformamide solution of an amine (0.012 mmol) [n different type of amines] and stirred at room temperature for 2 hours.

To each reaction mixture was added 5% sodium hydrogencarbonate solution (0.40 ml), following by extraction with ethyl acetate (0.35 ml). The resultant aqueous layer was further extracted with ethyl acetate (0.2 ml). The combined organic layer was washed with water (0.30 ml). Then the resultant aqueous layer was additionally extracted with ethyl acetate (0.2 ml×2). The combined organic layer was concentrated by nitrogen flow and treated with 4N hydrogen chloride in ethyl acetate and concentrated by nitrogen flow. The resultant residue was dissolved in dimethylsulfoxide (1.0 ml) to give a ca. 1.0×10$^{-2}$M dimethylsulfoxide solution of the object compound which was subjected to analysis by mass spectrum.

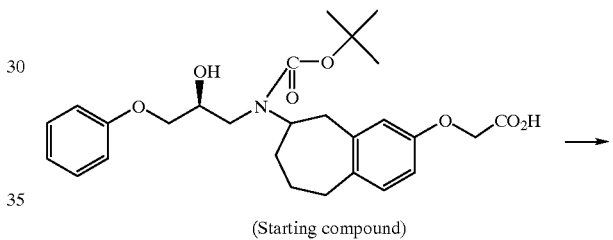

(Starting compound)

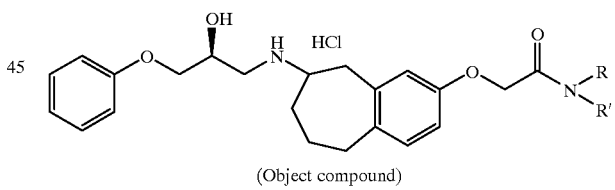

(Object compound)

The formula

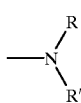

of the Object compounds and their spectrums in the following Examples 158 to Example 201 in Table 1.

| Example No. | | MALDI-MS (m/z) |
|---|---|---|
| 158 | 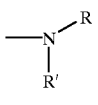 | 457 (M + H)+ |
| 159 | 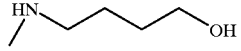 | 455 (M + H)+ |
| 160 | 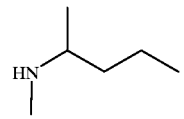 | 443 (M + H)+ |
| 161 | 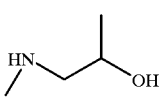 | 485 (M + H)+ |
| 162 | 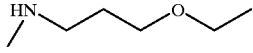 | 443 (M + H)+ |
| 163 | 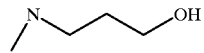 | 498 (M + H)+ |
| 164 | 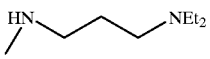 | 467 (M + H)+ |
| 165 | 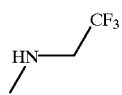 | 543 (M + H)+ |
| 166 | 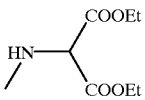 | 498 (M + H)+ |
| 167 | 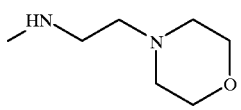 | 490 (M + H)+ |
| 168 | 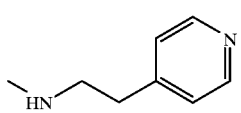 | 476 (M + H)+ |
| 169 | 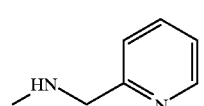 | 493 (M + H)+ |
| 170 | 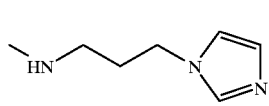 | 517 (M + H)+ |

-continued
| Example No. | (R')) | MALDI-MS (m/z) |
|---|---|---|
| 171 |  | 558 (M + H)+ |
| 172 | 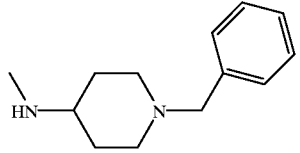 | 573 (M + H)+ |
| 173 | 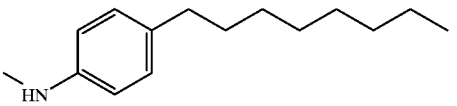 | 517 (M + H)+ |
| 174 |  | 529 (M + H)+ |
| 175 | 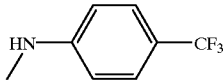 | 506 (M + H)+ |
| 176 | 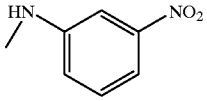 | 479 (M + H)+ |
| 177 | 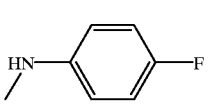 | 532 (M + H)+ |
| 178 | 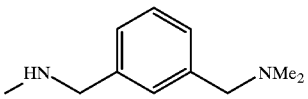 | 620 (M + H)+ |
| 179 | 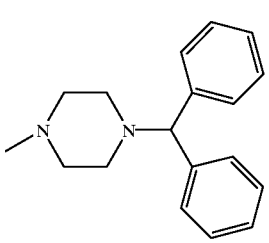 | 565 (M + H)+ |

-continued
| Example No. | | MALDI-MS (m/z) |
|---|---|---|
| 180 |  | 680 (M + H)+ |
| 181 | 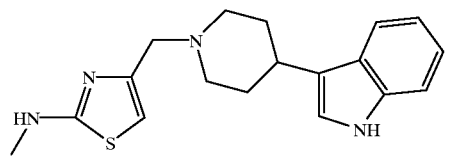 | 623 (M + H)+ |
| 182 | 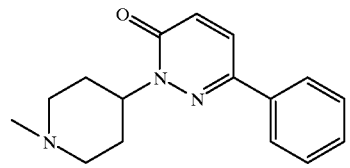 | 489 (M + H)+ |
| 183 | 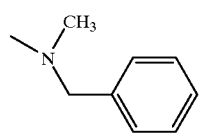 | 565 (M + H)+ |
| 184 | 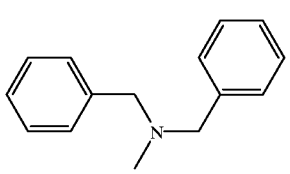 | 542 (M + H)+ |
| 185 | 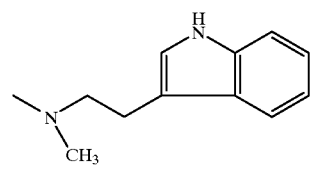 | 504 (M + H)+ |
| 186 | 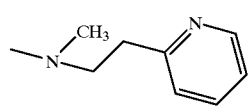 | 475 (M + H)+ |
| 187 | 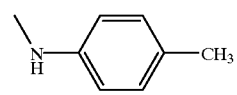 | 491 (M + H)+ |
| 188 |  | 495 (M + H)+ |
| 189 | 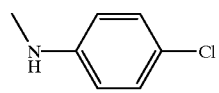 | 468 (M + H)+ |

-continued

| Example No. | –N(R)(R') group | MALDI-MS (m/z) |
|---|---|---|
| 190 | 1-methyl-2,3-dihydroindol-5-yl (N-Me indoline) | 487 (M + H)⁺ |
| 191 | 4-(difluoromethoxy)phenyl-NH– (with N-Me) | 527 (M + H)⁺ |
| 192 | N-ethyl-N-propyl | 455 (M + H)⁺ |
| 193 | N-methyl-N-isobutyl (CH₃, isobutyl) | 455 (M + H)⁺ |
| 194 | N-ethyl-N-butyl | 469 (M + H)⁺ |
| 195 | N-methyl-N-hexyl | 483 (M + H)⁺ |
| 196 | 3-fluorophenyl-NH– (with N-Me) | 479 (M + H)⁺ |
| 197 | 4-(dimethylamino)phenyl-NH– (with N-Me) | 504 (M + H)⁺ |
| 198 | 4-fluorophenyl-NH– (with N-Me) | 479 (M + H)⁺ |
| 199 | N-benzyl-N-phenyl | 551 (M + H)⁺ |

| Example No. | | MALDI-MS (m/z) |
|---|---|---|
| 200 | 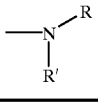 N(CH₃)-CH₂CH₂-phenyl | 503 (M + H)⁺ |
| 201 | 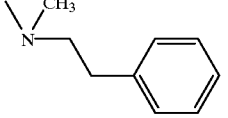 H₃C-N(−)-cyclohexyl | 481 (M + H)⁺ |

EXAMPLE 202

Under nitrogen, a solution of 2-(8-amino-6,7,8,9-tetrahydro-5H-bnzocyclohepten-2-yloxy)-N,N-dimethylacetamide (129 mg), N-[2-benzyloxy-5-[(1R)-2-iodo-1-(triethylsilyloxy)ethyl]phenyl]methanesulfonamide (280 mg) and N,N-diisopropylethylamine (0.34 ml) in 1,3-dimethyl-2-imidazolidinone (5 ml) was stirred at 110° C. for 42 hours. The resulting mixture was poured into saturated aqueous sodium hydrogencarbonate and extracted with ethyl acetate. The organic layer was washed with brine, dried over anhydrous sodium sulfate and evaporated in vacuo. To the residue in ethyl acetate (4 ml) was added 4N hydrogen chloride in ethyl acetate (1 ml), and the mixture was stirred at room temperature for 1.5 hours. After evaporation, the residue was dissolved into a mixture of saturated aqueous sodium hydrogencarbonate and ethyl acetate, followed by separation. The organic layer was washed with brine, dried over anhydrous magnesium sulfate, and evaporated in vacuo. The residue was purified by column chromatography on silica gel (chloroform:methanol=50:1 to 10:1) to give 2-[8-[(2R)-2-(4-benzyloxy-3-methanesulfonylamino)phenyl-2-hydroxyethylamino]-6,7,8,9-tetrahydro-5H-benzocyclohepten-2-yloxy]-N,N-dimethylacetamide (145 mg).

NMR (CHCl₃, δ): 1.4–2.1 (4H, m), 2.55–3.15 (7H, m), 2.91 (3H, s), 2.96 (3H, m), 3.08 (3H, m), 4.45–4.7 (3H, m), 5.10 (2H, s), 6.65–6.8 (2H, m), 6.9–7.0 (2H, m), 7.1–7.2 (1H, m), 7.35–7.55 (6H, m)

(+) APCI-MASS (m/z): 582 (M+H)⁺

The following compound was obtained according to a similar manner to that of Example 202.

EXAMPLE 203

2-(8-[(2R)-2-Hydroxy-2-(4-hydroxy-3-methanesulfonylaminophenyl)ethylamino]-6,7,8,9-tetrahydro-5H-benzocyclohepten-2-yloxy]-N,N-dimethylacetamide hydrochloride NMR (DMSO-d₆, δ): 1.1–1.4 (1H, m), 1.7–2.05 (2H, m), 2.2–2.4 (1H, m), 2.55–3.2 (7H, m), 2.83 (3H, s), 2.95 (3H, s), 2.99 (3H, s), 4.73 (2H, s), 4.8–4.95 (1H, m), 6.67 (1H, dd, J=2.2 and 8.2 Hz), 6.75–6.9 (1H, m), 6.9–7.4 (4H, m)

(+) APCI-MASS (m/z): 492 (M−HCl+H)⁺

EXAMPLE 204

Under nitrogen, to a solution of N-[3-[(1S)-2-amino-1-hydroxyethyl]-4-fluorophenyl]methanesulfonamide (200 mg) and 3-methoxy-6,7,8,9-tetrahydrobenzocyclohepten-6-one (146 mg) in tetrahydrofuran (10 ml) was added sodium triacetoxyborohydride (257 mg) at room temperature, and the mixture was stirred at the same temperature for 24 hours. The resulting mixture was poured into saturated aqueous sodium bicarbonate solution and extracted with ethyl acetate. The organic layer was washed with brine, dried over magnesium sulfate and evaporated in vacuo. The residue was treated with 4N hydrogen chloride in ethyl acetate to afford N-[4-fluoro-3-[(1S)-1-hydroxy-2-(3-methoxy-6,7,8,9-tetrahydro-5H-benzocyclohepten-6-ylamino)ethyl]phenyl]-methanesulfonamide hydrochloride (304 mg).

(+) APCI-MASS (m/z): 423 (M+H)⁺

EXAMPLE 205

Under nitrogen, a solution of 3-methoxy-6,7,8,9-tetrahydro-5H-benzocyclohepten-6-ylamine (720 mg), N-[2-benzyloxy-5-[(1R)-2-iodo-1-(triethylsilyloxy)ethyl]phenyl]-methanesulfonamide (2.1 g) and N,N-diisopropylethylamine (2.6 ml) in N,N-dimethylacetamide (10 ml) was stirred at 110° C. for 96 hours. The resulting mixture was poured into aqueous 10% sodium hydrogensulfite and extracted with ethyl acetate. The organic layer was successively washed with saturated aqueous sodium hydrogencarbonate and brine, dried over anhydrous sodium sulfate and evaporated in vacuo. The residue was purified by column chromatography on silica gel (chloroform:methanol=40:1 to 20:1) to give N-[2-benzyloxy-5-[(1R)-1-hydroxy-2-(3-methoxy-6,7,8,9-tetrahydro-5H-benzocyclohepten-6-ylamino)ethyl]phenyl]methanesulfonamide (381 mg).

NMR (CDCl₃, δ) 1.4–2.1 (5H, m), 2.5–3.1 (7H, m), 2.90 (3H, s), 3.77 (3H, s), 4.5–4.6 (1H, m), 5.10 (2H, s), 6.6–6.75 (2H, m), 6.97 (1H, d, J=8.5 Hz), 6.99 (1H, d, J=8.0 Hz), 7.1–7.2 (1H, m), 7.3–7.5 (5H, m), 7.50 (1H, d, J=1.8 Hz)

(+) APCI-MASS (m/z): 511 (M+H)⁺

The following compound was obtained according to a similar manner to that of Example 132.

EXAMPLE 206

N-[2-Hydroxy-5-(1R)-1-hydroxy-2-(3-methoxy-6,7,8,9-tetrahydro-5H-benzocyclohepten-6-ylamino)ethyl]phenyl]methanesulfonamide hydrochloride NMR (DMSO-d₆, δ): 1.05–1.4 (1H, m), 1.7–2.1 (2H, m), 2.2–2.4 (1H, m), 2.6–2.8 (2H, m), 2.9–3.3 (5H, m), 2.95

(3H, s), 3.71 (3H, s), 4.8–4.95 (1H, m), 6.65–7.2 (5H, m), 7.28 (1H, s)

(+) APCI-MASS (m/z): 421 (M–HCl+H)⁺

EXAMPLE 207

Under nitrogen, a solution of 2-(8-amino-6,7,8,9-tetrahydro-5H-benzocyclohepten-2-yloxy)acetic acid tert-butyl ester (321 mg), N-[2-benzyloxy-5-[(1R)-2-iodo-1-(triethylsilyloxy)ethyl]phenyl]methanesulfonamide (620 mg) and N,N-diisopropylethylamine (0.77 ml) in 1,3-dimethyl-2-imidazolidinone (5 ml) was stirred at 110° C. for 24 hours. The resulting mixture was poured into saturated aqueous sodium hydrogencarbonate and extracted with ethyl acetate. The organic layer was successively washed with water twice and brine, dried over anhydrous sodium sulfate and evaporated in vacuo. Under nitrogen, to the residue in tetrahydrofuran (10 ml) was added 1M tetra-n-butylammonium fluoride in tetrahydrofuran (2 ml) at 5° C., and the mixture was stirred at room temperature for 1 hour. The resulting mixture was poured into saturated aqueous sodium hydrogencarbonate and extracted with ethyl acetate. The organic layer was washed with brine, dried over anhydrous magnesium sulfate and evaporated in vacuo. The residue was purified by column chromatography on silica gel (chloroform:methanol=50:1) to give 2-[8-[(2R)-2-(4-benzyloxy-3-methanesulfonylamino)phenyl-2-hydroxyethylamino]-6,7,8,9-tetrahydro-5H-benzocyclohepten-2-yloxy]acetic acid tert-butyl ester (366 mg).

(+) APCI-MASS (m/z): 611 (M+H)⁺

EXAMPLE 208

A mixture of 2-[8-[(2R)-2-(4-benzyloxy-3-methanesulfonylaminophenyl)-2-hydroxyethylamino]-6,7,8,9-tetrahydro-5H-benzocyclohepten-2-yloxy]acetic acid tert-butyl ester (353 mg) and 10% palladium on activated carbon (50% wet, 100 mg) in methanol (5 ml) was stirred at room temperature in the presence of hydrogen at an atmospheric pressure for 3.5 hours. After filtration, the filtrate was evaporated in vacuo. The residue was purified by column chromatography on silica gel (chloroform:methanol=10:1 to 5:1) to give 2-[8-[(2R)-2-hydroxy-2-(4-hydroxy-3-methanesulfonylaminophenyl)ethylamino]-6,7,8,9-tetrahydro-5H-benzocyclohepten-2-yloxy]acetic acid tert-butyl ester (268 mg).

(+) APCI-MASS (m/z): 521 (M+H)⁺

EXAMPLE 209

Under nitrogen, to a solution of 2-[8-[(2R)-2-hydroxy-2-(4-hydroxy-3-methanesulfonylaminophenyl)ethylamino]-6,7,8,9-tetrahydro-5H-benzocyclohepten-2-yloxy]acetic acid tert-butyl ester (257 mg) in dichloromethane (5 ml) was added trifluoroacetic acid (1 ml) at 5° C., and the mixture was stirred at room temperature for 3 hours. The resulting mixture was evaporated in vacuo. The residue was treated with 4N hydrogen chloride in 1,4-dioxane to give 2-[8-[(2R)-2-hydroxy-2-(4-hydroxy-3-methanesulfonylaminophenyl)ethylamino]-6,7,8,9-tetrahydro-5H-benzocyclohepten-2-yloxy]acetic acid hydrochloride (247 mg).

(+) APCI-MASS (m/z): 465 (M–HCl+H)⁺

The following compound was obtained according to a similar manner to that of Example 205.

EXAMPLE 210

2-[8-[(2R)-2-(4-Benzyloxy-3-methanesulfonylaminophenyl)-2-hydroxyethylamino]-6,7,8,9-tetrahydro-5H-benzocyclohepten-2-yloxy]-N-phenylacetamide NMR (CDCl₃, δ): 1.4–2.1 (4H, m), 2.5–3.1 (7H, m), 2.90 (3H, s), 4.5–4.65 (1H, m), 4.58 (2H, s), 5.09 (2H, s), 6.71 (1H, dd, J=2.6 and 8.1 Hz), 6.81 (1H, d, J=2.6 Hz), 6.9–7.2 (4H, m), 7.25–7.65 (10H, m), 8.32 (1H, br s)

(+) APCI-MASS (m/z): 630 (M+H)⁺

The following compound was obtained according to a similar manner to that of Example 79.

EXAMPLE 211

2-[8-[(2R)-2-Hydroxy-2-(4-hydroxy-3-methanesulfonylaminophenyl)ethylamino]-6,7,8,9-tetrahydro-5H-benzocyclohepten-2-yloxy]-N-phenylacetamide hydrochloride NMR (DMSO-d₆, δ): 1.1 (4H, m), 2.6–2.8 (2H, m), 2.9–3.7 (8H, m), 4.67 (2H, s), 4.8–4.9 (1H, m), 6.7–7.4 (9H, m), 7.65 (2H, d, J=7.8 Hz)

(+) APCI-MASS (m/z): 540 (M–HCl+H)⁺

EXAMPLE 212

Under nitrogen, a solution of 3-oxiranylpyridine (1.9 g) and N-benzyl-(3-methoxy-6,7,8,9-tetrahydro-5H-benzocyclohepten-6-yl)amine (3.3 9) in ethanol (15 ml) was refluxed for 5 hours. After removal of ethanol in vacuo, the residue was dissolved into a mixture of aqueous sodium hydrogencarbonate and ethyl acetate. After separation, the organic layer was washed with brine, dried over anhydrous magnesium sulfate and evaporated in vacuo. The residue was purified by column chromatography on silica gel (chloroform:methanol=20:1) to give 2-[N-benzyl-N-(3-methoxy-6,7,8,9-tetrahydro-5H-benzocyclohepten-6-yl)amino]-1-(pyridin-3-yl)ethanol (520 mg).

(+) APCI-MASS (m/z): 403 (M+H)⁺

The following compound was obtained according to a similar manner to that of Example 132.

EXAMPLE 213

2-(3-Methoxy-6,7,8,9-tetrahydro-5H-benzocyclohepten-6-yl)amino-1-(pyridin-3-yl)ethanol dihydrochloride (+) APCI-MASS (m/z): 313 (M–2HCl+H)⁺

EXAMPLE 214

A mixture of N-benzyl-(3-methoxy-6,7,8,9-tetrahydro-5H-benzocyclohepten-6-yl)amine (0.30 g) and (R)-3-chlorophenyl oxirane (0.18 g) in ethanol (0.6 ml) was refluxed overnight. The reaction mixture was evaporated in vacuo, and the residue was purified by column chromatography on silica gel eluting with a mixture of hexane and ethyl acetate (5:1). The product (0.43 g) was treated with 4N hydrogen chloride in ethyl acetate and powdered from diisopropyl ether to afford (1R)-2-[N-benzyl-N-(3-methoxy-6,7,8,9-tetrahydro-5H-benzocyclohepten-6-yl)amino]-1-(3-chlorophenyl)ethanol (0.40 g).

NMR (DMSO-d₆, δ): 1.10–1.25 (1H, m), 1.91–2.18 (2H, m), 2.42–2.80 (3H, m), 2.98–3.62 (5H, m), 3.74 (3H, s), 4.43–4.73 (3H, m), 6.36–6.46 (1H, br), 6.68 (1H, d, J=7.9 Hz), 7.01 (1H, d, J=8.3 Hz), 7.11–7.19 (1H, m), 7.29–7.55 (7H, m), 7.68–7.90 (2H, m), 10.00–10.15 (1F, br)

(+) APCI-MASS (m/z): 436, 438 (M+H)⁺

EXAMPLE 215

A mixture of (1R)-2-[N-benzyl-N-(3-methoxy-6,7,8,9-tetrahydro-5H-benzocyclohepten-6-yl)amino]-1-(3- chlorophenyl)ethanol hydrochloride (0.20 g), chlorobenzene (0.86 ml) and 10% palladium on carbon (0.01 g) in methanol (4 ml) was stirred at room temperature under hydrogen atmosphere for 1.5 hours. The catalyst was filtered off and washed with methanol. The filtrate was evaporated in vacuo, and the residue was powdered from diisopropyl ether to afford (1R)-2-[(3-methoxy-6,7,8,9-tetrahydro-5H-benzocyclohepten-6-yl)amino]-1-(3-chlorophenyl)ethanol hydrochloride (0.14 g)

IR (KBr): 3328, 2933, 1608, 1502, 1444, 1261 cm$^{-1}$

NMR (DMSO-d$_6$, δ): 1.17–1.35 (1H, m), 1.78–2.08 (2H, m), 2.22–2.37 (1H, m), 2.62–2.72 (2H, m), 2.98–3.30 (5H, m), 3.71 (3H, s), 4.95–5.05 (1H, m), 6.33 (1H, d, J=4.0 Hz), 6.70 (1H, d, J=8.2 Hz), 6.83 (1H, dd, J=12.3, 2.5 Hz), 7.04 (1H, d, J=8.2 Hz), 7.30–7.43 (3H, m), 7.52 (1H, s), 8.72 (1H, br s), 9.00 (1H, br s)

(+) APCI-MASS (m/z): 346, 348 (M−HCl+H)$^+$

The following compound was obtained according to a similar manner to that of Example 214.

EXAMPLE 216

2-[8-[N-Benzyl-N-[(2R)-2-(3-chlorophenyl)-2-hydroxyethyl]amino]-6,7,8,9-tetrahydro-5H-benzocyclohepten-2-yloxy)-N-phenylacetamide hydrochloride NMR (DMSO-d$_6$, δ) 1.05–1.30 (1H, m), 1.91–2.15 (2H, m), 2.40–2.50 (1H, m), 2.62–2.75 (2H, m), 3.02–3.60 (6H, m), 4.45–4.72 (4H, m), 6.34–6.45 (1H, br), 6.75 (1H, d, J=8.2 Hz), 7.01–7.20 (3H, m), 7.27–7.48 (9H, m), 7.62–7.68 (2H, m), 7.70–7.90 (2H, m), 9.83 (1H, br s), 10.19 (1H, d, J=7.8 Hz)

(+) APCI-MASS (m/z): 555, 557 (M+H)$^+$

The following compound was obtained according to a similar manner to that of Example 215.

EXAMPLE 217

2-[8-[[(2R)-2-(3-Chlorophenyl)-2-hydroxyethyl]amino]-6,7,8,9-tetrahydro-5H-benzocyclohepten-2-yloxy]-N-phenylacetamide IR (KBr) 3394, 2933, 1679, 1600, 1540, 1502, 1442, 1253 cm$^{-1}$ NMR (DMSO-d$_6$, δ): 1.16–1.30 (1H, m), 1.72–2.05 (2H, m), 2.22–2.38 (1H, m), 2.60–2.70 (2H, m), 3.00–3.35 (5H, m), 4.66 (2H, d, J=2.4 Hz), 4.95–5.04 (1H, m), 6.33 (1H, br s), 6.77 (1H, d, J=8.4 Hz), 6.92 (1H, d, J=12.3 Hz), 7.04–7.10 (2H, m), 7.27–7.41 (5H, m), 7.52 (1H, s), 7.62–7.66 (2H, m), 8.75 (1H, br s), 9.12 (1H, br s), 10.16 (1H, d, J=6.1 Hz)

(+) ESI-MASS (m/z): 465, 467 (M+H)$^+$

EXAMPLE 218

According to a similar manner to that of Test 1 described before, the effects of the present compounds on the intravesical pressure were evaluated. Particularly, ED50(μg/kg) of the compound prepared in Example 155 was 10.8.

What is claimed is:
1. A compound of the general formula (I):

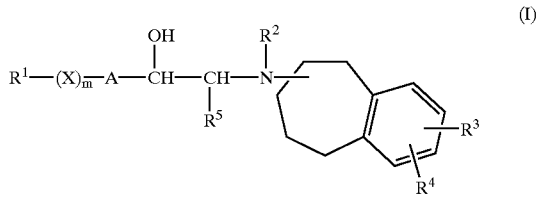

wherein
$R^1$ is aryl which may have one or more suitable substituent(s), heterocyclic group or cyclo(lower)alkyl,
$R^2$ is hydrogen or amino protective group,
$R^3$ and $R^4$ are independently hydrogen, halogen, hydroxy, amino, nitro, carboxy, protected carboxy, aryl, lower alkyl, hydroxy(lower)alkyl, amino(lower)alkyl, acyloxy(lower)alkyl, acylamino(lower)alkyl, lower alkylamino(lower)alkyl which may have one or more suitable substituent(s), mono or di-(lower)alkylamino, acylamino, acyl group, lower alkoxy, halo(lower)alkoxy, lower alkenyloxy, lower alkoxy(lower)alkoxy, aryloxy, cyclo(lower)alkyloxy, heterocyclicoxy, ar(lower)alkyloxy, acyloxy or acyl(lower)alkoxy,
$R^5$ is hydrogen, lower alkyl, or aryl,
A is lower alkylene which may have one or more suitable substituent(s) or lower alkenylene,
X is O, S, SO, SO$_2$ or NH, and
m is an integer of 0 or 1,
or a salt thereof,
wherein when $R^1$ is naphthyl and $R^5$ is H, then X is not O.
2. The compound of claim 1, wherein
$R^1$ is phenyl which may have one or more suitable substituent(s),
$R^2$ is hydrogen,
$R^3$ is acyl(lower)alkoxy, lower alkoxy, protected carboxy, hydroxy or acyloxy,
$R^4$ is hydrogen,
$R^5$ is hydrogen,
A is lower alkylene,
X is O, and
m is an integer of 1.
3. The compound of claim 2, wherein
$R^1$ is phenyl which may have 1 or 2 suitable substituent(s) selected from the group consisting of hydroxy and lower alkylsulfonylamino,
$R^3$ is lower alkylcarbamoyl(lower)alkoxy, heterocycliccarbamoyl(lower)alkoxy, heterocycliccarbonyl(lower)alkoxy, N-lower alkyl-lower alkylcarbamoyl(lower)alkoxy, hydroxy, lower alkoxy, protected carboxy, arylcarbamoyl(lower)alkoxy which may have lower alkoxy or di(lower)alkylamino, di-lower alkylsulfamoyloxy, N-lower alkylheterocyclic(lower)alkylcarbamoyl(lower)alkoxy, N-lower alkyl-lower alkylcarbamoyl(lower)alkoxy or N-lower alkyl-cyclo(lower)alkylcarbamoyl(lower) alkoxy.
4. The compound of claim 3, wherein
$R^1$ is phenyl which may have hydroxy and methylsulfonylamino,
$R^3$ is ethylcarbamoylmethoxy, indolylcarbamoylmethoxy, piperidinocarbonylmethoxy, N-methylbutylcarbamoylmethoxy, hydroxy, butylcarbamoylmethoxy, methoxy, methoxycarbonyl, ethoxy, dimethylsulfamoyloxy, tetrazolylcarbamoylmethoxy, N-methylpyridylethylcarbamoylmethoxy, methoxyphenylcarbamoylmethoxy, thiazolylcarbamoylmethoxy, dihydroindolylcarbonylmethoxy, N-ethylpropylcarbamoylmethoxy, N-methylbutylcarbamoylmethoxy, N-ethylbutylcarbamoylmethoxy, dimethylaminophenylcarbamoylmethoxy or N-methylcyclohexylcarbamoylmethoxy.

5. A process for preparing a compound of claim 1, or a salt thereof, which comprises, (i) reacting a compound (II) of the formula:

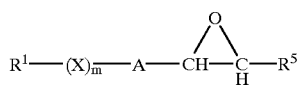

(II)

wherein $R^1$, $R^5$, A, X and m are each as defined in claim 1, with a compound (III) of the formula:

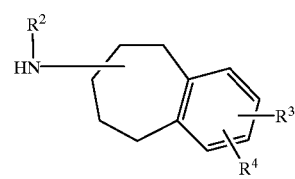

(III)

wherein $R^2$, $R^3$ and $R^4$ are each as defined in claim 1, or a salt thereof, to give a compound (I) of the formula:

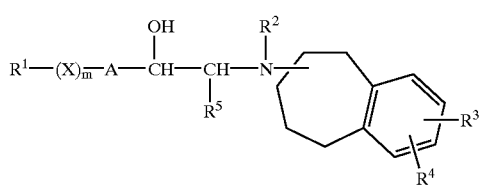

(I)

wherein $R^1$, $R^2$, $R^3$, $R^4$, $R^5$, A, X and m are each as defined in claim 1, or a salt thereof, or (ii) subjecting a compound (Ia) of the formula:

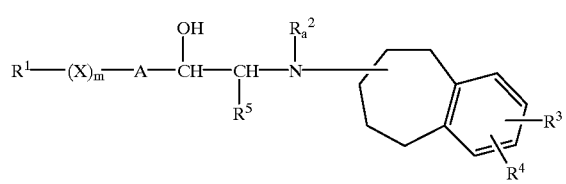

(Ia)

wherein $R^1$, $R^3$, $R^4$, $R^5$, A, X and m are each as defined in claim 1, and $R_a^2$ is amino protective group, or a salt thereof, to elimination reaction of the amino protective group, to give a compound (Ib) of the formula:

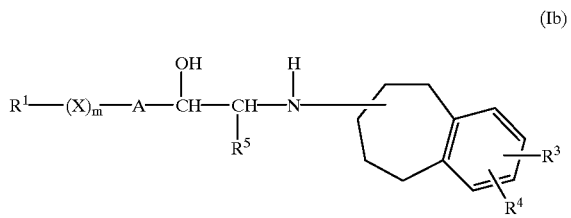

(Ib)

wherein $R^1$, $R^3$, $R^4$, $R^5$, A, X and m are each as defined in claim 1, or a salt thereof.

6. A pharmaceutical composition which comprises a compound of claim 1 or a pharmaceutically acceptable salt thereof in admixture with a pharmaceutically acceptable carrier or excipient.

7. A method for making a pharmaceutical composition or a medicament comprising admixing a compound of claim 1 or a pharmaceutically acceptable salt thereof with a pharmaceutically acceptable carrier or excipient.

8. A compound of claim 1 or a pharmaceutically acceptable salt thereof compounded as a tablet, pellet, troche, capsule, suppository, cream, ointment, aerosol, powder for insufflation, solution, emulsion, or suspension.

9. A method for the prophylactic and/or the therapeutic treatment of pollakiuria or urinary incontinence which comprises administering an effective amount of a compound of claim 1 or a pharmaceutically acceptable salt thereof to a subject in need thereof.

10. A method for agonizing a $\beta_3$ adrenergic receptor comprising contacting said receptor with a compound of claim 1.

11. A method for inducing gut-selective sympathomimetic activity comprising administering an effective amount of a compound of claim 1 to a subject in need thereof.

12. A method for the prophylactic and/or the therapeutic treatment of a gastrointestinal disorder comprising administering an effective amount of a compound of claim 1 or a pharmaceutically acceptable salt thereof to a subject in need thereof.

13. A method for the prophylactic and/or the therapeutic treatment of an ulcer or pancreatitis comprising administering an effective amount of a compound of claim 1 or a pharmaceutically acceptable salt thereof to a subject in need thereof.

14. A method for inducing lypolysis comprising administering an effective amount of a compound of claim 1 or a pharmaceutically acceptable salt thereof to a subject in need thereof.

* * * * *